(12) United States Patent
Yoshida et al.

(10) Patent No.: US 12,420,087 B2
(45) Date of Patent: Sep. 23, 2025

(54) PERIPHERAL NERVE ACTIVATION AND BLOCKING USING CUFF ASSEMBLY AND SINUSOIDAL LOW FREQUENCY ALTERNATING CURRENT

(71) Applicant: The Trustees of Indiana University, Bloomington, IN (US)

(72) Inventors: Kenichi Yoshida, Carmel, IN (US); Michael Ryne Horn, Fishers, IN (US); Awadh Al Hawwash, Indianapolis, IN (US); Nathaniel Lazorchak, Indianapolis, IN (US); Christian Phillip Vetter, Lombard, IL (US); Onna Marie Doering, Indianapolis, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 60 days.

(21) Appl. No.: 18/691,874

(22) PCT Filed: Sep. 15, 2022

(86) PCT No.: PCT/US2022/043612
§ 371 (c)(1),
(2) Date: Mar. 13, 2024

(87) PCT Pub. No.: WO2023/043889
PCT Pub. Date: Mar. 23, 2023

(65) Prior Publication Data
US 2024/0269463 A1     Aug. 15, 2024

Related U.S. Application Data

(60) Provisional application No. 63/247,106, filed on Sep. 22, 2021, provisional application No. 63/244,278, filed on Sep. 15, 2021.

(51) Int. Cl.
*A61N 1/05* (2006.01)
*A61N 1/36* (2006.01)

(52) U.S. Cl.
CPC ....... *A61N 1/0556* (2013.01); *A61N 1/36053* (2013.01)

(58) Field of Classification Search
CPC . A61N 1/36053; A61N 1/0556; A62N 1/0556
See application file for complete search history.

(56) References Cited

U.S. PATENT DOCUMENTS 5,487,756 A     1/1996  Kallesoe et al.
5,824,027 A *  10/1998  Hoffer ................. A61N 1/0556
                                                                600/377

(Continued)

FOREIGN PATENT DOCUMENTS

WO     2008123090 A1   10/2008
WO     2021077022 A1    4/2021

OTHER PUBLICATIONS

International Search Report; International Searching Authority; International Application No. PCT/US2022/043612; Mar. 8, 2023; 5 pages.
Written Opinion of the International Searching Authority; International Searching Authority; International Application No. PCT/US2022/043612; Mar. 8, 2023; 9 pages.

*Primary Examiner* — Alyssa M Alter
(74) *Attorney, Agent, or Firm* — Taft Stettinius & Hollister LLP

(57) ABSTRACT

Nerve stimulation via a Low Frequency Alternating Current (LFAC) waveform can result in blocking of action potential conduction, while an increase in LFAC frequency and/or amplitude can translate into nerve activation. As LFAC for nerve blocking is frequency independent, the threshold LFAC activation can decrease with increasing frequency. Thus, frequency and amplitude settings can determine whether LFAC activates or blocks nerve fibers. LFAC can also be orderly, wherein smaller, non-fatiguing nerve fibers (Continued)

can be activated before larger nerve fibers. LFAC settings for activation can also be influenced by the configuration of a cuff assembly that positions an electrode along a nerve. The cuff can position a nerve in a cuff through hole, and a sliding closure of the cuff can be slide into a radial opening to substantially lock the nerve in the cuff assembly. An electrode material is positioned within a window of the cuff and is connected to an electrical lead. An interface coating on a nerve-facing bioelectric surface of an electrode material, and related compositions and methods, are also provided.

20 Claims, 30 Drawing Sheets

(56) References Cited

U.S. PATENT DOCUMENTS

| | | |
|---|---|---|
| 2004/0111141 A1* | 6/2004 | Brabec .................. A61N 1/056 607/119 |
| 2008/0183264 A1 | 7/2008 | Bly et al. |
| 2010/0168831 A1 | 7/2010 | Korivi et al. |
| 2016/0184581 A1 | 6/2016 | Bonde et al. |
| 2019/0357847 A1 | 11/2019 | Franke et al. |
| 2020/0254249 A1 | 8/2020 | Rondoni et al. |

* cited by examiner

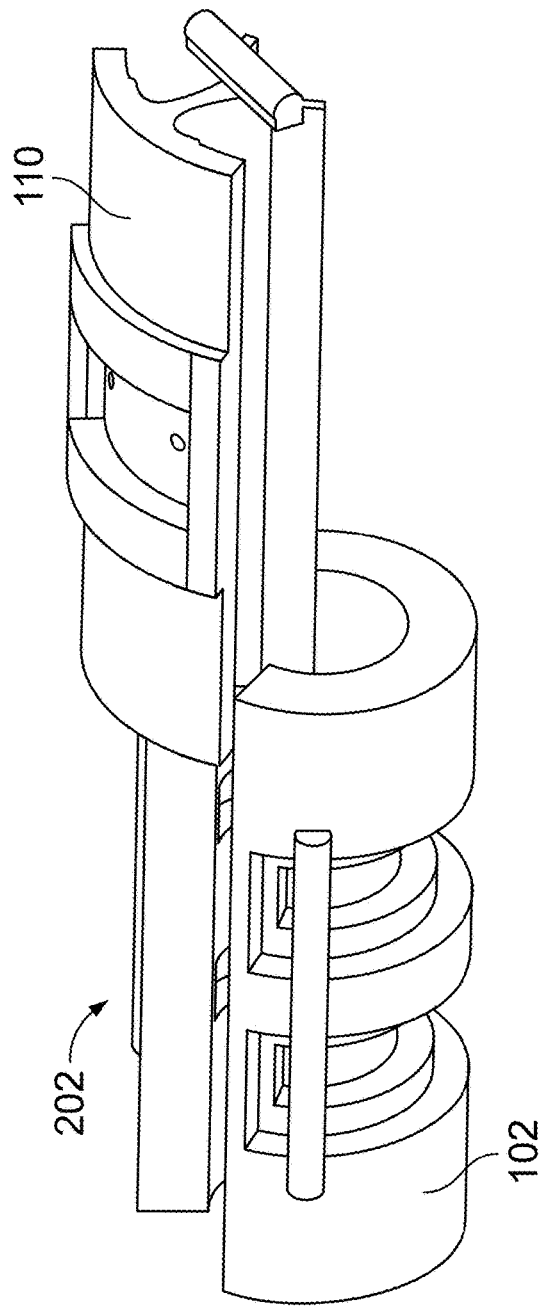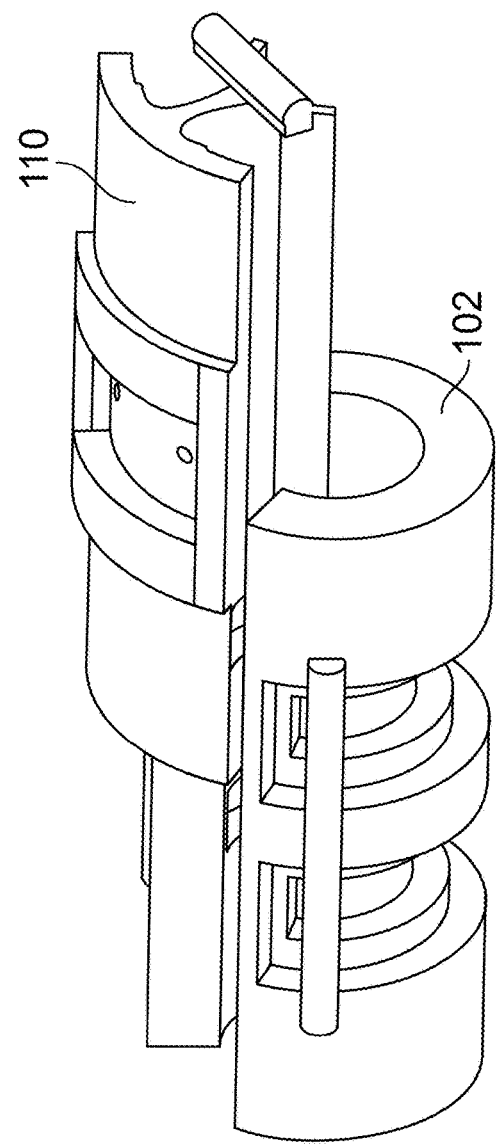

PERIPHERAL NERVE ACTIVATION AND BLOCKING USING CUFF ASSEMBLY AND SINUSOIDAL LOW FREQUENCY ALTERNATING CURRENT

CROSS-REFERENCE TO RELATED APPLICATIONS

The present application claims the benefit of U.S. Provisional Patent Application No. 63/244,278, filed Sep. 15, 2021, and 63/247,106, filed Sep. 22, 2021, the contents of which are incorporated herein by reference in their entirety.

REFERENCE TO GOVERNMENT GRANTS

This invention was made with government support under EB028469 awarded by National Institutes of Health. The Government has certain rights in the invention.

FIELD OF INVENTION

The present application relates to electrical nerve stimulation, and more particularly to peripheral nerve activation and blocking using low frequency alternating current that is applied to a cuff for an implantable neural electrode that provides improved responses.

BACKGROUND

Neuromodulation has seen a considerable increase in attention as an up-and-coming technology to study and treat various nervous system diseases. This process utilizes electrical stimulation to elicit change in neural function. Further, such stimulation can be applied to the central nervous system (CNS) or peripheral nervous system (PNS). Methods of CNS interventions include deep brain stimulation (DBS) through intracranial electrodes and spinal cord stimulation (SCS) by means of subdermal implanted electrodes. PNS interventions include intrafascicular and extrafascicular electrodes that lie within or immediately adjacent to the peripheral nerve, respectively. Stimulation may be delivered in many forms, the most notable including pulses, bursts, and high-frequency alternating current (HFAC) and the recently developed, and less known LFAC. Irrespective of the application, electrodes are to be designed to safely provide therapeutic stimulation whereby electrical current transverses across the boundary to ionic current at the electrode-electrolyte interface.

In the early days of neuromodulation, electrode structures consisted of a bare metal needle, also known as a conventional metal electrode ("CME"). Although good at conducting current, CMEs have drawbacks such as inability to mediate the electrode-electrolyte interface across all forms of electrical stimulation and a high probability of eliciting an immune response. Most notably, CMEs are polarizeable, meaning CMEs disrupt charge-balance by imposing an offset which may permanently damage the nerve. CME drawbacks can be diminished through careful selection of metals that are less polarizeable, such as Pt or Iridium-Oxide, by use of ICPs, or some combination thereof. In the past decade, research has shown that a low polarizable metal-ICP complex is currently the favorable approach to mediating the interface.

Nonetheless, metal-ICP electrodes still possess inherent polarizability which leads to difficulty modulating current, most notably in the lower frequencies. Development of a new electrode that operates across all frequency ranges will manifest in improved functionality and safety for all electrodes while inadvertently providing a suitable structure to prove LFAC a safe and effective method of modulation. The primary steps in developing an electrode for this purpose required minimization of polarization, improved charge storage and charge transfer abilities, and selection of materials that will not delaminate, which is a common flaw in PEDOT-electrode designs. Furthermore, an increased charge transfer window allows for a greater range of stimulation potentials and transmission of larger currents, providing an added benefit in functionality when attempting to modulate the activity of nerve fibers within peripheral nerves using extrafascicular electrodes.

The stimulation and recording performance of implanted neural interfaces are often limited by the electrode contact impedance characteristics of the electrode structure. In particular, the low frequency impedance plays an important role in maintaining recording stability and stimulation performance. This low frequency impedance is especially important when exploring the application of Low Frequency Alternating Currents ("LFAC") ranging from 0.5 Hz to 10 Hz for blocking peripheral nerve activity. Most traditional electrodes have impedances that are completely reactive at low frequencies, leading to extremely high impedance magnitudes in the tens of mega ohms ($M(\Omega)$) to hundreds of mega ohms range. Metal electrodes coated with intrinsically conductive polymers ("ICPs") have been an effective method to improve the impedance characteristics compared to their uncoated states, thus enhancing electrochemical characteristics and enabling investigation of LFAC block. Platinum (Pt)-coated PEDOT effectively interfaces with the metal-electrolyte boundary at low frequencies, but are expensive, can be fragile due to limitations such as poor adhesion of the polymer to the contact surface, and still succumb to slight polarization effects. In an effort to investigate acute neural activity via LFAC, a more durable, cost effective, and electro-chemically stable electrode material is necessary.

Electrode cuffs are often used to create a physical structure to allow electrodes to be positioned around a nerve to monitor the signal going there through and to selectively provide a signal to the nerve among other things. Typical electrode cuffs, however, do not provide contacts that sufficiently contact the perimeter of the nerve when positioned there around and therefore do not provide an ideal interface for monitoring and delivering signals to a nerve.

Further, typical electrode cuffs are difficult to position around the nerve. Conventional electrode cuffs require an opening to become positioned around the nerve and a secondary component to close the opening once positioned around the nerve. One typical configuration utilizes sutures or the like to couple the secondary component to the electrode cuff. These sutures may become loose, allowing the secondary component to move. Further, the sutures may be overly tightened around the electrode cuff to cause undesirable pressure on the surface of the nerve.

Additionally, electrical stimulation (ES) of paralyzed muscles can provide a relatively effective means to slow the degeneration of the muscle and bones in a paralyzed limb. However, the intensity of the therapies often applied may not be sufficient to reverse degeneration. Functional Electrical Stimulation (FES) systems have been under development with the aim to generate, for example, ES based standing, walking, and upper limb use so as to enable able bodied like use of limbs during daily living activities and body weight loading of the skeletal system. ES can also be used to selectively block nerve activity, which can be utilized to assist with pain management.

Generally, a typical limitation of current FES is related to the fatigability of ES activated muscle, which can prevent the use of ES for weight bearing activities or consistent movements, as well as prevent the application of FES outside of supervised facilities. Such fatigability can be attributed to how current pulse stimulation based ES typically activates nerve fibers. Conventional ES is based on a pulse train stimulation having a rectangular pulse waveform that mimics a static electric discharge. For example, the standard ES waveform is a rectangular pulse or a charge balanced rectangular pulse, where the pulse width is typically in the range of approximately 100 μsec through approximately 1000 μsec. The pulse amplitude can range from a few μA's through several mA's. Although the rectangular pulse waveform is considered an efficient means to non-specifically activate nerve fibers, the physics behind the rectangular pulse waveforms makes it easier to activate large diameter nerve fibers over small diameter nerve fibers. This is an order of activation opposite of what typically occurs during natural volitional activation. These large diameter nerve fibers are connected to large metabolically intensive, fast fatiguing muscle fibers. In nature, large diameter nerve fibers are normally activated last, and used to generate large, but short duration, corrective muscle contractions. The slower, smaller, less metabolically intensive muscle fibers, normally used for posture and slow movements are only activated after all of the large fatiguable fibers are activated with standard ES. Thus, standard ES ultimately results in fast fatiguing muscle activation but also, increases the difficulty of controlling ES activated muscle contractions as the inverted muscle fiber utilization causes jerky, inconsistent, and non-smooth muscle movement. Although not critical for artificial muscle activation, other applications critically require small caliber fibers to be activated before activation of larger fibers.

Accordingly, there is a need for an electrode cuff that can easily be positioned around a nerve, provide optimal contact area, and can be easily coupled to the nerve without causing undue pressure on the nerve. Additionally, electrical stimulation in which nerve fibers are activated in the order of natural fiber recruitment remains an area of interest.

BRIEF SUMMARY

The present disclosure in one aspect relates to implantable neural electrodes and electrode manufacturing methods that include making 3d-printed cuff electrode shell parts and using a formable paste including a mixture of a binder or adhesive, such as a cyanoacrylate adhesive, and a carbon filler, such as carbon graphite ("CG"), that can be extruded into openings in a 3d printed cuff shell to form a contact by conductively affixing a lead wire, such as stainless-steel ("SS") wire, within the electrode material. Methods described herein allow for rapid prototyping and manufacturing of durable electrodes.

One embodiment of this disclosure is a cuff assembly for positioning an electrode along a nerve. The cuff assembly has a cuff with a through hole that extends along an axis of the cuff, a radial opening extending along a length of the cuff, a window defined in, and which extends radially through a portion of, the cuff and configured to provide a location for an electrode to be coupled to the cuff, and a sliding closure selectively coupleable to the cuff to substantially close the radial opening. The cuff is sized to position a nerve in the through hole and slide the sliding closure into the radial opening to substantially lock the nerve in the cuff assembly.

One example of this embodiment includes an electrode material positioned at least partially within the window and configured to communicate with electrical signals of a nerve positioned within the through hole. Part of this example has an electrical lead in contact with the electrode material to transfer electrical signals to and from the electrode material. In another part of this example, the electrode material comprises an adhesive and a carbon filler material entrained in the adhesive. In one aspect of this part, the carbon filler material is a carbon graphite material. In another part of this example, the electrode material is coated with an insulated material along a radially exterior surface of the electrode material. In yet another part of this example, the electrode material is coated with an electrochemical coating along a radially interior surface of the electrode material. In one aspect of this part, the electrochemical coating comprises an intrinsically conducting polymer having finely divided conductive particles entrained therein. The finely divided conductive particles have a member selected from the group consisting of carbon black, nano-carbon black, carbon nanotubes, carbon nanoribbons, graphene, and combinations thereof.

Another example of this embodiment has a grounding well defined in the sliding closure at a substantially middle position of the sliding closure. Yet another example has a stop defined at one end of the sliding closure, wherein the stop contacts the cuff once fully coupled to the cuff to prevent further movement of the sliding closure relative to the cuff. In yet another example, the radial opening is about sixty degrees. Further, in one part of this disclosure the electrode material surrounds about 270-275 degrees about the through hole.

In yet another example of this embodiment, the cuff has a C-shaped profile sized to extend approximately 80 percent of the through hole circumference. In another example, the cuff has a wall thickness of no more than about 500 micrometers (μm). In yet another example, the window is inset. In one example, the sliding closure has an overlap on either side of the radial opening along the length of the cuff when positioned therein.

Another embodiment of this disclosure is a method of forming a cuff assembly. The method includes providing a cuff having a through hole defined through an axis of the cuff, a radial opening extending along a length of the cuff, and a window that extends through a portion of the cuff to the through hole and is configured to provide a location for an electrode to be coupled to the cuff, providing a closure that is selectively coupleable to the cuff to substantially close the radial opening, forming an electrode material within the window, the electrode material comprising an adhesive and a carbon filler material, and electrochemically coating a first surface of the electrode material facing toward the through hole with an ICP having finely divided conductive particles entrained therein. The cuff is sized to position a nerve in the through hole so the nerve is positioned at least partially along the electrode material.

One example of this embodiment includes, before said forming, placing the cuff around a mold having a diameter similar to the through hole and masking the window with silicone from the inner surface to the inset edge. Another example includes, before said forming, adding wires through the window before or during the filling the window step. Part of this example includes, before said coating, insulating a second surface of the electrode material facing away from the through hole and the wires extending from the electrode material.

In another example of this embodiment, the ICP comprises poly(3,4 ethylenedioxythiophene):poly(4-styrenesulfonic acid) (PEDOT:PSS). In part of this example, said finely divided conductive particles are selected from the group consisting of carbon black (CB), nano-carbon black, carbon nanotubes, carbon nanoribbons, graphene, and combinations thereof.

The present disclosure in another aspect relates to a material that is useful as an interface coating on a nerve-facing bioelectric surface of an electrode for delivering an electrical impulse to a nerve in an animal, as well as methods for making an interface coating and electrodes that comprise the material.

In one embodiment, a method for forming an interface coating on a nerve-facing bioelectric surface of an electrode for delivering an electrical impulse to a nerve in an animal includes (i) providing an aqueous solution or suspension comprising 3,4-ethylenedioxy-thiophene (EDOT), poly(4-styrenesulfonic acid) (PSS) and a carbon nanomaterial, (ii) submerging in the aqueous solution or suspension an electrode configured for delivering an electrical impulse to a nerve in an animal, wherein a nerve-facing bioelectric surface of the electrode is in contact with the aqueous solution or suspension, and (iii) forming an interface coating on the nerve-facing bioelectric surface by electrodeposition. The interface coating thus formed comprises electroplated poly(3,4 ethylenedioxythiophene):poly(4-styrenesulfonic acid) with a dispersed carbon nanomaterial filler.

In some embodiments, the carbon nanomaterial comprises carbon black. In some embodiments, the aqueous solution or suspension comprises from about 2 to about 5 mg/mL EDOT, from about 4 to about 10 mg/mL PSS and from about 0.5 to about 4 mg/mL carbon black. In some embodiments, the electrodeposition comprises potentiostatic deposition at a DC voltage of from about +0.5 to about +1.5 for a time period of from about 15 minutes to about 25 minutes. In some embodiments, the electrodeposition comprises galvanostatic deposition at from about +150 to about +250 µA for a time period of from about 3 minutes to about 7 minutes. In some embodiments, the interface coating has an average thickness of from about 100 micrometer (µm) to about 1 millimeter (mm). It is to be understood, however, that the interface coating may have an average thickness outside this range. In one embodiment, the interface coating has an average thickness effective less than 100 µm provided that the coating forms a continuous layer over the electrode. In another embodiment, the interface coating has an average thickness greater than 1 mm provided that the coating retains sufficient flexibility to limit the incidence of cracking during use. In some embodiments, the bioelectric surface is a bioelectric surface of an implantable electrode. In some embodiments, the implantable electrode comprises an implantable cuff. In some embodiments, the bioelectric surface is configured for external contact with a skin surface for delivery of an electrical signal to a nerve through the skin.

In some embodiments, the method further includes, before submerging the electrode in the aqueous solution or suspension, covering one or more surface of the electrode material on which the interface coating is not to be formed. In some embodiments, the nerve-facing bioelectric surface of the electrode upon which the interface coating is formed is a porous surface. In some embodiments, the porous surface is composed of an adhesive and a carbon filler material. In some embodiments, the carbon filler material comprises a carbon graphite material. In some embodiments, the adhesive comprises a cyanoacrylate adhesive.

In another embodiment, this disclosure provides an electrode made in accordance with any of the above method embodiments. In one embodiment, an electrode for delivering an electrical impulse to a nerve in an animal includes a bioelectric surface configured to face a nerve when the electrode is positioned for use and an interface coating on the bioelectric surface, wherein the interface coating comprises electroplated poly(3,4 ethylenedioxythiophene):poly(4-styrenesulfonic acid) with a dispersed carbon nanomaterial filler.

In some embodiments, the carbon nanomaterial comprises carbon black. In some embodiments, the interface coating has an average thickness of from about 100 micrometer (µm) to about 1 millimeter (mm). In some embodiments, the bioelectric surface is a bioelectric surface of an implantable electrode. In some embodiments, the implantable electrode comprises an implantable cuff. In some embodiments, the bioelectric surface is configured for external contact with a skin surface for delivery of an electrical signal to a nerve through the skin. In some embodiments, the nerve-facing bioelectric surface of the electrode upon which the interface coating is formed is a porous surface. In some embodiments, the porous surface is composed of an adhesive and a carbon filler material. In some embodiments, the carbon filler material comprises a carbon graphite material. In some embodiments, the adhesive comprises a cyanoacrylate adhesive.

In another embodiment, the present disclosure provides a conductive material comprising poly(3,4 ethylenedioxythiophene):poly(4-styrenesulfonic acid) (PEDOT:PSS) with a dispersed carbon nanomaterial filler entrained therein, wherein the carbon nanomaterial filler is randomly dispersed within the PEDOT:PSS. In another embodiment, the present disclosure provides a conductive material comprising first and second layers, wherein the first layer comprises a porous surface in contact with the second layer, and wherein the second layer comprises poly(3,4 ethylenedioxythiophene):poly(4-styrenesulfonic acid) with a dispersed carbon nanomaterial filler. In some embodiments of these materials, the carbon nanomaterial comprises carbon black.

In some embodiments of the conductive material comprising first and second layers, the porous surface is composed of an adhesive and a carbon filler material. In some embodiments, the carbon filler material comprises a carbon graphite material. In some embodiments, the adhesive comprises a cyanoacrylate adhesive. In some embodiments, the second layer has an average thickness of from about 100 micrometer (µm) to about 1 millimeter (mm).

The present disclosure in another aspect relates to a method for treating a nerve of a patient that includes delivering an electrical stimulation to a cuff assembly that is secured to, or around, the nerve, the electrical stimulation being a low frequency alternating current (LFAC) waveform.

In one embodiment of the present disclosure, a method includes delivering a LFAC waveform to a cuff assembly, the cuff assembly being configured for implantation in or around a nerve and having a plurality of electrodes. A frequency of the LFAC waveform can be increased to transition from a first frequency utilized for nerve block to a second frequency utilized for nerve activation, the first frequency can be less than 4 Hz and is less than the second frequency. The method can also include transmitting, from one or more of the plurality of electrodes and to the nerve, an electrical signal corresponding to the delivered LFAC waveform, and monitoring a to a receipt of the transmitted electrical signal.

Another embodiment of the present disclosure is a method for treating a nerve of a patient that includes delivering an electrical stimulation to a cuff assembly that is secured to, or around, the nerve, the electrical stimulation being a low frequency alternating current (LFAC) waveform having a frequency of less than 100 hertz (Hz). Further, at least one of the frequency and an amplitude and of the LFAC waveform can be adjusted to elicit either a block or an activation the nerve.

A further embodiment of the present disclosure is a system that can include a control system having a voltage controlled voltage source, a pattern generator, and a linear optolsolator. The pattern generator can be configured to generate a LFAC waveform for at least nerve activation, the LFAC waveform having a frequency between 0.1 HZ and 40 Hz. The system can also include a cuff assembly that can be configured for implantation in a patient. The cuff assembly can have a plurality of electrodes, one or more of the plurality of electrodes being electrically coupled to the control system and adapted to deliver an electrical signal corresponding to the LFAC waveform.

These and other aspects of the present invention will be better understood in view of the drawings and following detailed description.

BRIEF DESCRIPTION OF THE DRAWINGS

The description herein makes reference to the accompanying figures wherein like reference numerals refer to like parts throughout the several views.

FIG. 2b is an elevated perspective view of the cuff assembly of FIG. 1 with the sliding closure in a partially opened configuration or position.

FIG. 2c is an elevated perspective view of the cuff assembly of FIG. 1 with the sliding closure in a partially closed configuration or position.

Figure 1:
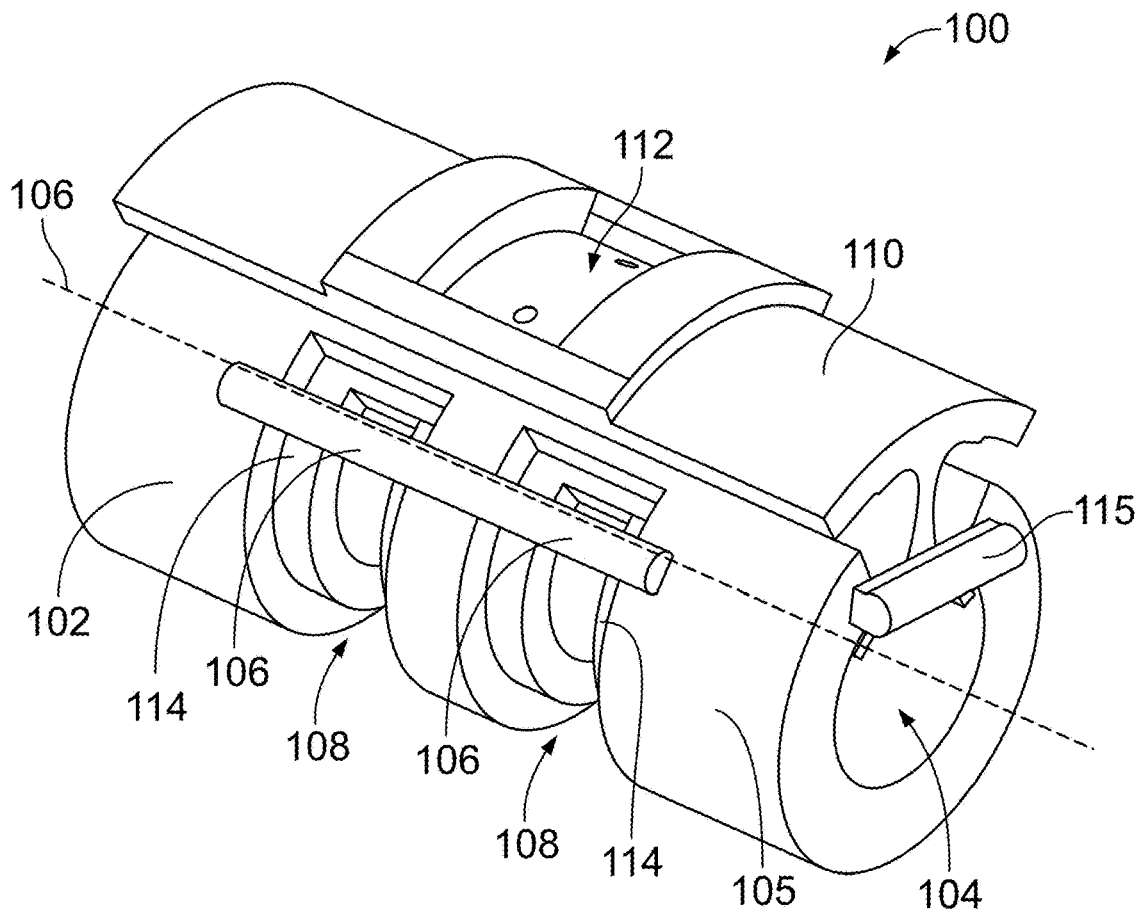
FIG. 1 is an elevated perspective view of one embodiment of a cuff assembly of this disclosure.

The foregoing summary, as well as the following detailed description of certain embodiments of the present application, will be better understood when read in conjunction with the appended drawings. For the purpose of illustrating the application, there is shown in the drawings, certain embodiments. It should be understood, however, that the present application is not limited to the arrangements and instrumentalities shown in the attached drawings. Further, like numbers in the respective figures indicate like or comparable parts.

DESCRIPTION OF THE ILLUSTRATED EMBODIMENTS

For the purposes of promoting an understanding of the principles of the present disclosure, reference will now be made to the embodiments described herein and illustrated in the drawings and specific language will be used to describe the same. It will nevertheless be understood that no limitation of the scope of the present disclosure is thereby intended, such alterations and further modifications in the illustrated devices and methods, and such further applications of the principles of the present disclosure as illustrated therein being contemplated as would normally occur to one skilled in the art to which the present disclosure relates.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "includes", "comprises", "including" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, the term "and/or" includes any and all combinations of one or more of the associated listed items. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Throughout this disclosure, various quantities, such as amounts, sizes, dimensions, proportions and the like, are presented in a range format. It should be understood that the description of a quantity in range format is merely for convenience and brevity and should not be construed as an inflexible limitation on the scope of any embodiment. Accordingly, the description of a range should be considered to have specifically disclosed all the possible subranges as well as all individual numerical values within that range unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 4.62, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

FIG. 1 illustrates one embodiment of a cuff assembly 100 of the present disclosure. The cuff assembly 100 comprises a shell or cuff 102. The cuff 102 is formed of any biocompatible material that may be implanted and received by a living organism. In one embodiment, the cuff 102 is composed of a photopolymer resin, such as clear photopolymer resin FLGPCL04 (Formlabs, Inc., Somerville, MA). It is to be understood, however, that a wide variety of resins can be used to manufacture a cuff in accordance with this disclosure, provided that the resin is capable of producing a cuff having acceptable physical properties for such use, including, without limitation, durability, biocompatibility, rigidity and electrical insulating properties.

The cuff 102 has a substantially cylindrical through hole 104 defined therethrough by a generally cylindrical cuff wall 105 along a substantially central axis 106. The through hole 104 has a diameter that is meant to correspond with the particular nerve to which the cuff assembly 100 is intended to be coupled. Accordingly, the through hole 104 can have a different diameter for different intended nerve applications. As will be discussed in more detail herein, the teachings of this disclosure may be scaled to fit many different nerve-type applications.

The cuff 102 has one or more windows 108 formed radially through a portion of the cylindrical wall 105 of the cuff 102. In the embodiment shown, the window 108 has an inset 114 about a radially inner portion of the window 102. Among other things, the inset 114 can provide additional surface area for an electrode material adhesion. An inner portion of the window 108 defines an opening that can provide an unobstructed exposure to the through hole 104. As will be described in more detail herein, the windows 108 are to be filled with an electrode material composed of an adhesive and a carbon filler material to provide an electrical contact to a nerve that is, or will be, positioned along the through hole 104.

In the embodiment shown, each window 108 has a window cover 106 extending across a portion of the window 108 on either side of a sliding closure 110. The window cover 106 can help to retain a wire during the fabrication process, the wire being operable to provide a conduit for transferring electrical signals to and from the electrode material positioned in the window 108. Further, the window cover 106 can help to retain the electrode material in the window 108, thereby providing additional structural stability to the cuff assembly 100 with wires coupled to the electrode material in each window 108.

Figure 3:
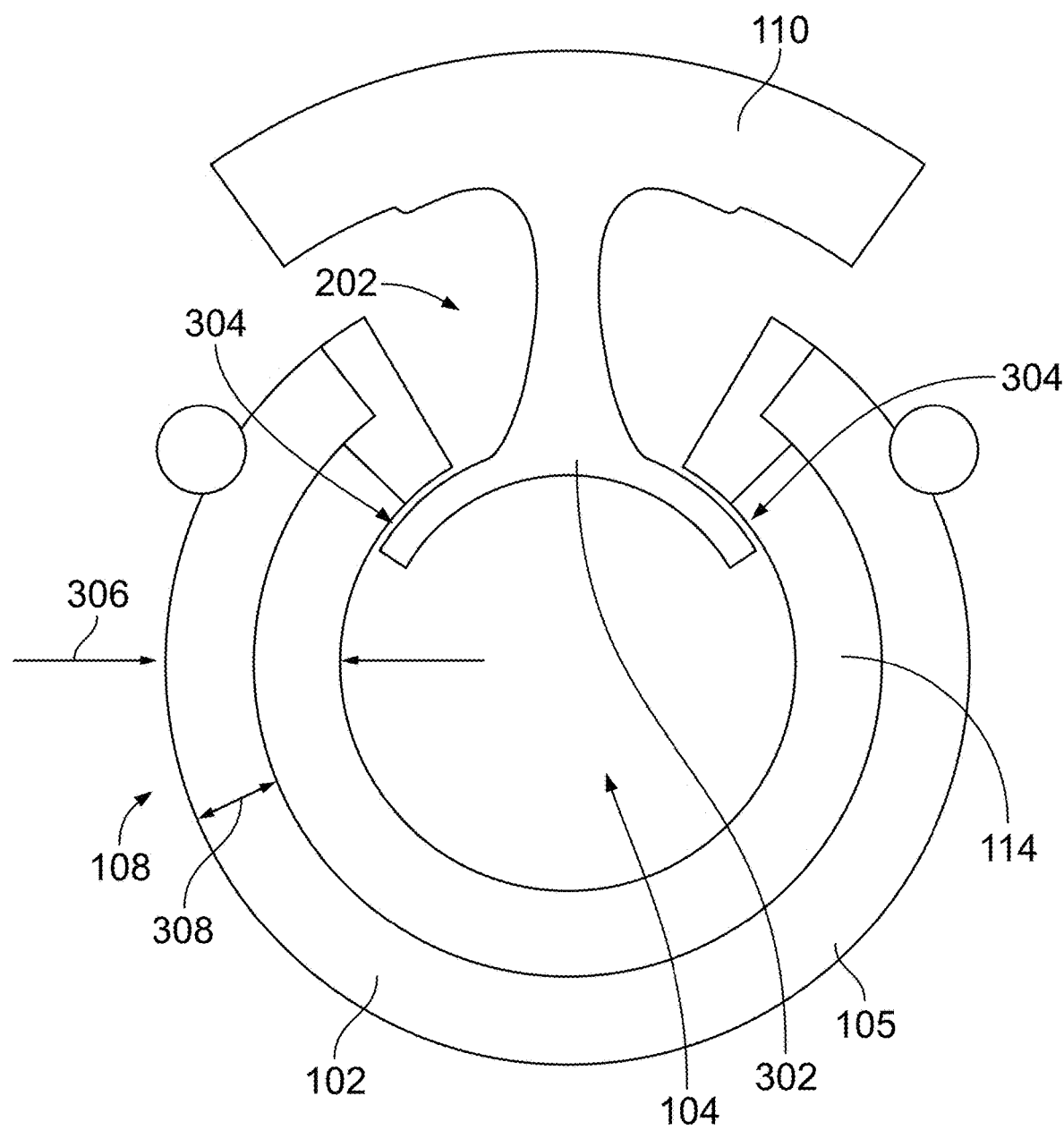
FIG. 3 is a cross section view through a window of the cuff assembly of FIG. 1.

The sliding closure 110 is sized to fit partially within a radial opening 202 of the cuff 102. According to certain embodiments, the radial opening 202 can extend from, and through, one end of the cuff 102, and to, and through, an opposing end of the cuff 102 in a direction, such as, for example, a longitudinal direction, that is generally parallel to the axis 106. Additionally, the radial opening 202 can extend through the wall 105 of the cuff 102 such that passage to the through hole 104 is accessible through the radial opening 202 from a position that is exterior to the cuff 102. More specifically, the sliding closure 110 can have an arc-shaped I-beam configuration that can include a lower segment 302 with an overlap 304 on either side of the radial opening 202, as best shown in FIG. 3. The overlap 304 is disposed radially inward relative to the surrounding cuff 102. As illustrated in the section view of FIG. 3, the lower segment 302 can overlap 304 the adjacent cuff 102 such that the through hole 104 is substantially surrounded by the cuff 102, the electrode material (see FIG. 5) and the lower segment 302 of the sliding closure 110. In this configuration, signals sent or received through the electrode material can be substantially isolated from the surrounding environment and directed towards the nerve positioned through the through hole 104 when the nerve is properly positioned within the cuff assembly 100.

The sliding closure 110 can also have a grounding well 112 defined therein. In the embodiment shown, the grounding well 112 is positioned at an isopotential line. Further, in the example provided by FIG. 1, the grounding well 112 is at a substantially middle plane of the sliding closure 110. This positioning corresponds with a substantially middle or ground plane of the cuff 102 along a symmetrical divide of the cuff assembly 100 when the sliding closure 110 is fully coupled thereto. The grounding well 112 can provide a location for a ground electrode to be coupled to the cuff assembly 100. Positioning the ground electrode on the grounding well 112 along the ground plane can be beneficial in that the potential seen by the ground electrode at such a location can be substantially zero.

The sliding closure 110 has a stop 115 positioned at one end of the sliding closure 110. The stop 115 is sized to extend from the sliding closure 110 to contact the cuff 102 when the sliding closure 110 is properly positioned in the radial opening 202 and slid axially along the axis 106 to the fully closed position illustrated in FIGS. 1 and 2c. The stop 115 can ensure that the sliding closure 110 does not move past the fully closed position within the radial opening when properly coupled to the cuff 102 during a cuff implantation procedure.

Figure 2A:
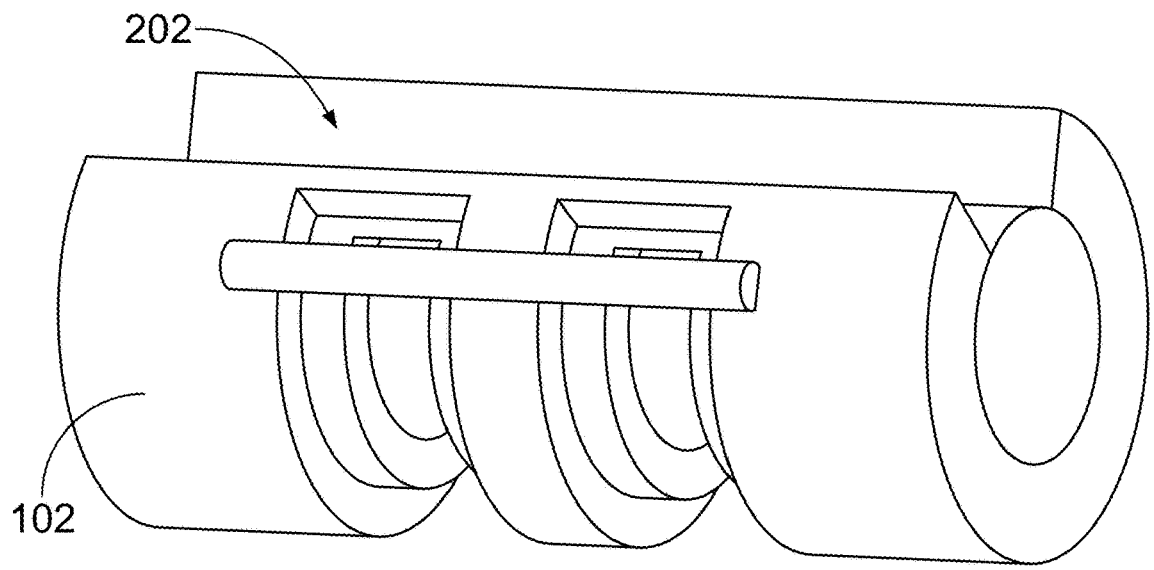
FIG. 2a is an elevated perspective view of the cuff assembly of FIG. 1 in a fully opened configuration with a sliding closure of the cuff assembly removed.

FIGS. 2a-2c illustrate configurations of the cuff assembly 100 with: the sliding closure 110 removed (FIG. 2a); the sliding closure 110 in a partially engaged configuration or position (FIG. 2b); and, the sliding closure in a partially closed configuration or position (FIG. 2c). The cuff 102 is illustrated without the sliding closure 110 in FIG. 2a. This configuration allows the cuff 102 to be positioned around a nerve to which it is intended to be coupled. More specifically, when the sliding closure 110 is removed from the cuff 102, the radial opening 202 can be aligned with the nerve and the cuff 102 positioned so the nerve is positioned along the through hole 104. Once the nerve is positioned in the through hole 104 of the cuff 102, the sliding closure 110 may be positioned along the radial opening 202 with the overlaps 304 of the lower segment 302 aligned radially within the radial opening 202, as illustrated in FIG. 2b. Then, the sliding closure 110 can be slid axially in a direction generally parallel to, and offset from, the axis 106 to become orientated in the partially closed configuration, as shown in FIG. 2c. Finally, the sliding closure 110 can be fully displaced to the closed configuration or orientation, at which the stop 115 contacts the cuff 102, thereby indicating the sliding closure 110 is fully coupled to the cuff 102 within the radial opening 202.

Referring now to FIG. 3, a cross-section through one of the windows 108 is illustrated. As seen from the view of FIG. 3, the wall 105 of the cuff 102 can have a total thickness 306. In one embodiment, the total thickness of the wall of cuff 102 can be about 500 µm. However, other thicknesses are considered herein as well. In another embodiment, the total thickness of the wall 105 of the cuff 302 is from about 300 µm to about 700 µm. In yet another embodiment, the total thickness of the wall 105 of cuff 102 is from about 400 µm to about 600 µm. Further, the thickness 306 can be substantially the same regardless of the size of the through hole 104. Also illustrated in FIG. 3 is the inset 114 having an inset depth 308. In one embodiment, the inset depth 308 can be about 250 µm. However, other inset depths are also considered herein. In another embodiment, the inset depth 308 is from about 150 µm to about 350 µm. In yet another embodiment, the inset depth 308 is from about 200 µm to about 300 µm.

Figure 4:
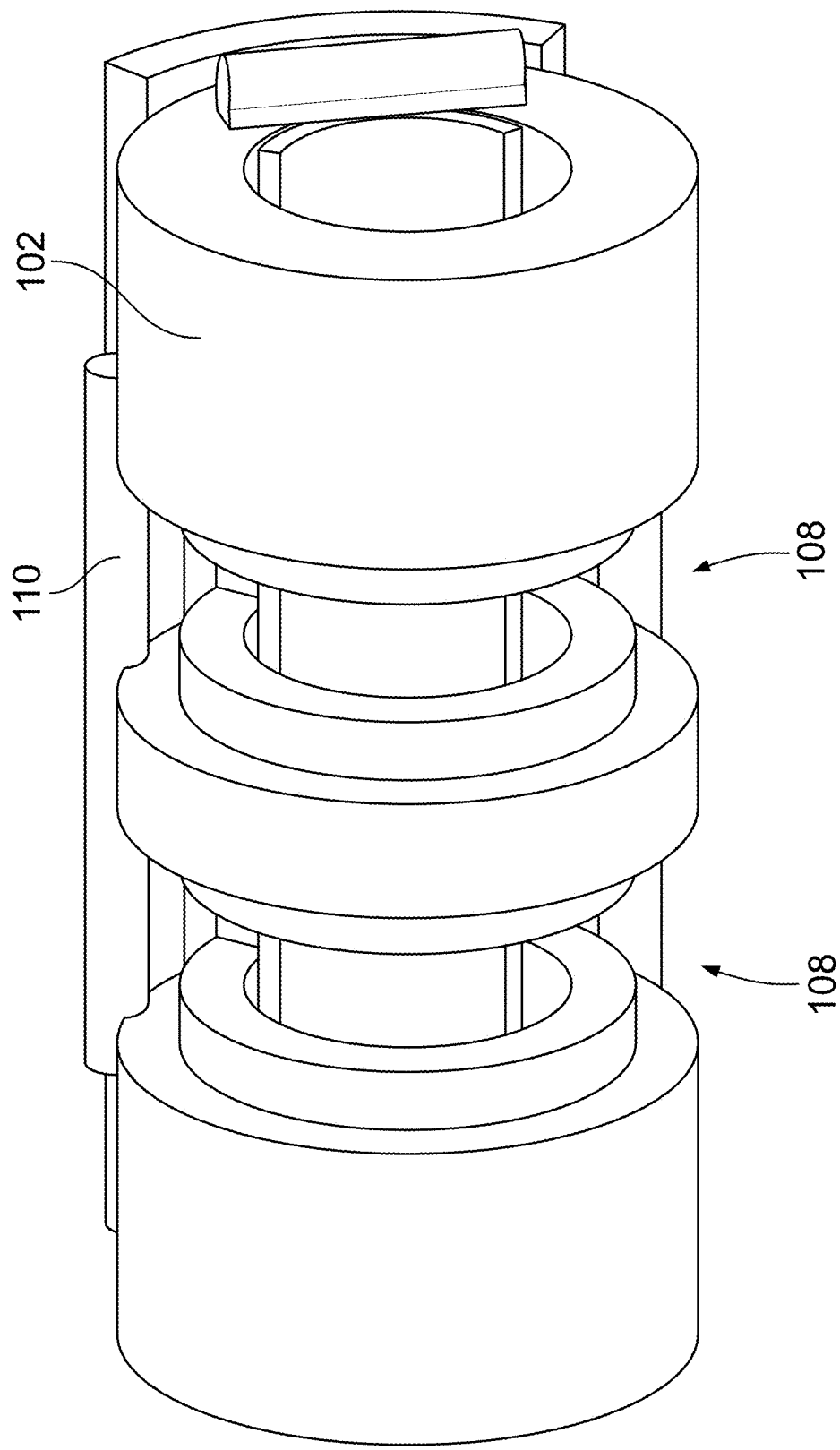
FIG. 4 is a bottom view of the cuff assembly of FIG. 1.
Figure 5:
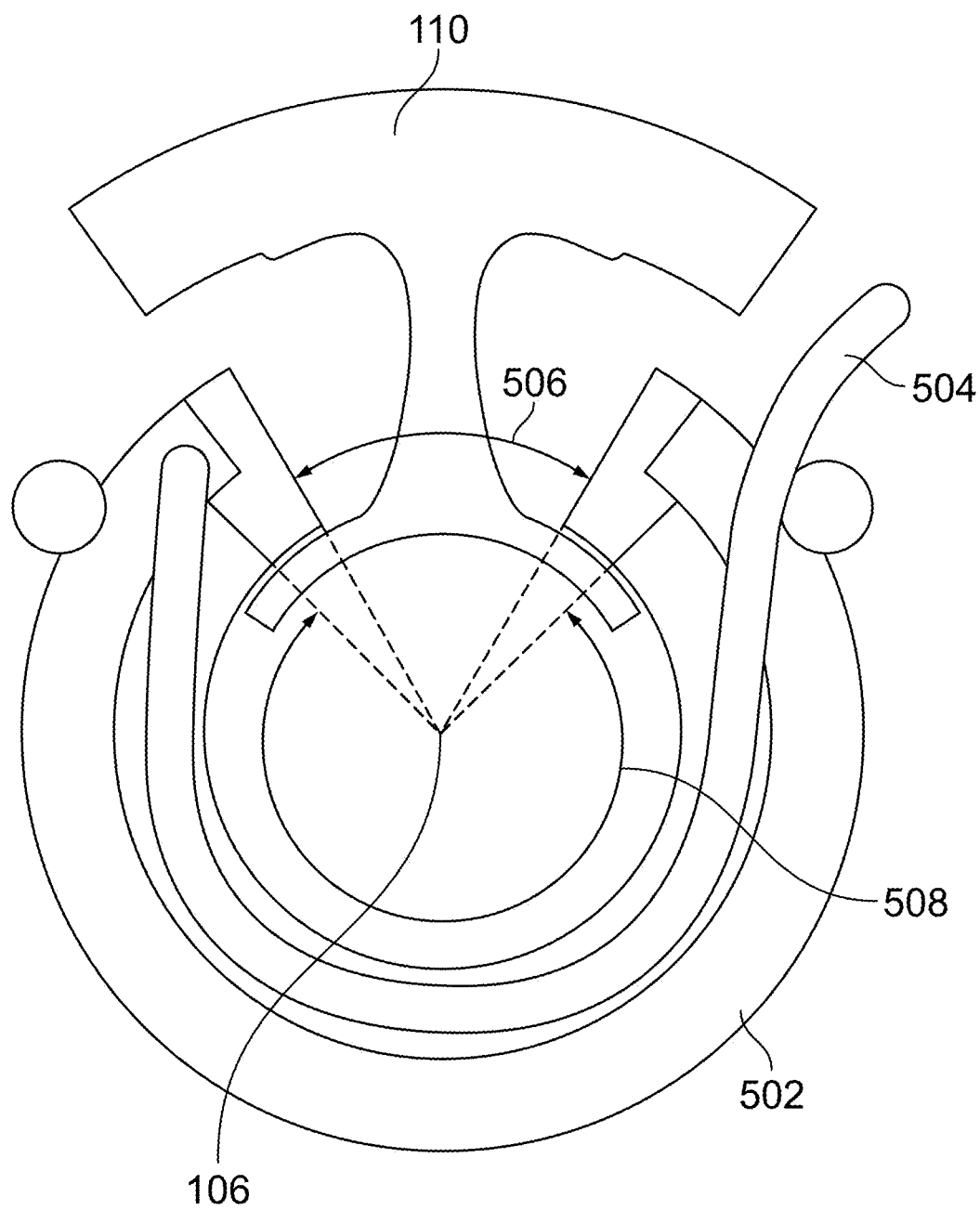
FIG. 5 is the section view of FIG. 4 with electrode material and a wire formed in the window.

Referring now to FIG. 4, a bottom perspective view of the cuff assembly 100 is illustrated. As illustrated, in the exemplary cuff assembly, the windows 108 extend at least partially around the through hole 104 to provide a contact surface for the electrode material when the electrode material is positioned within the windows 108. FIG. 5 is an illustrative example of cross-section view of a window 108 with an electrode material 502 formed within the window 108 and a wire 504 embedded and retained within the electrode material 502. The electrode material 502 can be formed by preparing an adhesive slurry or paste with a carbon filler dispersed therein (the slurry or paste referred to herein as an "electrode precursor material"), positioning the slurry or paste within the window 108 and allowing the adhesive to cure. In one example, the adhesive comprises a cyanoacrylate adhesive such as products offered by KrazyGlue© and the carbon additive is carbon graphite. It is to be understood, however, that this disclosure also contemplates the use of alternative binders or adhesives in place of KrazyGlue©, and contemplates the use of other carbon additives in place of carbon graphite. The electrode material 502 positioned within the window 108 is operable to communicate with electrical signals of a nerve positioned within the through hole 104 when cuff assembly 100 is properly implanted.

The electrode precursor material is prepared and applied to the window 108 and the wire 504 is at least partially positioned therein either before or during introduction of the electrode precursor material into the window 108, or after introduction of the electrode precursor material into the window 108, but before it cures or sets. The electrode precursor material is then cured or allowed to dry to form electrode material 502 with the wire 504 embedded therein. Then, the radially exterior portions of the electrode material 502, cuff 102, and sliding closure 110 can be coated with an insulating material. In one example, the radially exterior surfaces can be insulated with print media and UV cured. However, other insulating materials and processes are considered herein. Finally, assembled cuffs 102 and/or cuff assemblies 100 are electrochemically coated. In some embodiments, the electrochemical coating is an ICP. In one embodiment, the electrochemical coating is formed by electrodeposition of a poly(3,4-ethylenedioxy-thiophene):poly (4-styrenesulfonic acid) (PEDOT:PSS) solution. In another embodiment, the PEDOT:PSS solution is doped with finely divided electrically conductive particles. In other non-limiting examples, the electrochemical coating is a polypyrrole, a polyacetylene, a polyaniline, an alternative polythiophene, and combinations thereof, which may optionally be co-polymerized with a polysulfone, and which also can optionally doped with finely divided electrically conductive particles. Examples of suitable finely divided electrically conductive particles include, without limitation, carbon black, nano-carbon black, carbon nanotubes, carbon nanoribbons, graphene, and combinations thereof. After electrochemical coating, the cuff assembly 100 can be packaged and stored for later use.

According to certain embodiments, the radial opening 202 can have a radial opening angle 506. The radial opening angle 506 can be defined about the axis 106 and can generally define a width of the radial opening in a direction that is generally perpendicular to the axis 106. Further, according to certain embodiments, e the radial opening angle 506 is about sixty degrees. However, other angles for the radial opening angle 506 are also considered herein.

The electrode material 502 can also extend within the window 108 and/or along the through hole 104 of the cuff 102 at an electrode material angle 508 about the axis 106. According to certain embodiments, the electrode material angle 508 can be the angular coverage of the electrode material 502 at a window 108 and/or the through hole 104 about the axis 106. In one example, the electrode material angle is about 270 to 275 degrees. However, other electrode material angles 508 are also contemplated herein.

The term "communicate" as used herein means recording signals in or around the nerve and/or stimulating the nerve with externally produced signals.

The design presented herein has continuous carbon graphite contacts, fewer wires, and complete circumferential coverage improving peripheral nerve recording and stimulation functionality. From a three-dimensional (3D) computer aided design (CAD) model to realized electrode, the process has become entirely customizable and relatively quickly executed. Identifying carbon graphite as an alternative contact material has significantly reduced the cost and time of making a single electrode. The focus now is utilizing in silico data to direct the geometric optimization of contact spatial organization. Using a three-dimensional printing approach can allow for scalability to larger diameter nerves and specialized contact numbers that fit the desired research aim. The C-cuff assembly 102 designs discussed herein improve upon the surgical implantation process while functioning at or above the standard for cuff electrodes in vivo.

The cuff assembly 100 discussed herein is implemented to further address limitations seen in prior electrode cuff designs. The design for the cuff assemblies 102, and associated components, presented herein is a scalable, durable, and provide a stable structure that offers complete circumferential insulation through at least the combination of the cuff 102 and the I-beam sliding closure 110.

In one method of manufacturing contemplated herein, many components of the cuff assembly 100 can be 3D Printed. For example, the cuff base design and modifications are modeled in a CAD software for implantation optimization and experimental aim. The cuffs 102, regardless of inner diameter, can be designed in a C-shaped cylinder to cover approximately 80 percent of the nerve circumference and have a wall thickness 306 of about 500 μm (FIG. 3). The contact face or inset 114 has an inset depth 308 of about 250 μm from the inner diameter, central to the wall thickness 306. This inset 114 is open to the back side of the cuff 102, creating windows 108 to precisely define the contact surface and wire locations. Window covers 106 can be added into the design at the ends of the windows 108 on the back-side of the cuff 102 that can assist with wire placement during the assembly process. The base design can also be capable of scaling inner diameter ("ID"), contact number, contact width, contact pitch, and contact edge-to-end distance to optimize the geometries of the cuff 102 and/or cuff assemblies 100.

One aspect of this disclosure implements a 3D printed sliding closure 110 design. The sliding closure 110 can span the length of the cuff 102, with the stopper 104 at one end of the cuff 102 to prevent slide-through during implantation. The grounding well 112 at the top of the sliding closure 110 serves as an optional grounding well point at an isopotential line. The inner surface of the sliding closure 110 can overlap and sit flush with the cuff 102 to insulate the remaining 20 percent of the nerve circumference (see overlap 304 in FIG. 3).

In one aspect of this disclosure, 3D generated cuffs 102 and I-beam shaped sliding closures 110 can be exported from CAD software, such as, for example, as .STL files, among other file formats, and imported into the 3D printer software, including, for example, Preform 3.2.2 from Formlabs Inc., among others. Such 3D printing can occur at a 30 degree angle and with the cuff opening 202 upward so as to allow for proper media drainage during printing. In one embodiment, cuffs 102 were printed on a SLA 3D printer using clear photopolymer resin and rinsed in isopropyl alcohol upon print completion. All excess media was removed before curing in a heated UV cure chamber at 60 degrees Celsius (C.) for 15-20 minutes.

To assemble a functional cuff assembly 100, the shell or cuff 102 can first be placed on a hypodermic needle, and the contact surface windows 108 can be masked with silicone from the inner surface to an edge of inset 114 edge. Wires 504 are added through the window covers 106 and pulled taught after the windows 108 are filled with an electrode material 502 such as carbon black doped KrazyGlue© paste. The windows 108 are filled flush to the back surface of the cuff 102 and air dried. The contacts and wires 504 are insulated on the back side of the cuff 102 with print media and UV cured. Assembled cuffs are electrochemically coated with a poly(3,4-ethylenedioxythiophene):poly(4-styrenesulfonic acid) (PE-DOT:PSS) solution and stored for experimental use.

One aspect of this disclosure considers surgical implantation and testing. More specifically, the impedance of the cuff assemblies 102 is tested before and after experimentation to ensure safety and validate the robustness of the structure. Cuffs assemblies 100 are implanted to validate the spatial fit in the region of interest with the target nerve. After successful implantation of the cuff assemblies 100, data is collected to test the ability of the structure to record peripheral nerve compound action potentials. A recruitment curve is also collected to test the ability of the cuff assembly 100 to stimulate peripheral nerve activity in acute studies.

Figure 6A:
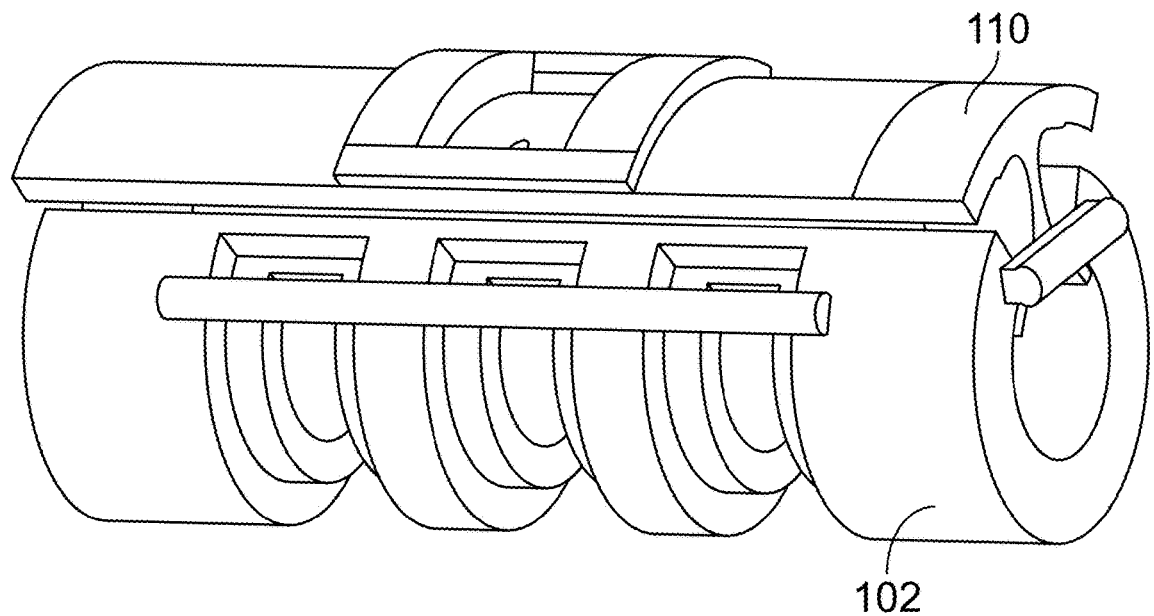
FIGS. 6a-6b are elevated perspective views of alternative embodiments of a cuff assembly that include additional electrode contact windows.
Figure 6B:
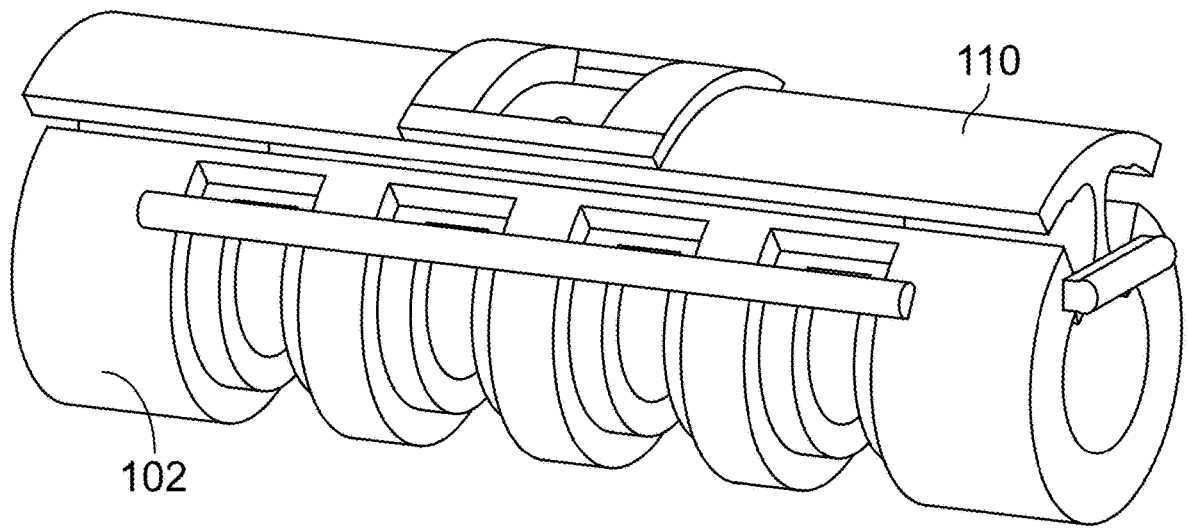

The cuff assemblies 100 discussed herein have been successfully printed with varying geometries as bipolar (FIG. 1), tripolar (FIG. 6a), and tetrapolar versions (FIG. 6b). In one embodiment of this disclosure, the inner diameter of the through hole 104 may be as small as 650 μm. However, the standard geometry for a rat sciatic model is a 1.3 mm through hole 104 inner diameter, 0.5 mm contact width, 1 mm pitch, and a 1.5 mm end distance. The sliding closure 110 can function so as to secure the cuff assembly 102 around the nerve and provide total structural insulation around the nerve.

In one aspect of this disclosure, the assembled cuff assemblies 102 discussed herein are reproducibly and successfully implanted on the tibial nerve of rats in acute experiments. The sliding closure 110 can fit precisely within the cuff opening 202 to offer a physical barrier that can keep the nerve in place without additional sutures. Compared to previous hinge closures, such cuff assembly 100 design further improves upon the time needed for implantation with less cable management and moving structure to work with.

Regarding the electrical functionality, the in vivo impedance of the device discussed in this disclosure is within safe and functional ranges and minimally changes before and after experiments. The electrodes 504 of the cuff assemblies 100 were able to repeatedly record (FIG. 12) and stimulate (FIG. 13) acute neural activity on the target nerve.

Compared to prior art designs, the cuff assembly 102 discussed herein provides for thinner walls 105, optimizes the spatial availability at the implantation site, and provides an improved opportunity to implant multiple cuff assemblies 102, as needed. By designing a smaller opening 202 in the cuff 102, the amount of coverage provided by the cuff 102 alone can be improved from around 50%, as in the prior art, to around 80%. Further, the 60-degree radial opening 202 of the cuff 102 can allow for sufficient space for the nerve to fit into the cuff 102 without causing structural damage to the nerve. This change was justified by the anticlastic nature of the nerve while under tension. During implantation, the nerve is only stretched enough to fit inside the radial opening 202 of the cuff 102. Once inside the cuff 102, the nerve can return to its original diameter and fit securely inside the cuff 102, thereby reducing the likelihood of cuff 102 dislocation before the sliding closure 110 is secured. This improved cuff 102 coverage not only can reduce current leakage, but also can increases the available contact surface area around the nerve. The C-shaped design of the cuff 102 can also provide a contact circumference coverage of over 75%, which is relatively significant when compared to the approximately 50% coverage typically provided by other existing designs.

Additionally, the windows 108, adapted from the cuff 102, may no longer serve as an attempt to prevent contact fouling, but rather provide a way to efficiently direct current. Moreover, instead of providing a surface edge for stainless-steel plates, as found in the prior art, the windows 108 of the cuff 102 can act as wells for the contact paste or electrode material 502, and can allow for the wires 504 to be directly embedded. This design and associated process thereby consequently can accommodate the creation of a larger contact surface area on the back of the cuff 102, particularly when compared to smaller, well-defined surface areas at the contact-tissue interface. The result can be a current concentration gradient that funnels the current density toward the inside of the cuff 102, thereby improving the current concentration at the interface as well as provide a more stable and electrically favorable environment for when using the cuff assembly 100.

Prior cuff designs also often have the added concern that sutures could come lose during use of the cuffs, and slip down around the nerve, thereby possibly causing nerve damage. Thus, as an improvement over prior designs, the sliding closure 110 of the cuff assemblies 100 discussed herein provides a structural closure that solves not only issues associated with current leakage, but also can eliminate such concerns regarding suture slippage. Moreover, the sliding closure 110 presented herein does not need sutures to be held in place, as the sliding closure 110 is friction-held within the cuff 102 and sits flush against both the inner surface and the radial opening 202 of the cuff 102. Further, the sliding closure 110 and cuff 102 are configured such that the overlaps 304 of the sliding closure 110 overlaps and engage an inner circumference of the cuff 102 in a manner that provides relatively substantial avoidance of current leakage and about 388 degrees of coverage around the nerve.

The use of CAD software and 3D printing can also make it possible to make relatively rapid modifications and improvements to the designs of both cuff 102 and sliding closure 110, as needed. The present disclosure allows the user to create custom spatial changes in contact geometry as well as changes to contact number, amplifying the number of test variables capable of optimization. Three-dimensional printing also provides an accurate way to repeatedly reproduce successful designs in bulk. This means that blank cuffs 102 and sliding closures 110 can be ready for manufacturing and the user can avoid having to wait for a single part to print each time a new electrode is needed. The teachings of this disclosure also provide cuff assemblies 102 that are customizable, including having non-standard dimensions and designs, and in which the user can save both time and money by printing and manufacturing in the lab. By also producing the contacts as discussed herein, the cost and time it may take to make a single electrode can be optimized. For example, the volume of functional electrodes produced may only be limited by the time it takes to make the electrodes by hand.

In another aspect, this disclosure contemplates the use of the processes and materials for forming electrical contacts described herein, or adaptations thereof, for use in a wide variety of other applications beyond those described in the cuff architectures described herein. For example, it is understood that a wide variety of medical devices in addition to the cuff assemblies 100 described herein include electrodes and contacts intended to interface with neural cells and/or tissues. For example, in one embodiment, this disclosure contemplates fabrication of such electrodes and contacts using one or more of the process steps and one or more of the materials disclosed herein, and summarized as follows: (i) affixing an electrically conducting wire to a retaining body with an electrode precursor material as described herein, which sets or dries to retain the conducting wire in a desired position relative to the retaining body, (ii) applying an electrically insulating coating over an exterior portion of the electrode material and the wire, and (iii) applying an electrochemical coating as described herein over a neural interface surface of the electrode material to form a contact. In certain embodiments, the electrode material comprises a binder or adhesive and a carbon filler, such as carbon graphite. Further, in certain embodiments, the electrochemical coating comprises an ICP and finely divided electrically conductive particles, such as carbon black, nano-carbon black, carbon nanotubes, carbon nanoribbons, graphene, and combinations thereof, entrained therein. In a particular exemplary embodiment, the carbon filler comprises carbon graphite and the electrochemical coating is formed by electroplating an ICP solution comprising poly(3,4-ethylenedi-oxythiophene):poly(4-styrenesulfonic acid) (PEDOT:PSS) with finely divided conductive particles, such as carbon-black (CB), entrained therein via electrodeposition.

In another embodiment, a method for forming an interface coating on a nerve-facing bioelectric surface of an electrode for delivering an electrical impulse to a nerve in an animal includes providing an aqueous solution or suspension comprising 3,4-ethylenedioxy-thiophene (EDOT), poly(4-styrenesulfonic acid) (PSS) and a carbon nanomaterial, submerging in the aqueous solution or suspension an electrode configured for delivering an electrical impulse to a nerve in an animal, wherein a nerve-facing bioelectric surface of the electrode is in contact with the aqueous solution or suspension and forming an interface coating on the nerve-facing bioelectric surface by electrodeposition. The interface coating thus formed comprises electroplated poly(3,4 ethylene-dioxythiophene):poly(4-styrenesulfonic acid) with a dispersed carbon nanomaterial filler. The carbon nanomaterial can be, for example, carbon black. If some, but not all, surfaces of the electrode are to be covered with an interface coating, one or more surface of the electrode material on which the interface coating is not desired, can be covered before the electrode is submerged.

A person of ordinary skill in the art will appreciate that the concentrations of the respective ingredients can be varied within certain limits without departing from the disclosure.

The ingredients can, for example, be dissolved or suspended in an aqueous solution of an alcohol and water, such as a 20% (v/v) ethanol/double-deionized $H_2O$ ($EtOH/_{dd}H_2O$) solution. In one embodiment, the aqueous solution or suspension comprises from about 0.5 to about 20 mg/mL EDOT, from about 4 to about 10 mg/mL PSS and from about 0.5 to about 4 mg/mL carbon black. In another embodiment, the aqueous solution or suspension comprises from about 0.5 to about 10 mg/mL EDOT, from about 4 to about 10 mg/mL PSS and from about 0.5 to about 4 mg/mL carbon black.

In one embodiment, electrodeposition is achieved potentiostatically at a DC voltage of from about +0.5 to about +1.5 for a time period of from about 15 minutes to about 25 minutes. In another embodiment, electrodeposition is achieved under galvanostatic conditions at from about +150 to about +250 μA for a time period of from about 3 minutes to about 7 minutes. The electrodeposition process can be continued until the interface coating has an average thickness of from about 100 μm to about 1 mm, or any other desired thickness.

The bioelectric surface on which an interface coating is applied can be in some embodiments a bioelectric surface of an implantable electrode, such as an electrode of an implantable cuff, or can be configured for external contact with a skin surface for delivery of an electrical signal to a nerve through the skin.

In some embodiments, the nerve-facing bioelectric surface of the electrode upon which the interface coating is formed is a porous surface, such as, for example, and without limitation, a porous surface composed of an adhesive and a carbon filler material. The carbon filler material can be, for example, a carbon graphite material. The adhesive can be, for example, a cyanoacrylate adhesive. It is not intended, however, that the present disclosure be limited to these examples.

In another embodiment, there is provided an electrode for delivering an electrical impulse to a nerve in an animal, the electrode including a bioelectric surface configured to face a nerve when the electrode is positioned for use and an interface coating on the bioelectric surface, wherein the interface coating comprises electroplated poly(3,4 ethylenedioxythiophene):poly(4-styrenesulfonic acid) with a dispersed carbon nanomaterial filler. Such an electrode can be made in accordance with the method embodiments described herein.

In another embodiment of the disclosure, there is provided a conductive material comprising poly(3,4 ethylenedioxythiophene):poly(4-styrenesulfonic acid) (PEDOT: PSS) with a dispersed carbon nanomaterial filler entrained therein, wherein the carbon nanomaterial filler is randomly dispersed within the PEDOT:PSS. The carbon nanomaterial filler of this material can be, for example and without limitation, carbon black.

In yet another embodiment, there is provided a conductive material comprising first and second layers, wherein the first layer comprises a porous surface in contact with the second layer, and wherein the second layer comprises poly(3,4 ethylenedioxythiophene):poly(4-styrenesulfonic acid) with a dispersed carbon nanomaterial filler. The carbon nanomaterial filler of this material also can be, for example and without limitation, carbon black. In some embodiments, the porous surface is composed of an adhesive, such as, for example, and without limitation, a cyanoacrylate adhesive, and a carbon filler material, such as, for example, and without limitation, a carbon graphite material.

Another aspect of the subject disclosure relates to the use of a continuous sinusoidal Low Frequency Alternating Current (LFAC) waveform, such as, for example, a frequency in the range of 0.1 hertz (Hz) to 100 Hz, to produce generally asynchronous nerve activity. Moreover, according to certain embodiments, LFAC can involve low level alternating current (AC), such as, for example, current less than 1 milliamp (mA) at low frequencies, such as, for example, at frequencies less than 10 Hz. The inventors have surprisingly discovered that direct nerve stimulation via use of an electrical sinusoidal LFAC waveform can result in the blocking ($LFAC_b$) of action potential conduction, and that an increase in LFAC frequency and/or amplitude can translate into nerve activation (LFACa). Moreover, the inventors have discovered that with increased LFAC amplitudes and frequency, a transition occurs between nerve blockage and nerve activation, which can be referred to as the block or block-activation window (e.g., $LFAC_b/LFAC_a$ window). Further, the inventors have surprisingly discovered that $LFAC_b$ is frequency independent, while $LFAC_a$ thresholds decrease with increasing frequency, which results in an $LFAC_b/LFAC_a$ window. Thus, frequency and amplitude settings can determine whether LFAC activates or blocks nerve fibers. Further, studies have indicated that the threshold for block is generally lower than the frequencies for activation (e.g., less than 5 Hz), while activation dominates at higher frequencies. Identification of the transition to activation can provide a parameter for characterizing LFAC block, as such a transition can represent the upper bound of the $LFAC_b/LFAC_a$ window. In at least certain circumstances, effective neural block for $LFAC_b$ can occur at frequencies that are below 4 Hz. Additionally, unlike ES that utilizes rectangular pulse waveforms, $LFAC_a$ appears to be orderly, with smaller nerve fibers having lower thresholds than larger nerve fibers. Thus, $LFAC_a$ can provide stimulation in which smaller, non-fatiguing nerve fibers are activated before larger, fast fatiguing nerve fibers. Accordingly, utilization of LFAC, as disclosed herein, can achieve activation of nerve fibers in the order of natural fiber recruitment.

Accordingly, LFAC can address the issues associated with standard ES since there is evidence that it not only is LFAC capable of blocking nerve fibers, but with increasing current levels, block transitions to activation. At the activation levels LFAC can activate nerve fibers in the small to large caliber order. Additionally, indications are that LFAC could overcome the fatigue and controllability problem inherent in standard ES for muscle activation.

Figure 14:
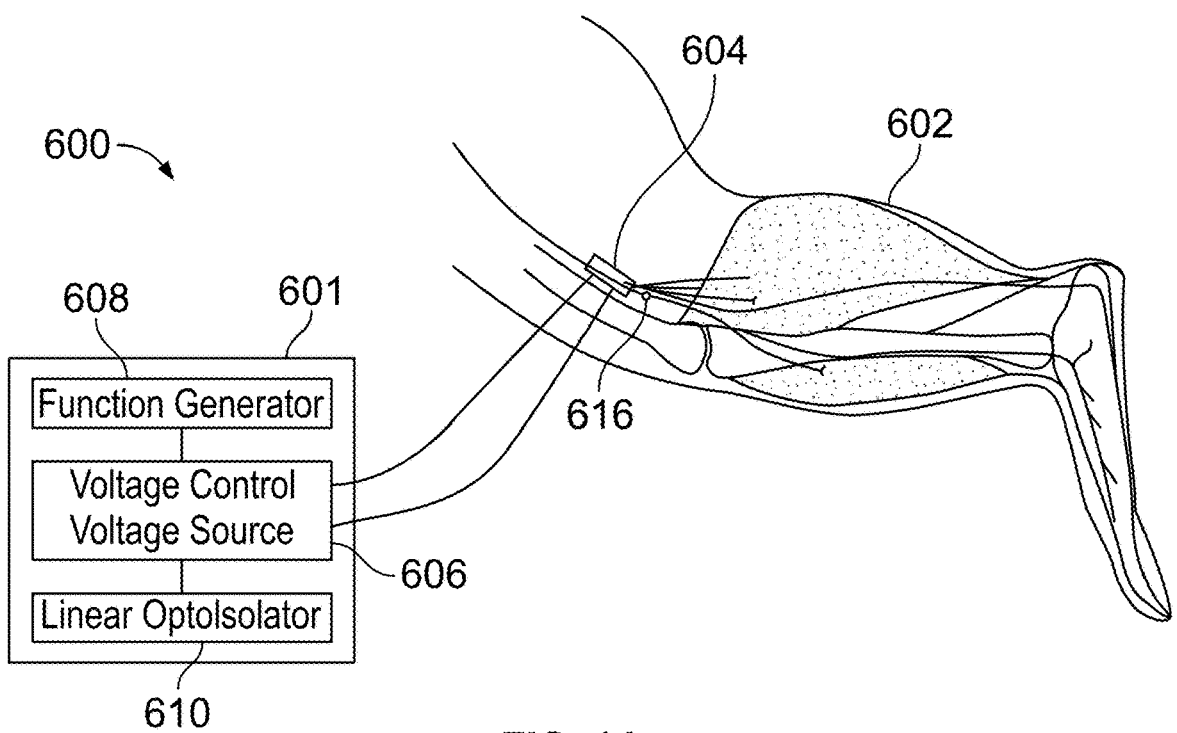
FIG. 14 illustrates an exemplary Low Frequency Alternating Current (LFAC) system according to an illustrated embodiment of the present application.

FIG. 14 illustrates an exemplary LFAC system 600 implanted in a portion of a limb 602 of a subject mammalian patient. The illustrated LFAC system 600 can include a cuff assembly 604 that is electrically coupled to a control system 601 that is configured to deliver electrical sinusoidal LFAC waveforms to the bipolar cuff assembly 604. According to certain embodiments, the control system 601, which is coupled to an electrical power source, can include a current source 606, function generator 608, and/or a linear optolsolator 610. The current source 606, which, according to certain embodiments, can be a voltage controlled voltage source, can be coupled to the cuff assembly 604 and receive the sinusoidal waveform at a selected frequency(ies) from the function generator 608. The cuff assembly 604 can be similar to any of the various cuff assembly 100 configurations that are discussed above. In the illustrated exemplary embodiment, the LFAC waveform can be delivered to electrodes 612, 614 (FIG. 15) of the cuff assembly 604 by the optolsolator 610 followed by the isolated voltage controlled current source 606. Further, the current of the voltage controlled voltage source can be monitored to enable current control. According to certain embodiments, both voltage and current can be monitored while LFAC is delivered to the bipolar pair of electrodes 612, 614.

The cuff assembly 604 can be constructed to be positioned within and/or around a nerve 616. Further, the cuff assembly 604 can be adapted to include two or more electrodes that are electrically coupled to the nerve 616 via an electrode interface, such as, for example, a conductive polymeric material contact surface that can contact the nerve 616 when the cuff assembly 604 is positioned within and/or about the nerve 616. Further, according to certain embodiments, the cuff assembly 604 can be part of an implantable device that can be capable of continuous monitoring of the neural and/or electrochemical interface(s) between the cuff assembly 604 and the tissue and/or nerve fibers of an individual in which the device is implanted.

Figure 15:
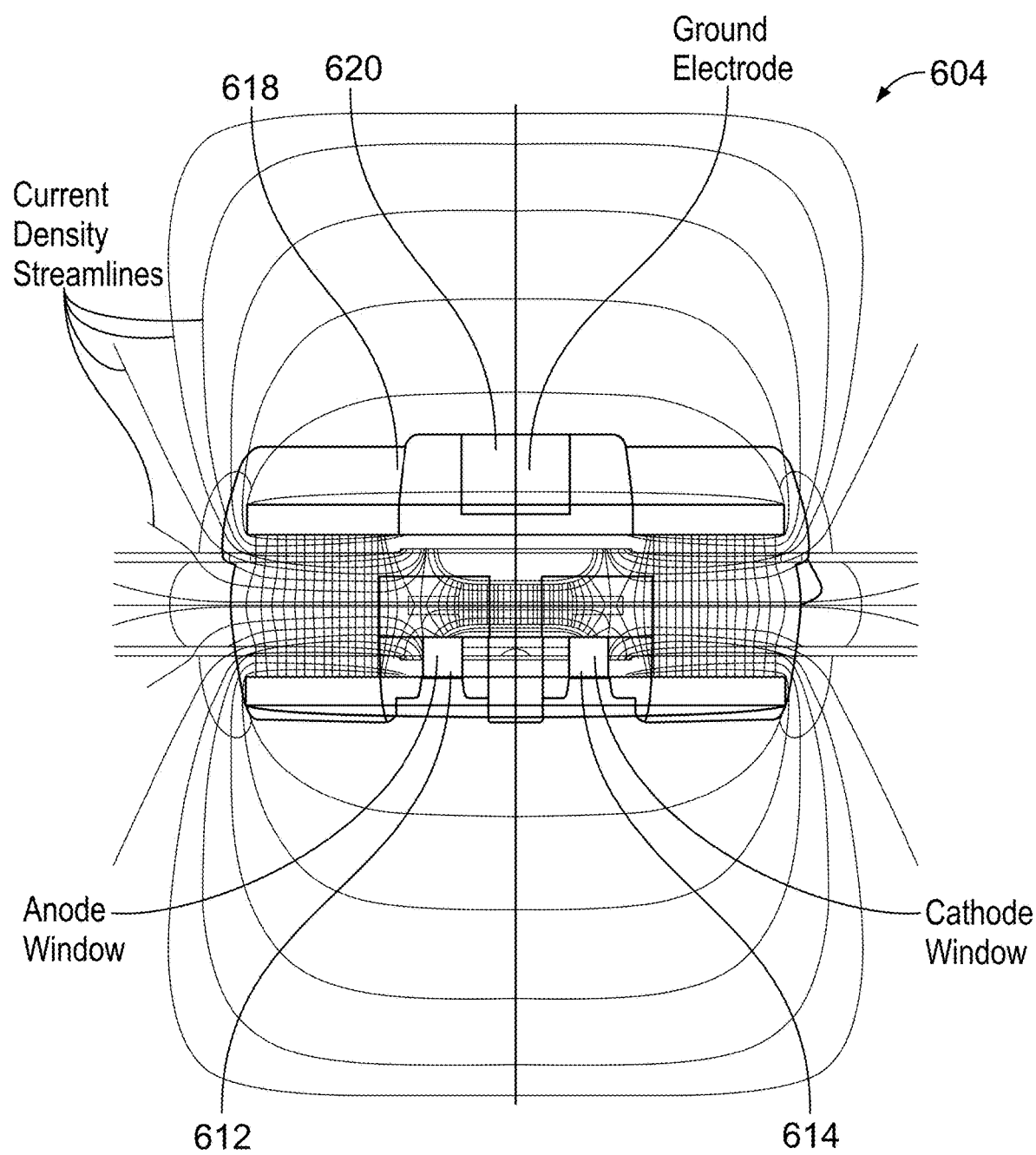
FIG. 15 illustrates simulation of an exemplary bipolar cuff assembly used to deliver LFAC stimulation predicting the current density and potential distributions produced as current is passed through the electrode interfaces of the electrodes of the cuff assembly.

FIG. 2 illustrates an exemplary cuff assembly 604 used to deliver LFAC, as well as the current density and potential distributions produced as current is passed through the electrode interfaces of a plurality of electrodes 612, 614. As seen, the cuff assembly 604 includes a body portion 618, which, in the illustrated embodiment, is configured to be positioned around a nerve 616. However, according to other embodiments, the cuff assembly 604 can be a cuff electrode that is implanted within the nerve. Additionally, coupled to the body portion 618 of the exemplary cuff assembly 604 is a plurality of electrodes 612, 614. Moreover, in the illustrated embodiments, the cuff assembly 604 is a bipolar cuff assembly that includes a first electrode 612, such as, for example, an anode electrode, and a second electrode 614, such as, for example, a cathode electrode. While FIG. 15 illustrates a bipolar cuff assembly 604, according to other embodiments, the cuff assembly 604 can be tripolar or tetrapolar. Additionally, the cuff assembly 604 can include a ground electrode 620. The electrodes 612, 614 can be configured to deliver and sustain relatively continuous low frequency currents to the patient.

The LFAC technique disclosed herein can use relatively low level electric current, such as, for example, current below 1 milliamp (mA) and at frequencies that can be less than 10 hertz (Hz). Accordingly, the electrode interface for the cuff assembly 604 can be configured to deliver current to the nerve 616 without exceeding the point at which the potential dropped across the electrode interface is greater than the point where water can split. By preventing the splitting of water, the associated formation of hydronium or hydroxide ions through hydrolysis, which can radically shift the pH of surrounding environment and be toxic to tissue, can be avoided. Thus, according to certain embodiments, the system 600 can be configured to monitor the potential dropped across the electrode interface so as to prevent exceeding the cell potential, and thereby at least attempt causing a hydrolysis of water, which can also be referred to as the water window. Additionally, the possibility of chemically injuring tissue via use of the system 600 can at least be reduced by keeping the electrochemical cell potential to less than the electrolysis potential, keeping the electrode interface with its linear operating range, alternating the current to reverse the injected charges, and maintaining a zero charge balance.

Figure 16A:
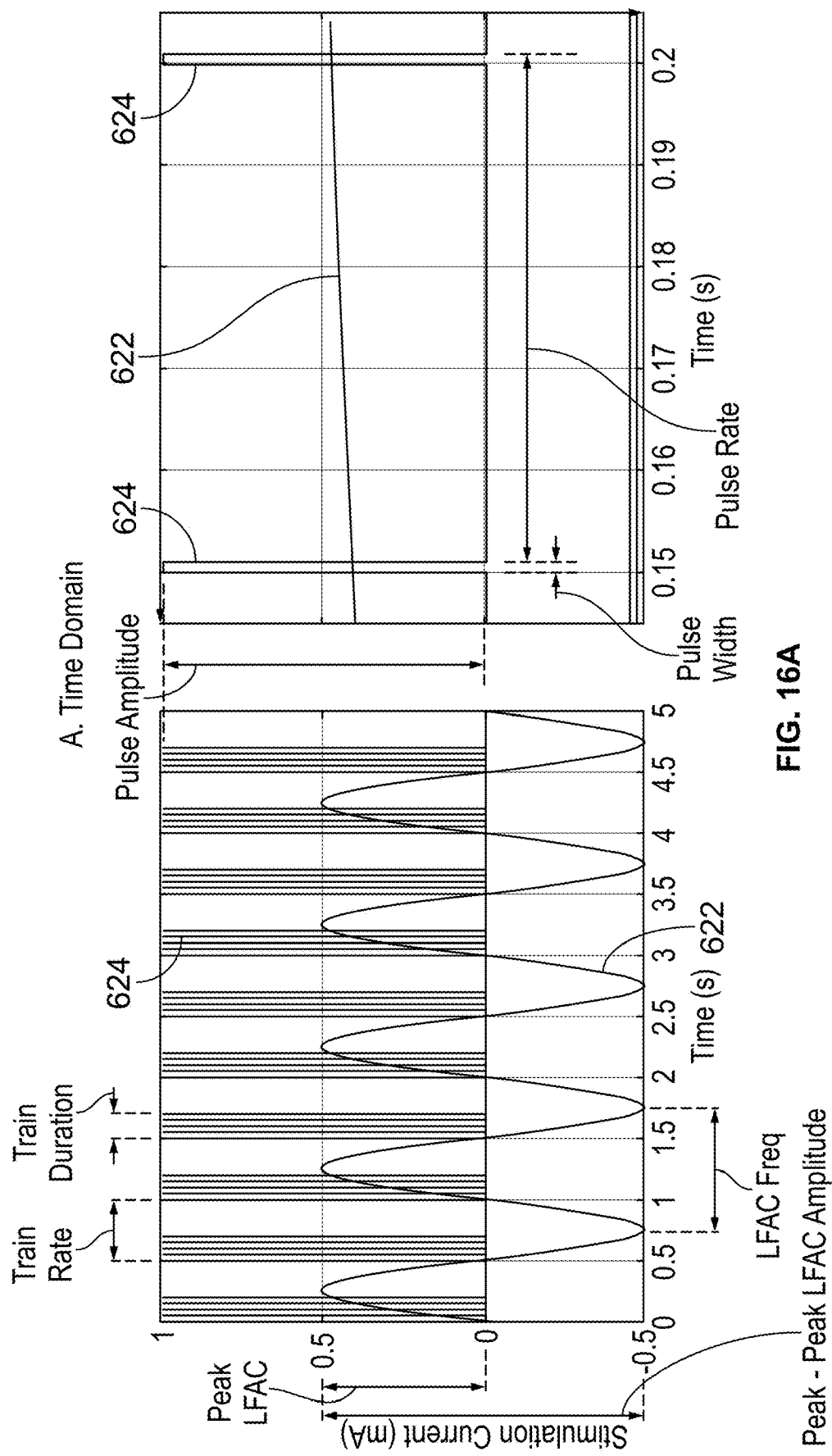
FIGS. 16A and 16B illustrate, in the time and frequency domains, respectively, differences between delivery of pulse stimulation and LFAC stimulation, and in which a 1 milliamp (mA) LFAC sinusoidal waveform is displayed in contrast to 1 mA standard pulse waveform used to elicit trains of neural activity.
Figure 16B:
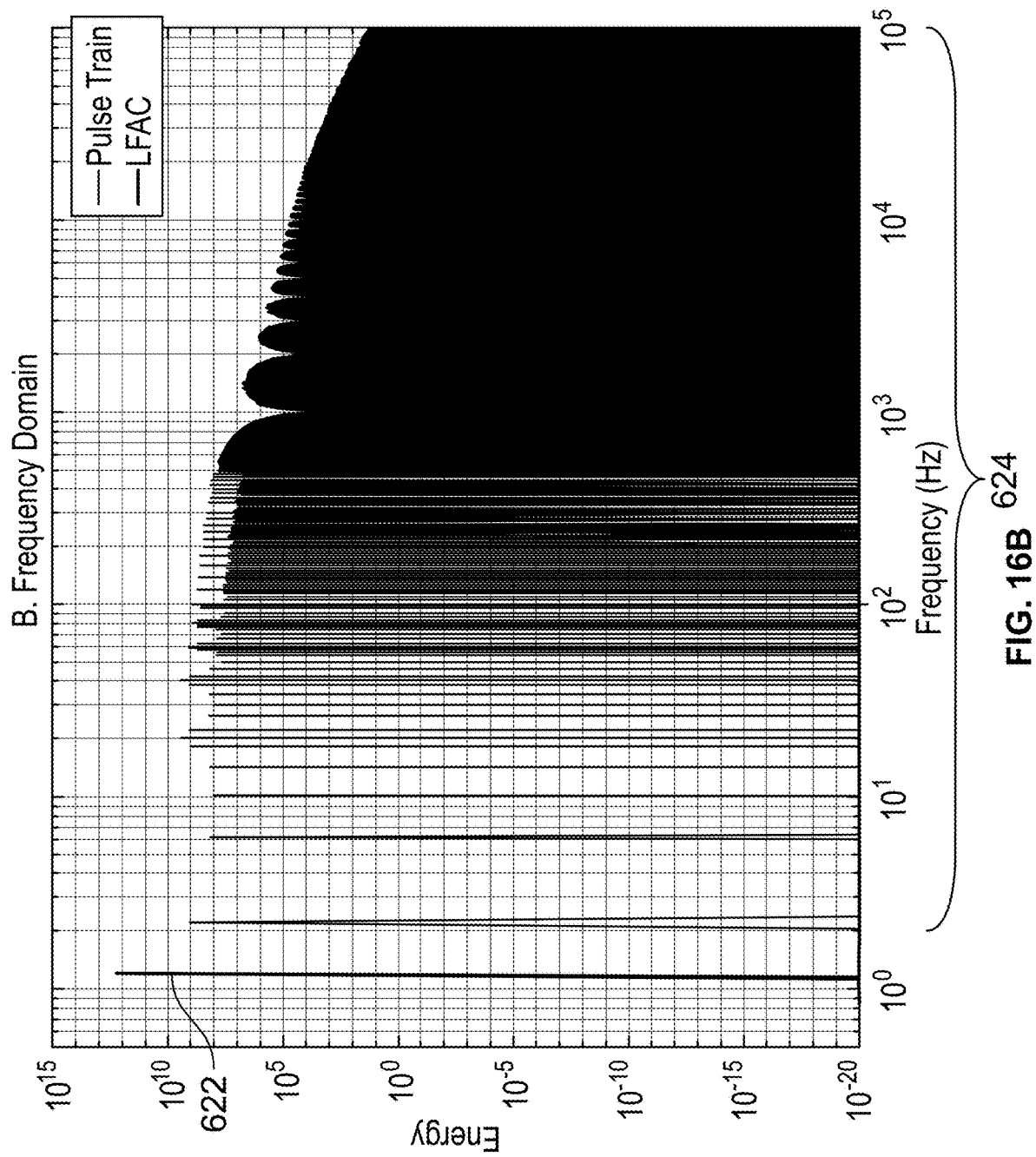

The LFAC waveform can be applied to the nerve fascicle via intrafascicular bipolar electrodes or bipolar cuff electrodes 612, 614. Unlike traditional rectangular or trapezoidal pulse stimulation, the sinusoidal LFAC waveform 622, as illustrated, for example, in FIGS. 16A and 16B, is a zero mean, pure-tone sinusoid that is defined by a magnitude and frequency. In contrast, the standard pulse trains of the pulse waveform 624 is defined by the pulse amplitude, pulse width, pulse rate, pulse train duration and pulse train rate. Spectrally, these two waveforms 622, 624 represent canonical opposites. Moreover, in the frequency domain, the LFAC waveform 622 is a pure tone whose spectral density occupies a single frequency, while the pulse trains of the pulse waveform 624 can be approximated by a patterned train of impulses. Further, as seen in FIG. 16B, the LFAC sinusoid waveform 622 is broadly defined in the time domain, but is relatively extremely narrow in the frequency domain. In contrast, the pulse waveform 624 in the pulse trains can be approximated as impulses, and thus are relatively extremely narrow in the time domain but are broadly defined in the frequency domain.

Using a system 600 such as, for example, that shown in FIG. 14, the application of a relatively low frequency (1-100 Hz) pure tone sinusoidal electrical current waveform through extra or intrafascicular peripheral nerve electrodes 612, 614 has shown to produce slowing or complete block of conducting action potentials in in-vivo and ex-vivo experiments in mammalian vagus and sciatic nerves. While exploring the boundaries of $LFAC_b$, the inventors have discovered that the LFAC waveform can produce nerve fiber activation at larger current amplitudes and higher frequencies. Moreover, as the current amplitude is increased, the degree of nerve block can be increased until a threshold is reached at which nerve activation can occur. Similarly, the $LFAC_b/LFAC_a$ window, which is the threshold frequency(ies) between nerve blockage and nerve activation, has been discovered to be a function of the frequency of the sinusoidal wave form. For example, according to certain applications, closure of the block-activation ($LFAC_b/LFAC_a$) window can be seen at around 10 Hz, among other frequencies. Further, utilizing LFAC, nerve blockage can be invariant of frequency, while the nerve activation threshold can decrease with increasing sinusoidal frequency. Thus the $LFAC_b/LFAC_a$ window can narrow and close with increasing LFAC frequency. Additionally, in at least some embodiments, increasing current beyond the $LFAC_b$ threshold can result in nerve activation near the anode-cathode transition.

According to certain embodiments, the current levels to achieve nerve block can, at a frequency of around 1 Hz, be in the tens to hundreds of a micro amp (μA), while nerve activation can be achieved with about ten times more current. At higher frequencies, the activation threshold can, in at least certain situations, be decreased from approximately 1 mA to approximately hundreds of μA, and thus, for example, from about 1 mA to less than 500 μA. In such cases, stimulation currents can still be within the water window of the electrodes 612, 614. Further, since the sinusoidal waveform of LFAC is zero mean and symmetrical, an injected current can be recovered, and no, or minimal, net charge can be injected to the tissue, such that using LFAC for nerve blockage and/or activation can be relatively safe for long term use.

Additionally, in-silico modeling of the phenomenon consisting of an active nerve fiber model coupled to a finite element model of a nerve bundle and a volume conductor has also indicated that LFAC block ($LFAC_b$) is frequency independent, while LFAC activation ($LFAC_a$) is not only frequency dependent, but also recruits fibers within their phenotype in a size-wise fashion. Such features suggest closed-state Na+ channel inactivation as a potential nerve blockage mechanism. Further, nerve activation can become dominant at higher frequencies as the change in transmembrane potential with time begins to favor the Na+ channel activation state variable. Such results can indicate that LFAC$_b$/LFAC$_a$ window can be tunable to not only fiber caliber, but also fiber phenotype (myelinated/unmyelinated) by taking advantage of the sinusoidal blocking waveform frequency/amplitude, as well as based on the selection or design of the electrode contact size, the distance between the contacts (also referred to as pitch), and location (intrafascicular/extrafascicular), and/or the fiber channel makeup/composition.

Such outcomes and observations can be applied to address a major limitation of prior electrical stimulation techniques used in motor rehabilitation, namely rapid fatigue in electrically stimulated muscle. Moreover, through use of LFAC, a nerve activation waveform and, in at least certain embodiments, an electrode configuration, can be used to achieve fatigue resistant muscle activation, and identify strategies to modulate and control force output. Moreover, LFAC can be used as a modality to deliver functional electrical stimulation to generate fatigue resistant tetanized muscle contractions.

The inventors of the subject disclosure have demonstrated LFAC block and activation in the autonomic nervous system where LFAC was used to block VNS targeting bradycardia, and to activate the Hering-Breuer (HB) reflex. Such demonstrations have provided an indication that LFAC is able to act on the smaller myelinated nerve fibers. Evidence from the HB reflex studies, as well as via in-silico models, have been determined to demonstrate that LFAC can produce small fiber activation prior to activation of large, fatigable fibers. Moreover, such studies have confirmed in-silico models indicating that, when using LFAC, smaller caliber fatigue resistant motor neurons can be activated before large caliber fast fatiguing fibers. These in-vivo experimental observations suggest that LFAC recruits motor nerves in a size-wise order.

According to certain embodiments, closed state Na+ channel inactivation can be utilized as a mechanism for LFAC block. In such situations, with increasing LFAC amplitude, a closed state block (under the cathode) can be attained that can be followed by fiber activation as the anode-cathode waveform crosses over from one half of the LFAC waveform to the other, followed by, at relatively very high currents, depolarization or anodal block. According to such embodiments, size-wise activation thresholds for different sized nerve fibers can be attained with increasing LFAC currents, and the frequency dependency of the nerve activation threshold. Again, the block threshold is largely frequency independent. Electrode geometry can play a role in the order of LFAC$_b$, while frequency of the LFAC waveform can play a role in LFAC$_a$. The independence of LFAC$_b$, and the dependency of LFAC$_a$, to waveform frequency suggests that the underlying mechanisms for LFAC$_b$ and LFAC$_a$ are not the same. It further suggests that LFAC$_b$ and LFAC$_a$ could be used in tandem or with pulse stimulation to shape the order of nerve fiber activation. The fiber caliber and type of tunability of LFAC$_b$ can fall out of the cable equation:

$$\lambda^2 \frac{\partial^2 V}{\partial x^2} = \tau \frac{\partial V}{\partial t} + V + R_m I_{ch}(x, t) \quad \text{(Eq. 1)}$$

where $R_m$ is membrane resistance, I is membrane current, $C_m$, is membrane capacitance, $\rho_m$ is the membrane resistivity, and $\varepsilon_m$ is the membrane permittivity, $$\lambda = \sqrt{\frac{R_m}{c}},$$

and $\tau = C_m R_m = \varepsilon_m \rho_m$, and which defines the axon's transmembrane potential (V) as a function space (x) and time (t). Changes in the spatial distribution of the membrane potential along the axon and in the temporal development of potential in time are intertwined. Critical factors are the length constant ($\lambda$), which defines how far the membrane potential carries along its length, and the time constant ($\tau$), which defines how quickly the membrane responds to changes in potential. For a given type of fiber (myelinated/unmyelinated) the length constant is proportional to the axon's radius. The length constant ($\lambda$) is approximately:

$$\lambda = 1200 d \sqrt{-\ln(g)} \quad \text{(Eq. 2)}$$

where d is the axon diameter and g is the axonal g-ratio (inner fiber diameter/outer fiber diameter). The time constant ($\tau$) however is independent of caliber since the increase in capacitance and decrease in resistance with increasing caliber offset each other. For myelinated fibers the time constant can be between 0.4 milliseconds (ms) to 1.2 ms, with a corner frequency between 132-400 Hz. The Green's function, akin to the spatial-temporal impulse response function, can provide an indication of how spatial and temporal factors combine to determine membrane potential. The membrane potential and its rate of development act upon the channel state variables of the nerve fiber. Thus adjusting the field to match the length constant can be used to tune the potential distribution to a match a particular nerve fiber caliber.

In certain applications of LFAC$_b$, action potentials can be initiated at one end of a nerve fiber, such as, for example, a myelinated nerve fiber, and an LFAC$_b$ electrical signal can be conducted towards a conditioning electrode. In such situations, an externally activated action potential conduction can be tracked to determine how LFAC that is delivered through the bipolar cuff assembly 604 can influence its conduction. LFAC$_b$ can characteristically occur under the cathode electrode 614 of the cuff assembly 604. Inspection of the Na+ channel (NaV1.7) gating variable has revealed that the Na+ channel is inactivated by the LFAC waveform without channel activation, a characteristic of closed state Na+ channel inactivation. Further, before nerve block is effected, there is a pronounced decrease in the action potential (AP) conduction velocity as it transits through the LFAC electrode 612, 614, and moreover the action potential slows as it approaches the electrode 612, 614 presenting the blocking (cathodic) current. Since the LFAC current is passed through a symmetrical bipolar pair of electrodes 612, 614, there are two phases of block per LFAC cycle, as the anode and cathode electrodes 612, 614 swap every half cycle. Using LFAC, block can continue with increasing amplitudes until the activation threshold is reached.

Figure 17:
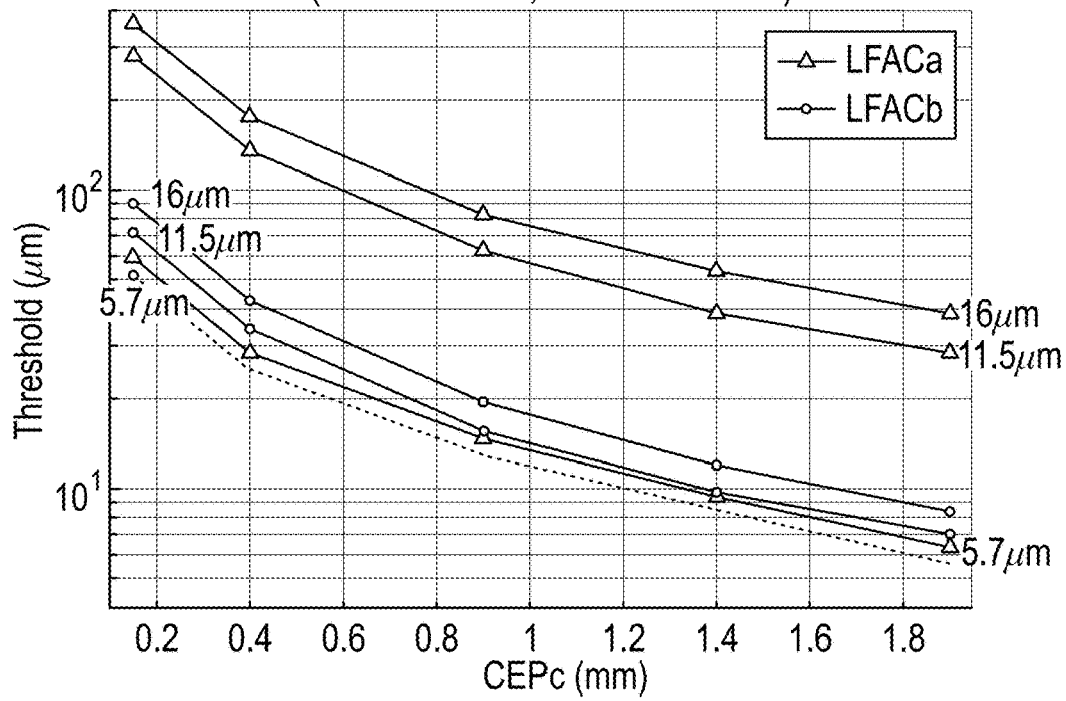
FIG. 17 illustrates data from an in-silico block/activation experiment performed using LFAC on a vagus nerve of a rat, and which depicts exemplary block and activation thresholds as a function of electrode contact pitch (top), and LFAC frequency (bottom) for 3 different nerve fiber calibers.
Figure 17:
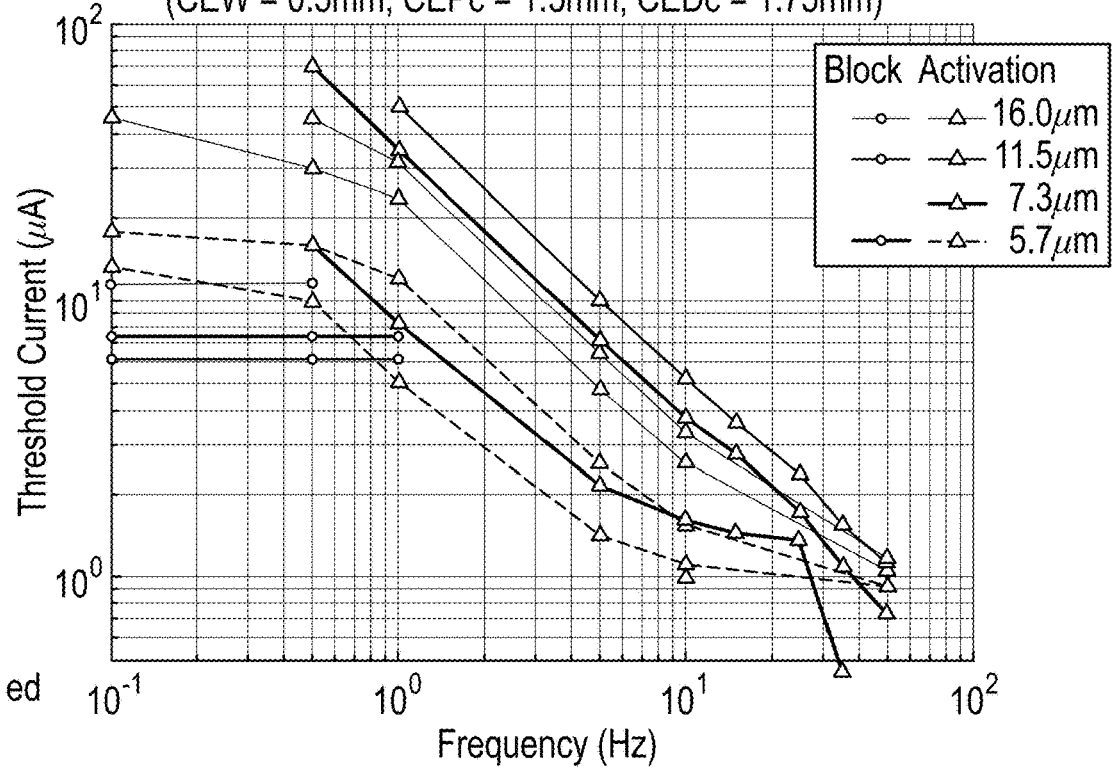

FIG. 4 shows a compiled set results showing block and activation thresholds from an in-silico block experiment performed on a rat vagus nerve. The predictions from the model are that nerve block is independent of LFAC frequency. Further, as seen, the lowest threshold does not correspond to the smallest or largest nerve fiber, suggesting tunability of nerve block with the geometry of the electrode(s) 612, 614. The exemplary threshold currents for block and activation shown in FIG. 17 demonstrate that the nerve block threshold attained using LFAC is generally less than the activation threshold. Further, the minimum current needed for nerve activation using LFAC is taken as the activation threshold. The summary curves shown in FIG. 17 also further demonstrate that the current threshold for nerve block using the LFAC waveform is frequency independent, while nerve activation is frequency dependent, and the order of nerve activation using LFAC is size-wise. As small caliber fibers have lower thresholds than large caliber fibers, and the activation threshold decreases with increasing frequency in the LFAC waveform, $LFAC_b$ is frequency limited by activation, which can result in a finite block-activation ($LFAC_b/LFAC_a$) window.

An activation experiment involving an in-silico model in which an LFAC waveform was used to directly evoke nerve fiber activation resulted in the discovery that, under such a procedure, two types of activation can occur, namely unitary activation and burst activation. Unitary activation can occur at the crossover point of the LFAC waveform. Thus, typically, there are two unitary activations per LFAC waveform cycle. Further, action potentials produced by unitary activation can propagate in an orthodromically direction and an antidromically direction, and can originate under the electrode 612, 614 that becomes the cathode during the anode-cathode crossover. Burst activation can generate multiple action potentials, which typically propagate in one direction each LFAC waveform half cycle. Burst activation typically originates under the virtual cathode, but is blocked from propagating in one direction by the anode, resulting in unidirectional volleys. Further, with unitary activation, the timing of activation can follow just after the crossover of the electrode 612, 614, while with burst activation the crossover is from the cathode-anode. The crossover point can be the time point where the change in voltage as a function of time (dv/dt) is at its highest, suggesting that it is the transition where closed channel inactivation of the Na+ channel is overwhelmed by a time constant of the activation state variable (m).

Figure 18:
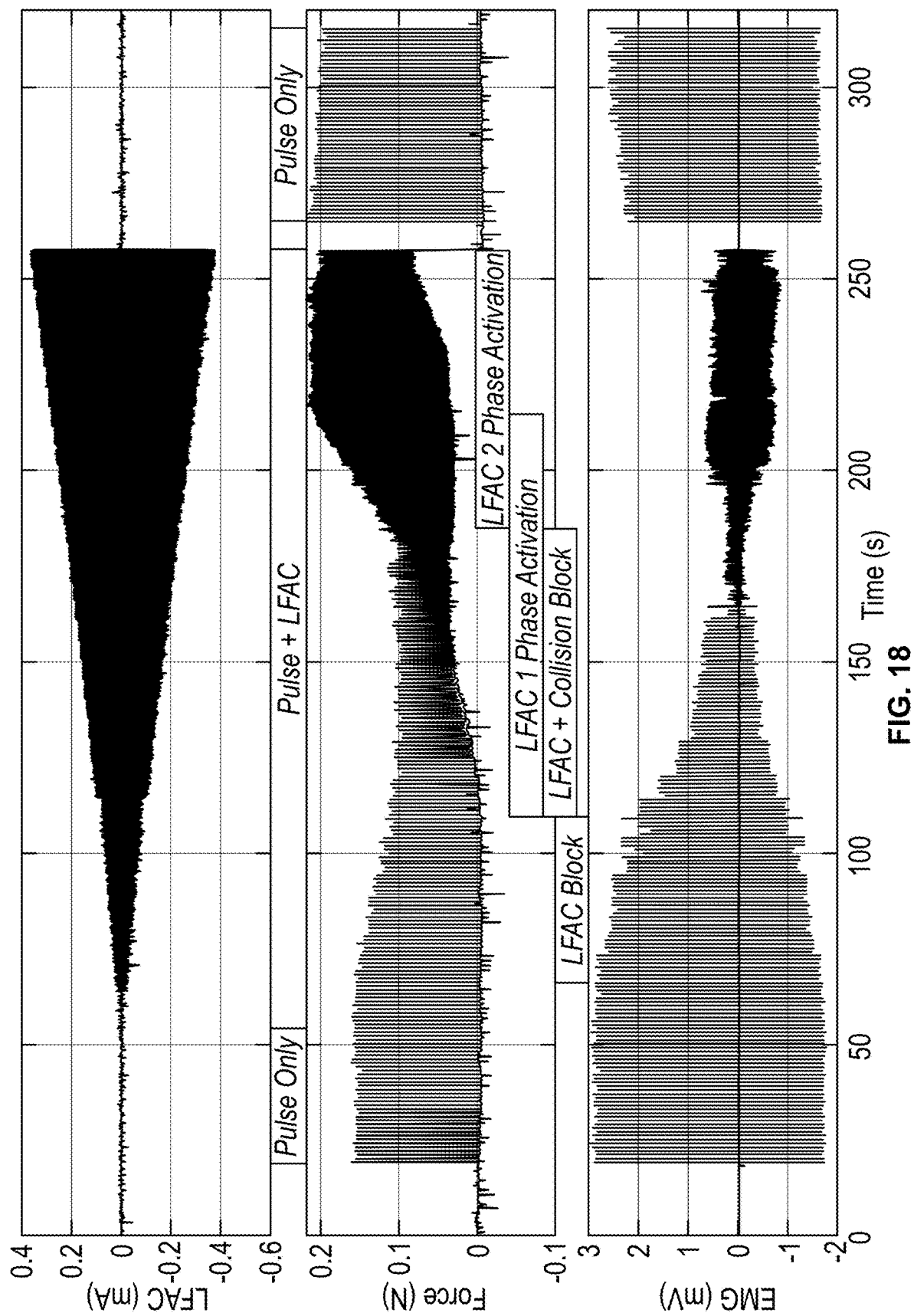
FIG. 18 illustrates data associated with in-vivo LFAC block-activation experiments in the sciatic nerve of an anaesthetized rat model, and in which muscle force and electromyography were used as biomarkers.

FIG. 5 illustrates data associated with in-vivo experimentation of embodiments of the subject disclosure, and more specifically in-vivo LFAC block experiments using a sciatic nerve of an anaesthetized rat mode. In such a study, a muscle force and electromyography (EMG) were used as biomarkers. These experiments, which include a set up similar to the system 600 shown in FIG. 14, were conducted in parallel with in-silico experiments, with the aim of observing whether predictions made in-silico were observed in-vivo. Two sets of cuff electrodes 612, 614 were implanted along the sciatic nerve, with the proximal electrode being used to elicit action potential (AP) volleys which generate twitch contractions of the triceps surae muscle, and which were monitored via EMG electrodes and an isometric ankle torque. The distal electrode was used to deliver an LFAC conditioning current. The experiment measured the degree of attenuation of the twitch force as a function of LFAC current and LFAC frequency. The results of such experimentation are shown in FIG. 18, which provides data relating to the observed sequence of muscle force and EMG production with increasing LFAC amplitude. Additionally, FIG. 18 is labeled to characterize the onset of block for each frequency, along with the observation of breakthrough activation. The illustrated sequence begins with the twitch response from the interrogating pulse stimulation. Further, as seen, the amplitude of the twitch force and EMG decrease as LFAC block takes effect. However, with increasing LFAC amplitude, LFAC activation begins to take effect. Additionally, there is illustrated an offset in the force output that indicates tetanized contractions. Further, activation results in collision block, which ultimately extinguishes the twitch response from the interrogating pulse stimulation. At relatively high LFAC amplitudes, the contraction is tetanized, but with substantial ripple. The example shown in FIG. 5 illustrates that fused tetanic contractions with substantial force can be elicited and sustained for relatively long periods of time, which, in this example, is two minutes. FIG. 18 further illustrates that the contractions may not be smooth with ripple, which can be a consequence of the episodic activation obtained with LFAC.

Figure 19A:
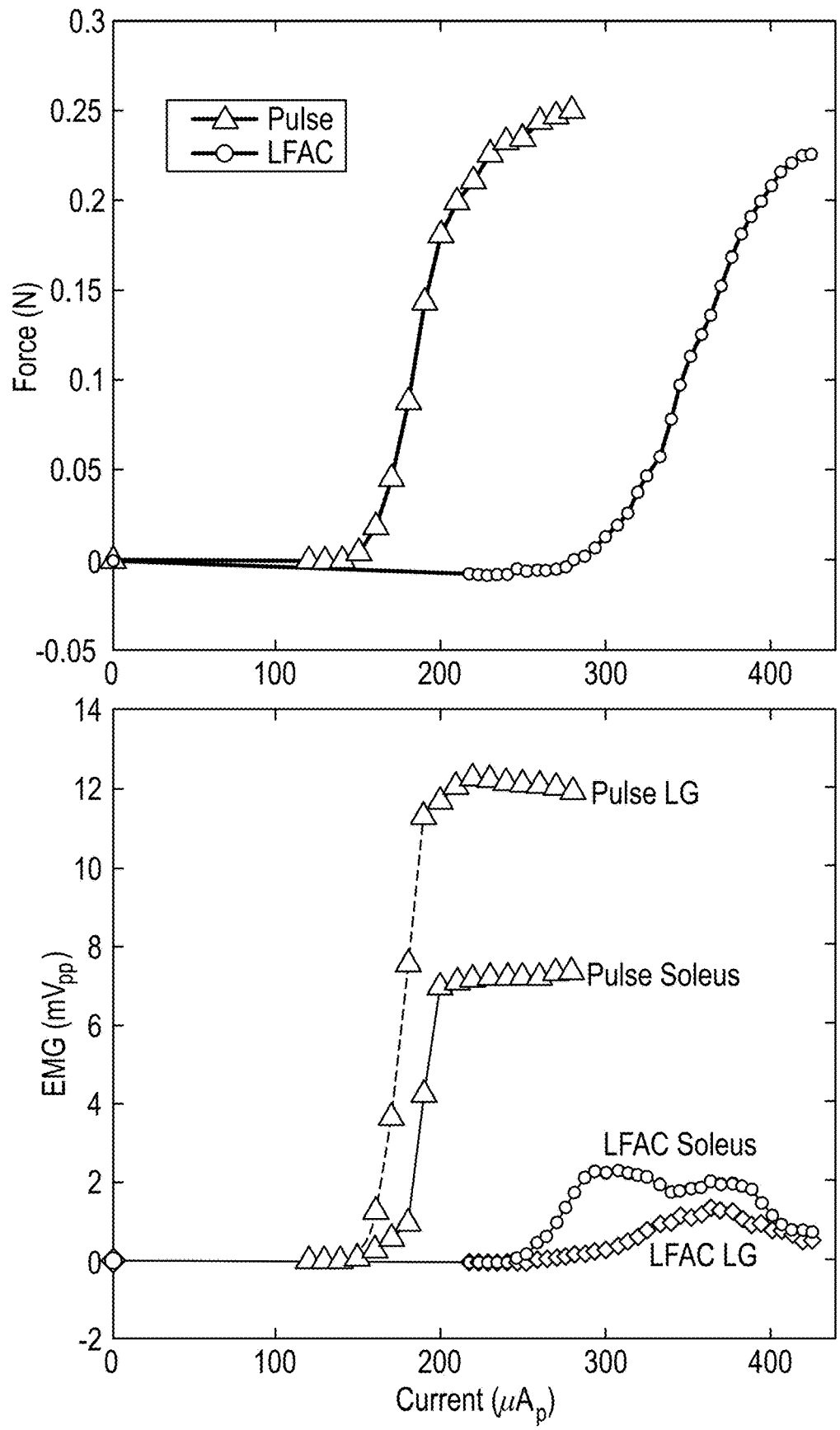
FIGS. 19A-C illustrate test results from experimentation similar to the experiment for FIG. 5, but in which two intramuscular electrodes were implanted in the lateral gastrocnemius (LG) and soleus (Sol) muscles.
Figure 19B:
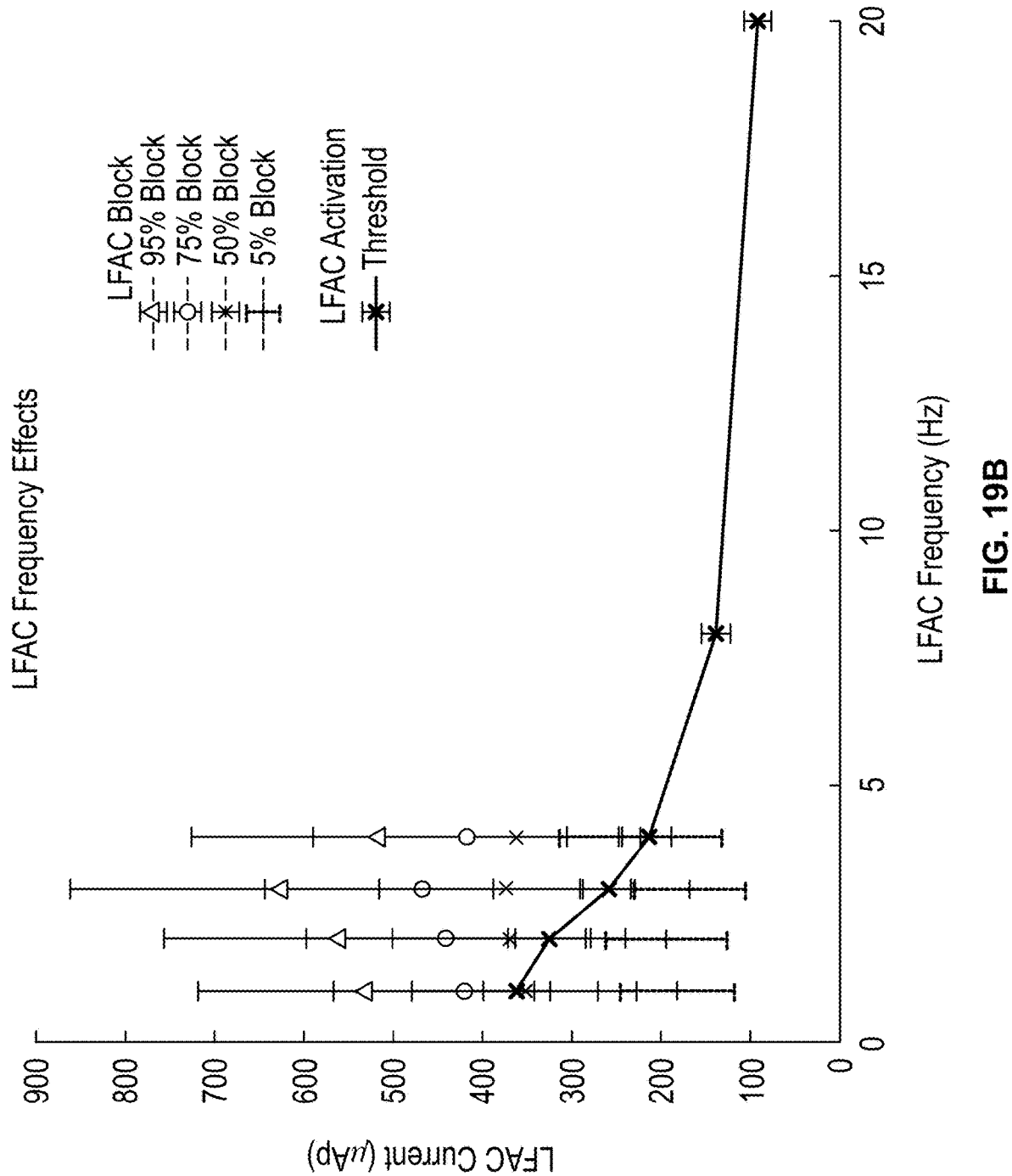
Figure 19C:
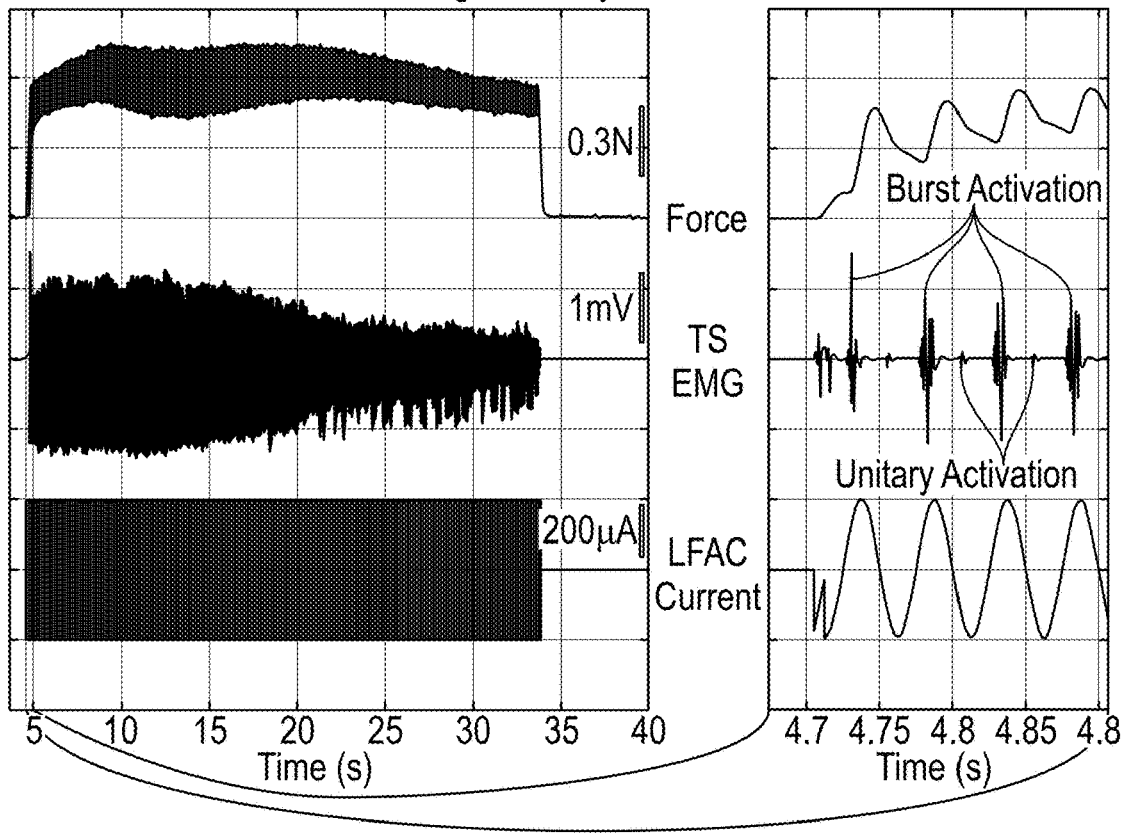
Figure 19C:
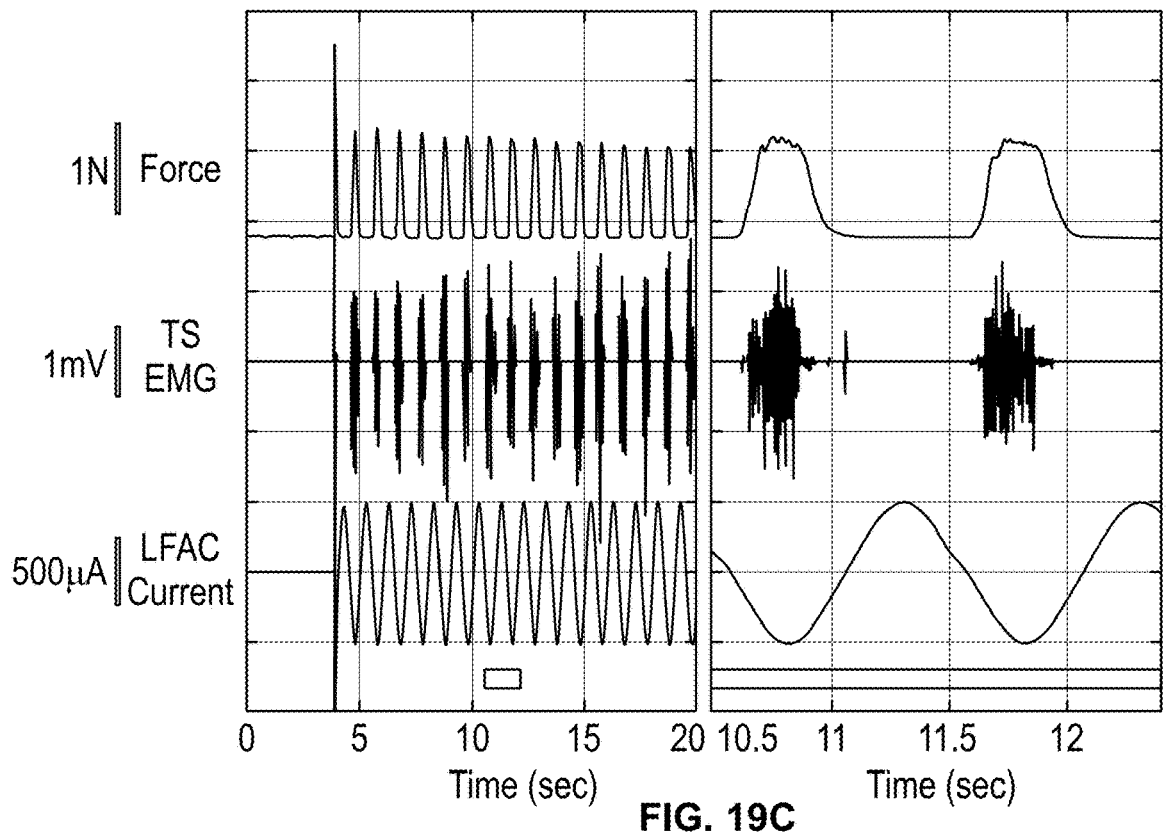

FIGS. 19A-C illustrate data associated with additional testing of LFAC using a system similar to the system 600 shown in FIG. 14. Additionally, the testing associated with FIGS. 19A-C was similar to that discussed above with respect to FIG. 18, with the exception that the testing involved two intramuscular (IM) electrodes being implanted in the lateral gastrocnemius (LG) and soleus (Sol) muscles. Both of these muscles are innervated by a common branch of the tibial nerve, namely the Lateral Gastrocnemeus/Soleus (LG/S) nerve. The LG is a pale, fast fatiguing muscle, while the Sol is a red, fatigue resistant postural muscle.

Isometric force recruitment curves, shown in FIG. 19A, were obtained using both pulse simulation and LFAC stimulation to generate approximately equivalent large force output. The chart shown on the top of FIG. 19A illustrates that both pulse and LFAC stimulation are able to activate muscles to produce comparable forces. The bottom chart in FIG. 19B illustrates that the order of activation. As illustrated, with respect to pulse simulation, measurement of the EMG from the IM electrodes showed that LG recruitment led Sol. However, contrary to pulse simulation, EMG recruitment curves from LFAC simulation demonstrate the fibers of the fatigue resistant Sol being recruited before the fatigable fibers in LG. Thus, the order of recruitment obtained using pule is reversed with LFAC stimulation This data further demonstrates the size-wise fiber recruitment that can be obtained via use of the LFAC waveform.

Another prediction that is supported by in-vivo evidence is the effect of electrode pitch and LFAC frequency on LFAC activation thresholds. The upper panel of FIG. 19B shows the evolution of block and activation as a function of LFAC amplitude and frequency. Two electrode pitches are also shown as 1.3 mm and 3 mm. FIG. 19B demonstrates that longer electrode pitch reduces the activation thresholds, while such pitch of the electrodes has little to no effect on block. Such a figure also shows the frequency dependency of the activation thresholds, which decrease as a function of increasing LFAC frequency. However, again, such variance in frequency has little, if any, effect on block. The lower panel in FIG. 19B plots exemplary activation and block thresholds for a 1.5 millimeter (mm) pitch electrode. In this figure, block is represented as thresholds of degrees of block, and is invariant to LFAC frequency, while activation thresholds decrease with frequency. Accordingly, FIG. 19B illustrates that LFAC block is stimulus frequency independent, while activation is frequency dependent and favors higher frequencies. These results verify the in-silico model predictions.

Further, as seen in at least FIG. 19C, both unitary and burst type activations are again observed during application of an LFAC waveform, with nerve activation beginning at the LFAC crossover point. Unitary activation is observed as occurring two times per LFAC cycle, while burst activation occurs once a cycle. The lower chart in FIG. 19C further demonstrates that activation threshold reduces with LFAC frequency. For example, the data in FIG. 19C shows isometric force production and EMG during LFAC stimulation at 1 Hz and 20 Hz. From the depicted data, frequency appears to alter the balance between unitary activation and burst activation. Moreover, as seen, burst activations are shown as occurring at relatively low frequencies, while increasing the LFAC frequency is seen as pushing the balance towards unitary activation. Accordingly, FIG. 19C illustrates that unitary activation occurs at the zero crossing of the LFAC waveform, while burst activation occurs near the peak currents.

Figure 20A:
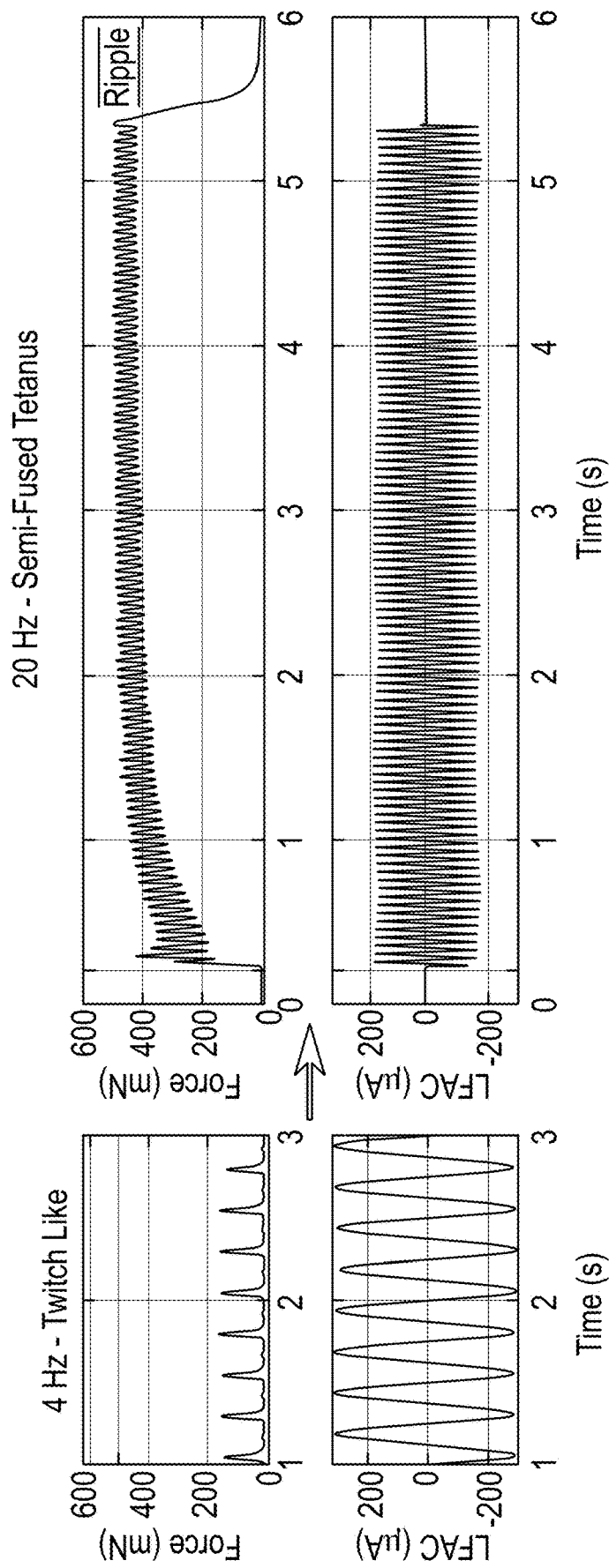
FIG. 20A illustrates the results of testing in which LFAC frequency caused twitch like contractions at 4 Hz, and smoother tetanized contractions at 20 Hz.
Figure 20B:
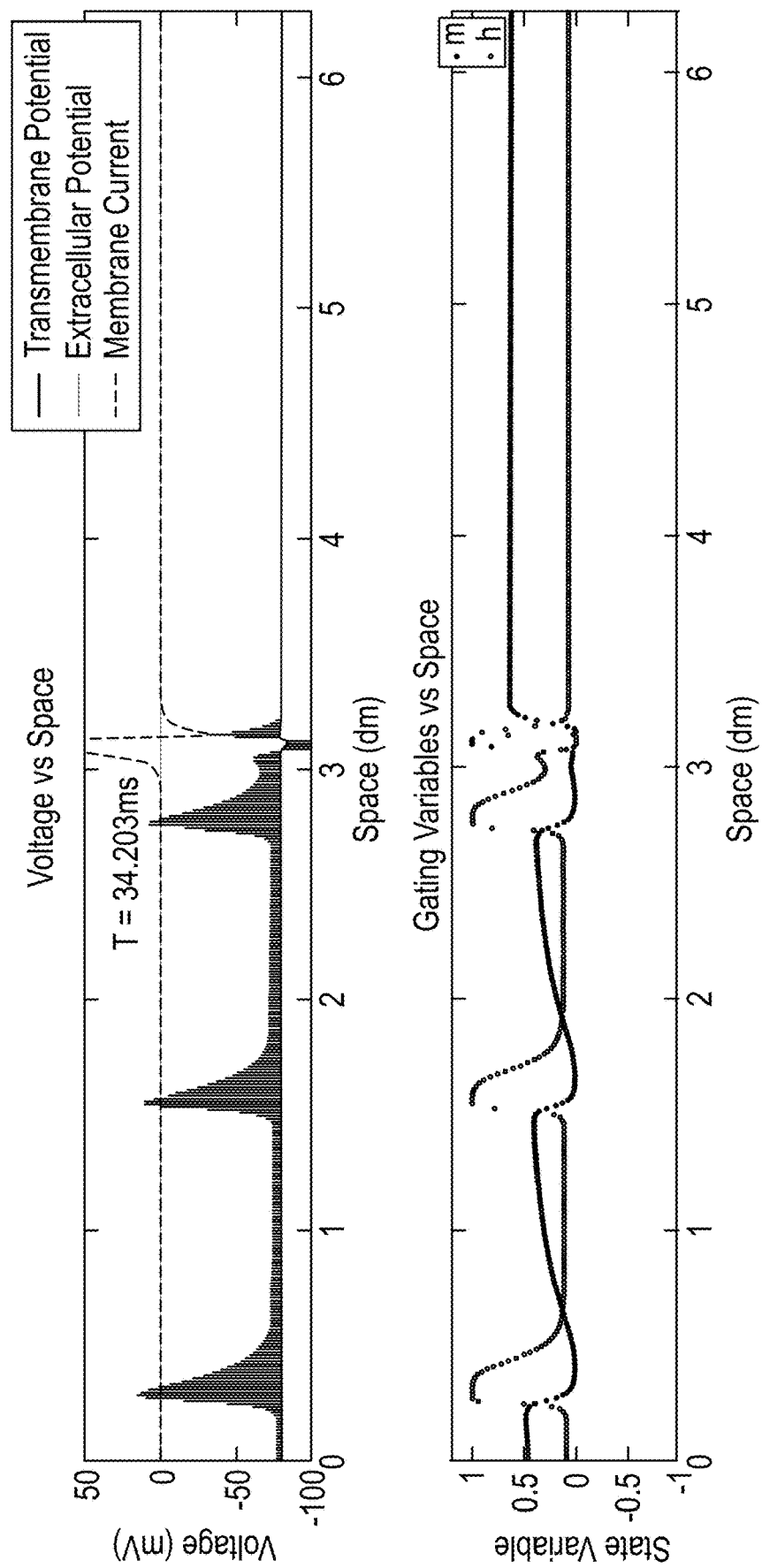
FIG. 20B illustrates an in-silico demonstration of unidirectional stimulation using an asymmetrical bipolar cuff electrode.

FIGS. 20A and 20B provide data showing strategies to generate smooth muscle contractions. Moreover, FIG. 20A demonstrates that increasing the LFAC frequency can result in a transition of twitch like contractions at 4 Hz to smoother tetanized contractions at 20 Hz. Such results can be used in connection with developing a strategy is to increase LFAC frequency. FIG. 20B is an in-silico demonstration of unidirectional stimulation using an asymmetrical bipolar cuff electrode. Unidirectional stimulation might improve stability and controllability of electrically activated muscles by reducing the segmental Hoffman-reflex components during electrical stimulation.

Frequency can play a role in the quality of muscle contraction produced by the muscle when using LFAC simulation. Moreover, lower LFAC frequency stimulation can result in extended twitch like contractions, as lower frequencies tend to favor burst type activation. With increasing frequencies, contractions can become fused with some ripple, as demonstrated, for example, for the 20 Hz LFAC waveform identified in FIG. 20A. However, there are some complexities in the stimulation. For example, at lower amplitudes of stimulation, the burst mode activation can be blocked every half cycle, which can result in unidirectional activation at the LFAC frequency. However, the unitary activation volley conducts bi-directionally, and at each zero crossing, or two times per LFAC cycle. Further, at higher stimulation levels, the activated burst mode volley can overwhelm the LFAC block under the cathode and conducts bi-directionally. Activation, like the unitary case can occur two time per LFAC cycle.

Examples related to the present disclosure are described below. A variety of alternative techniques can be used, and the examples are intended to be illustrative and not limiting or restrictive of the scope of the invention as set forth in the claims.

Example I

The performance of a carbon filler contact is amplified by means of electroplating a novel ICP material over the surface of the completed cuff 102 or cuff assembly 100 via electrodeposition. In experimental tests described in this disclosure, an ICP solution was used that includes poly(3, 4-ethylenedioxythiophene):poly(4-styrenesulfonic acid) ("PEDOT:PSS") with a carbon-black ("CB") filler. These tests demonstrate that the low frequency impedance at 1 hertz (Hz) of a representative cyanoacrylate/CG contact electroplated with this ICP material improved from an order of 106 ohms (Ω) with −48.0° phase to an order of 103Ω and −14.5° phase for contacts that were 0.5 millimeter (mm) wide with an arc length of 4.25 mm inside a 1.3 mm inner-diameter (ID) cuff assembly or electrode 100. In comparison, a bare stainless steel (SS) contact of the same size has an impedance of 105Ω with −39.1° phase.

Cyclic voltammetry was performed to determine the increase in charge capacity with the addition of the ICP/CB coating over the contact interface surface, which improved substantially from −23.24 millicoulomb (mC) to −838.54 mC and −40.54 mC to −1061 mC for Contact 1 and Contact 2, respectively. Following the fabrication of the cuff assemblies or electrodes 100, they were implanted into a series of rats for acute in-vivo LFAC experimentation to explore the viability of the new designs. Post experimental electrochemical analysis indicated that the electrode remained viable even after use in acute neuro-modulation.

While it is not intended that the present disclosure be limited by any theory whereby it achieves its advantageous result, it is believed that during electrodeposition of PEDOT: PSS, a capacitive boundary forms between adjacent colloidal particles that adhere to the surface of the electrode contact (in the order of PEDOT-PSS-PEDOT; two conductive layers separated by non-conductive PSS). This capacitive buildup between molecules reduces the ability for ions to flow freely between the deposited PEDOT and bulk solution. As a result, due to low capacitance in addition to less prolonged polarization at high frequencies, charge transfer tends to work uninterrupted; however, at lower frequencies polarization dominates, leading to breaking of adjacent PEDOT:PSS complexes. Through the addition of a conductive contaminant, such as porous CB, the PEDOT: PSS colloidal particles may become dispersed within the CB matrix and lead to less capacitive buildup between adjacent colloids and increased intercalation between ions in the bulk solution during stimulation. The CB-EDOT:PSS will diffuse, together, towards the working electrode and ultimately adhere to the surface, oxidizing the EDOT to PEDOT, thus forming the conductive polymer complex PEDOT:PSS/CB.

One method of this disclosure contemplates using a rigid cuff assembly or electrode 102 having a through hole 104 internal diameter of 1.3 mm that was three-dimensionally (3d) printed. The cuff assembly or electrode 100 may have two 25 μm deep windows or wells 108 with a pitch of 1 mm, width of 0.5 mm, and arc length of 4.25 mm. At the depth of 25 μm, the windows or wells 108 opened to a larger inset space that contained an exposed stainless steel wire. This larger space was filled with cyanoacrylate percolated with carbon graphite and surrounded the exposed wire. Collectively, this juncture made the surface of the electrode contact (see FIGS. 1-5 for example).

One aspect of this disclosure utilizes an ICP polymerization solution. More specifically, Ethanol ("EtOH") was added to double-deionized water ("ddH$_2$O") and mixed to create a fixed ratio of 1 EtOH:4 ddH$_2$O. A concentration of 1 mg/mL of carbon black was added to this solution and then sonicated to promote suspension of aggregate CB. Following suspension, a concentration of 8.75 mg/mL of PSS was added and the solution was agitated until it was considered uniform. Lastly, 4.2 mg/mL of EDOT monomer was added and purged with N$_2$ to prevent oxidation during storage and stored at 4° C.

Another aspect of this disclosure considers Electrochemical Impedance Spectroscopy ("EIS"). More specifically, a two-point galvanostat, full-spectrum, rapid EIS was performed via an electrochemical interface station. An input noise source was generated and passed through an amplifier before being introduced to the Solartron and subsequently the electrode-electrolyte interface. Voltage was recorded on the working electrode (percolated carbon electrode) and graphite rod counter electrode, amplified via a two-channel compact filter/amplifier followed by digitizing at 500 kHz using a data acquisition device.

EIS recordings were made at two separate points, once before and after the electrodeposition and characterization processes. Results were interpreted in MATLAB (2019a, Mathworks; Natick, MA). EIS was performed in phosphate buffer saline ("PBS") solution at pH 7.4. Calibration of the EIS station was performed using a Solarton 12861 Test Module Circuit.

One aspect of this disclosure utilizes Cyclic Voltammetry ("CV"). More specifically, a three-point potentiostat CV was performed in pH 7.4 PBS solution in which a 4 Vpp triangle-wave with 0 DC offset and 0.5 Hz was generated and applied across the percolated carbon working electrode and graphite rod counter electrode. An Ag/AgCl electrode soaked in a 4M KCl solution was used as the reference electrode and the differential voltage was taken between the working and reference electrodes. Results were digitized at 500 kHz and sampled at 500 Hz. Cathodic charge storage capacity was calculated. Results were interpreted in MATLAB.

The electrodeposition of ICP was then analyzed. The ICP polymerization solution containing EDOT monomer was electrochemically polymerized onto the surface of the fabricated cuff electrodes. Potentiostat electrodeposition at 1 V lasted for 20 minutes, or until the well was filled with EDOT:PSS/CB. The extent of deposition was monitored through light microscopy following the deposition time to determine whether the deposited complex spilled out from the well. Following electrodeposition, the structures were rinsed in ddH2O.

As a result, PEDOT:PSS/CB was successfully deposited on the percolated carbon graphite contacts. The uncoated contact was a deep black, but became glossy, appearing more like a mat black post coating. A color change may be indicative of the electrode coating, with thicker coatings appearing darker. A top-down view of the contact wells via light microscopy suggested that Contact 1 had very small variations in the morphology of the top layer compared to Contact 2 which was very smooth, similar to the smoothness of a graphite pencil.

Figure 7:
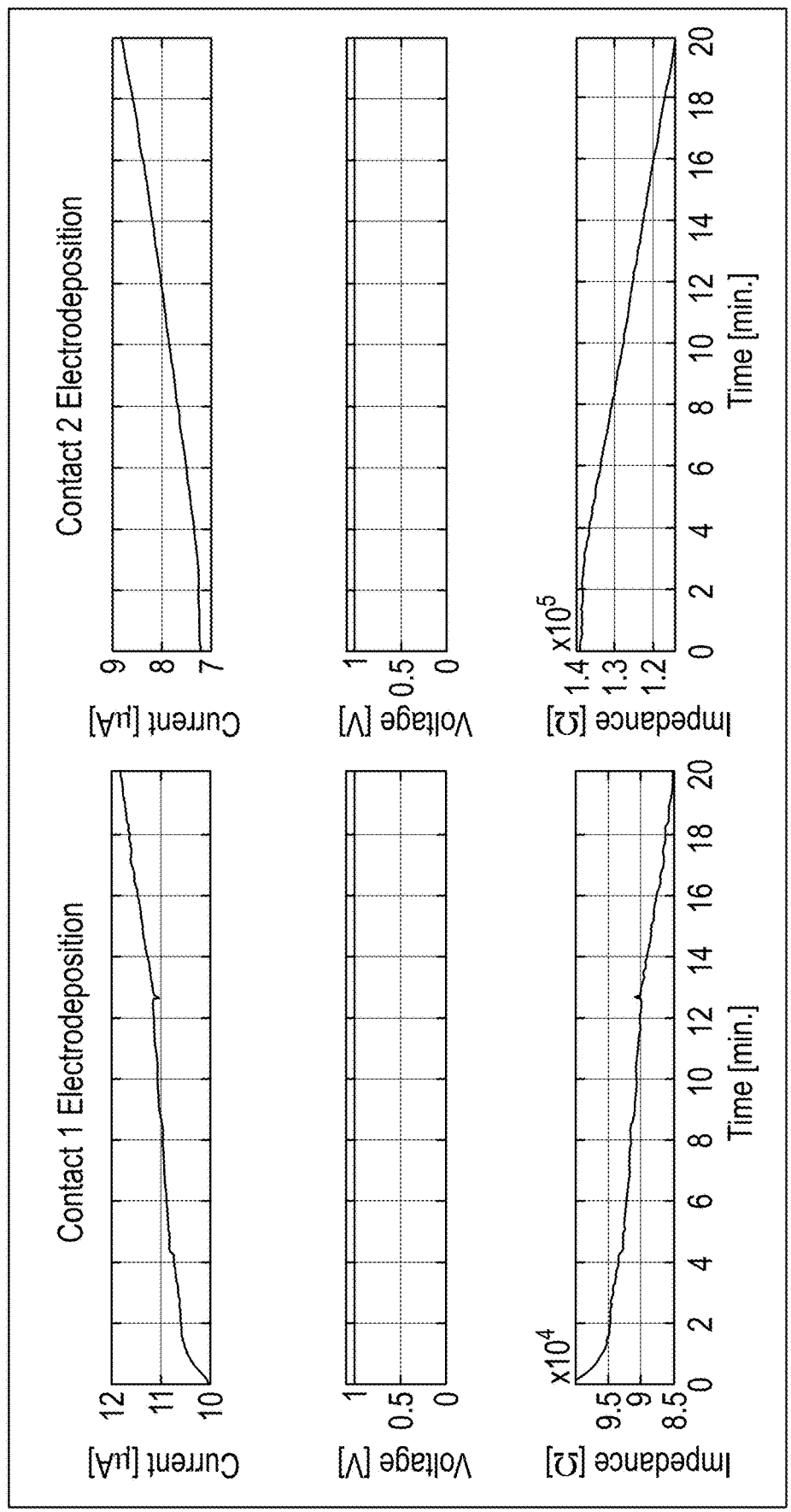
FIG. 7 is a graphical representation of current, voltage, and associated impedance of a PEDOT:PSS/CB during coating of the electrode in an EDOT:PSS/CB solution.

FIG. 7 shows the current, voltage, and associated impedance of the PEDOT:PSS/CB electrode in the EDOT:PSS/CB solution. Voltage was maintained at 1 V for the entirety of the deposition time; current and impedance were positively and negatively proportional to deposition time, respectively. Contact 2 was in the solution for more than two minutes before it began undergoing noticeable deposition.

Figure 8:
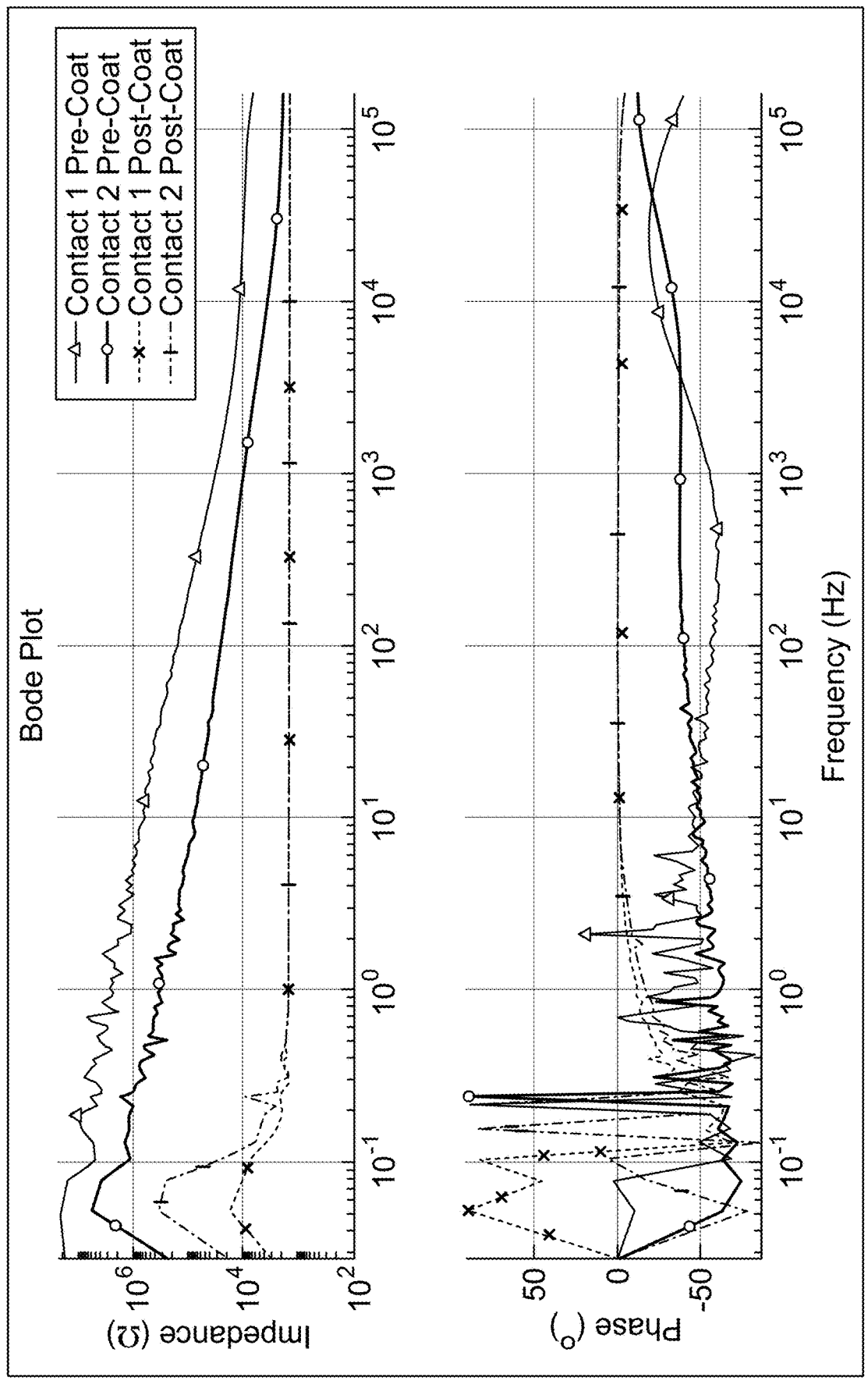
FIG. 8 is a graphical representation of electrochemical impedance spectrum results of electrodes with and without the PEDOT:PSS/CB coating.

Impedance of Contact's 1 and 2 prior to deposition were $2.48*10^6 \Omega$ and $3.32*10^5 \Omega$ with a corresponding phase of $-32.5°$ and $-62.1°$, respectively. Following deposition, Contact 1 and 2 coated with PEDOT:PSS/CB had an impedance of $1450\Omega$ and $1500\Omega$ with a corresponding phase of $-11.5°$ and $-18.0°$, respectively. FIG. 8 shows the results of the pre- and post-coated electrodes. The decrease in phase between the uncoated and coated contacts is attributed to a decrease in capacitive reactance. Accompanied with this decrease is a drop in impedance values between the uncoated and coated electrode states. This impedance change shows that the coating successfully adhered to the base substrate.

In-vivo pre- and post-experimental contact-to-contact impedance (FIG. 9) indicated a change of nearly 1 k$\Omega$ and phase change of $-10°$. These values incorporate the impedance of the nerve between each contact, and thus do not provide the impedance of each contact, respectively.

Figure 10:
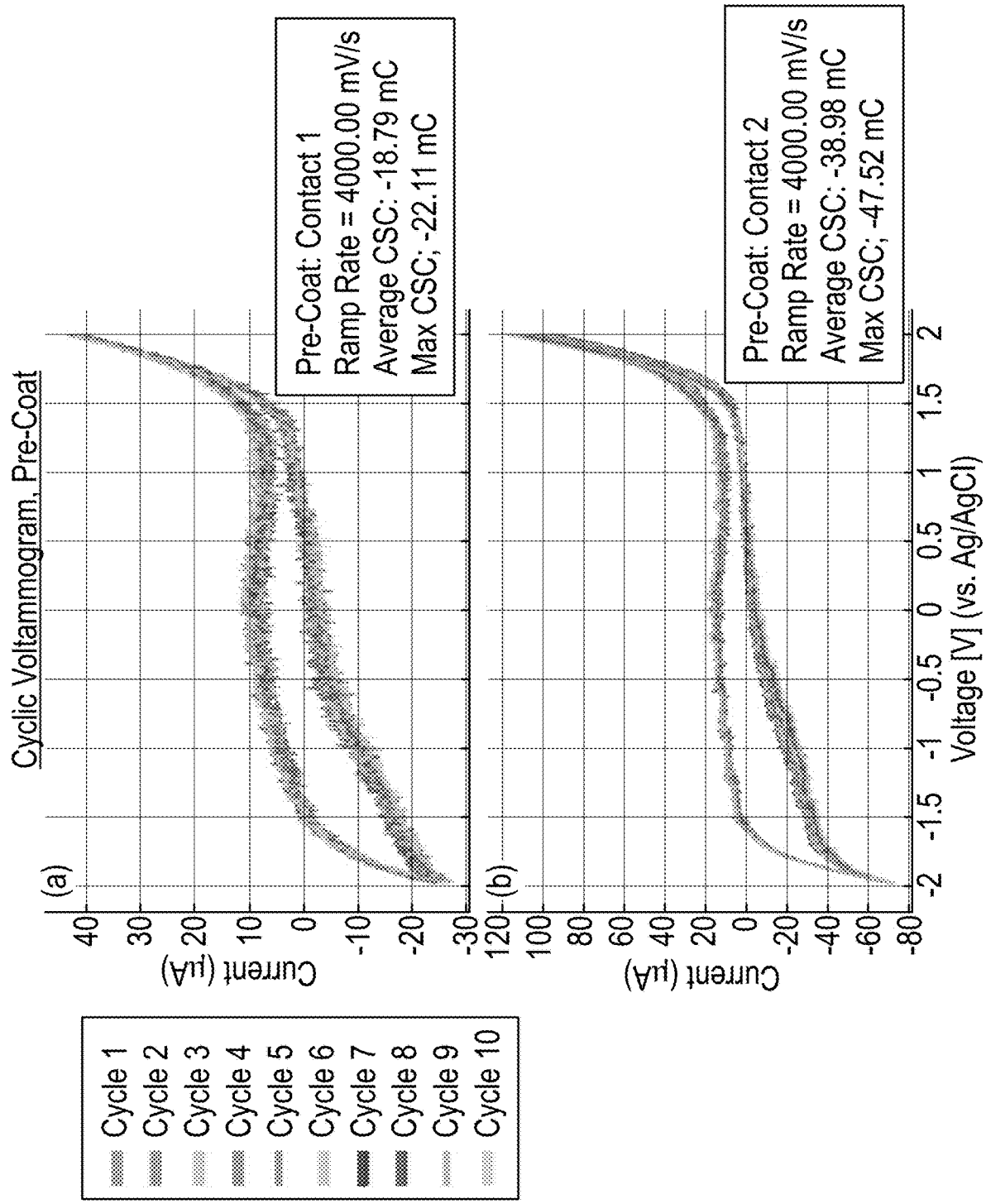
FIG. 10 is a graphical representation of voltammograms for the uncoated and coated electrode contacts.
Figure 10:
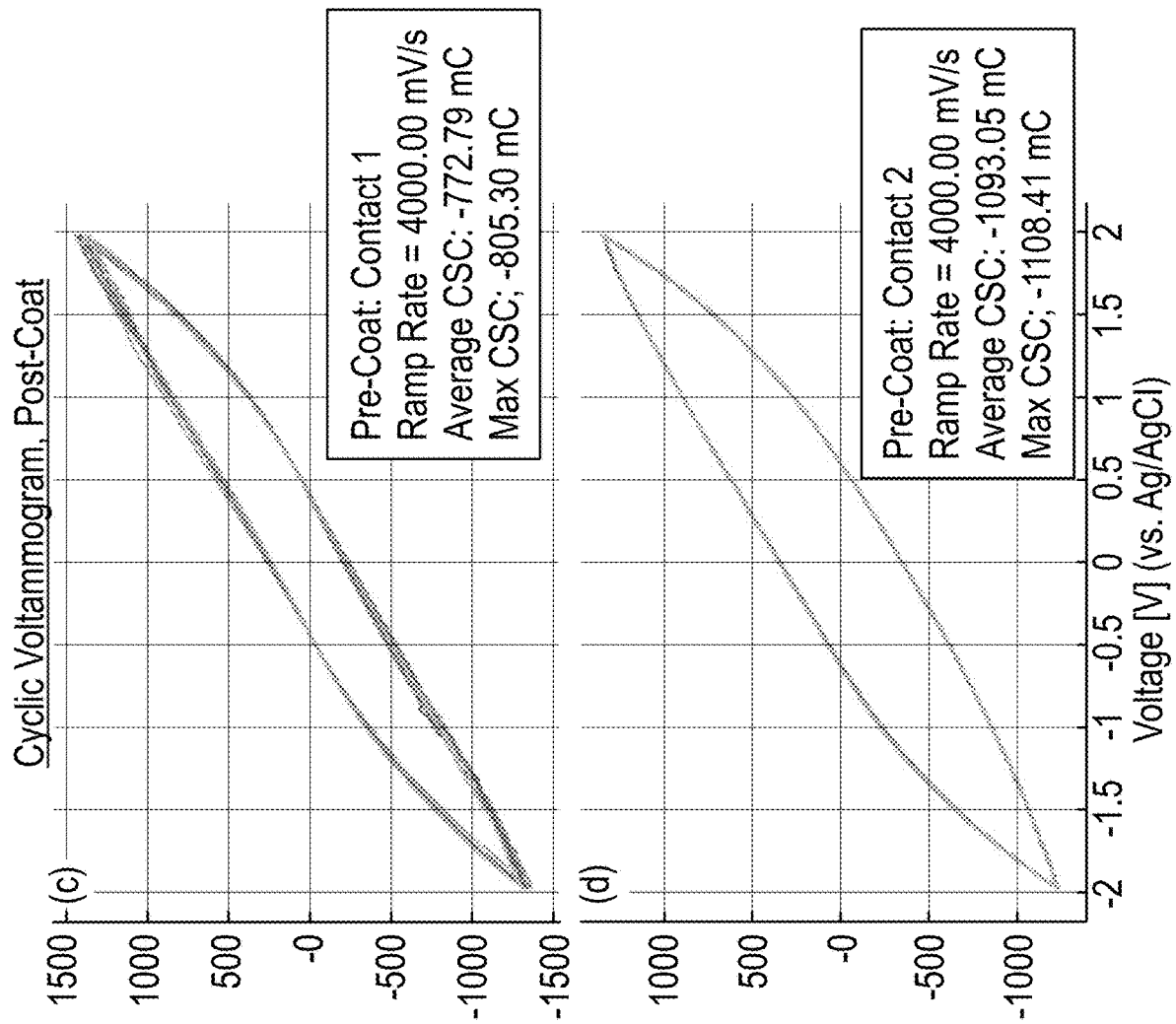

This disclosure also contemplates utilizing Cyclic Voltammetry ("CV"). More specifically, the charge storage capacity between the coated and uncoated electrodes increased by a factor of 36 and 28 for Contact 1 and 2 (CV shown for Contact 2 in FIG. 10). In addition, the water window increased significantly from 1.4 V and $-1.7$ V to beyond $+/-2$ V for the cathodic and anodic current's at a 4000 mV/s scan rate, respectively. FIG. 10 exhibits the CV results for the uncoated and coated electrode contacts in 1×PBS solution at a pH of 7.4. The voltammograms of the coated electrodes indicate that the PEDOT:PSS/CB coating gave rise to the characteristics of a psuedocapacitor, with what appears to be slightly faradaic components protruding through the large reactive capacitance.

Cyclic voltammetry was performed on the percolated cyanoacrylate carbon contacts at 0.5 Hz between $-/+2.0$ V (4000 mV/s scan rate). Frequency was chosen based on the presumed minimum operating conditions for LFAC and the voltage range was selected to force the electrode into nonlinear operation. Under these conditions, currents were observed for the uncoated contacts and the nonlinear regions occurred at 1.0 V and $-0.5$ V in the cathodic and anodic current ranges, respectively. Due to the large scan rate the diffusion layer was greatly diminished, making it difficult to identify the faradaic charge transfer associated with the adsorption and release of ions from the electrode-electrolyte boundary. CV was then acquired a second time under coated conditions and it was observed that the charge storage capacity increased drastically for both contacts. The extreme charge storage characteristics of the coated contacts (3.95 and $4.99*10^6$ mC-cm$^{-2}$ for Contact 1 and 2, respectively) seen in FIG. 8 as a result of the high scan rate may be obscuring most of the faradaic charge transfer while expanding the nonfaradaic, reactive capacitive components. This assumption may be verified by repeating these experiments at a lesser scan rate to identify if faradaic components can be seen during diffusion-controlled reactions. Scan rates this high are not typically used to determine charge storage; rather, it is recommended using scan rates no more than 50 mV/s. In addition, the charge transfer capabilities increased for the voltage range studied in the coated contacts and there was no indication of nonlinearity within the bounds of $-/+2.0$. Increased charge transfer may be a result of increased intercalation at the contact surface which leads to the psuedocapacitive behavior.

The uncoated impedance of Contact 1 is greater than Contact 2. There was also a large capacitive phase component in both contacts with a large impedance differential between the two contacts. A possible explanation may be unequal distribution of graphite within the percolated cyanoacrylate. Upon coating, impedance drops significantly for both contacts and they approach their infinite resistance values very early, less than 1 Hz, in the frequency vs. impedance plots (FIG. 7). This is change was recorded as three orders of magnitude in Contact 1 and two orders in Contact 2. Furthermore, there was a significant change in phase from the starting state for both contacts. However, previous studies on the impact of phase and impedance on neuromodulation electrodes indicate overall impedance plays the primary role in determining signal-to-noise ratio in recording electrodes and ability to safely reversibly inject charge during stimulation.

Current increased during the electrodeposition of the PEDOT:PSS/CB by nearly 2 μA in both cases. Deposition was performed at 1 V DC. Despite prior work indicating that potentiodynamic and galvanostatic deposition resulted in a more consistent and equal distribution of PEDOT, we opted to coat potentiostatically at 1 V, close to where the linear region diverges into nonlinearity. The reason for choosing potentiostatic deposition was to ensure that the PEDOT:PSS would deposit to the surface of the contacts in the presence of a contaminant (CB) and, according to prior experimentation, 1 V DC was an adequate potential to obtain deposition. Results indicated that deposition occurred; however, due to hardware limitations it was difficult to determine the impedance near DC (or in extremely low frequencies) using the rapid EIS technique described above. As a result, the impedances that were shown during deposition may not correlate directly with the observation at 0.5 Hz and above. Nonetheless, instantaneous impedance was monitored and observations showed a linear decrease with respect to deposition time.

Figure 9:
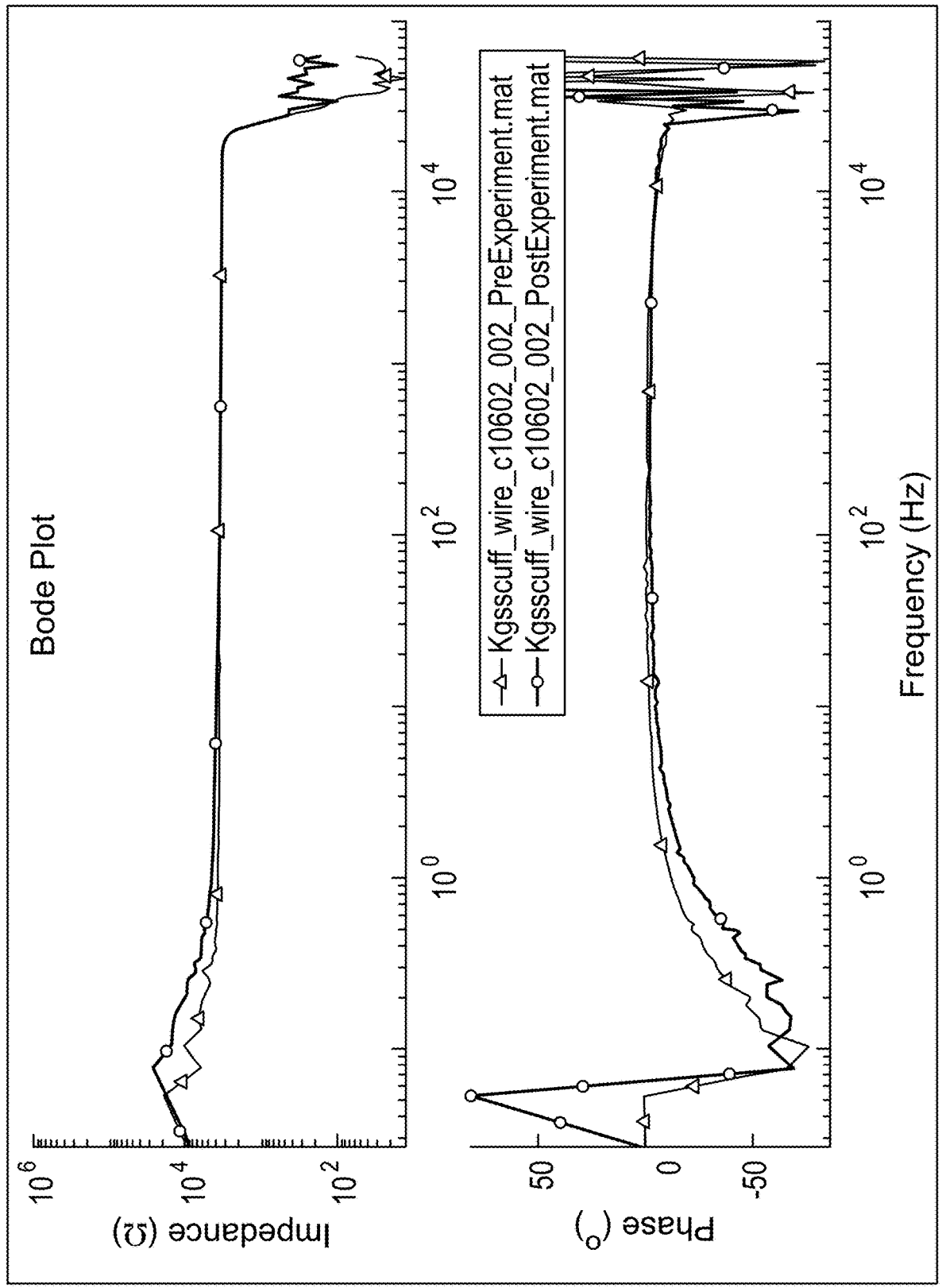
FIG. 9 is a graphical representation of in vivo pre- and post-experimental contact-to-contact impedance.

To test the efficacy of the electrodes in-vivo, contacts were fixed to the nerve at the beginning of an experiment and used to characterize LFAC activation and block. Measurements were taken before activation and block trials and again post-facto. Results indicated a change in impedance of nearly 1 kΩ and decrease in phase by nearly 10° (FIG. 9). Assuming that the electrodes did not become displaced and the nerve was undamaged during experimentation, the recorded values indicate that the electrode performance may have decreased slightly during the experiment. However, there was no criterion used during activation or block that limited the amplitude or frequency of current delivered to the animal during the experiment and voltage exceeded 10V during the trails. These electrodes were pushed well beyond what was necessary to operate during experimentation. In sum, the electrodes performed extremely well during the experiment with only a slight decrease between the pre- and post-experimental measurements, however, the recorded current never leave the linear region.

The present data indicates that PEDOT:PSS/CB safely delivers current to biological interfaces across a large frequency bandwidth during neural stimulation. This electrode design is valuable when modulating at low-frequencies during LFAC experimentation. Presented electrode contacts have a charge storage capacity of $5*10^6$ mC-cm$^{-2}$ at 4000 mV/s scan rate from −/+2V. Following normalization of impedance for contact area in comparison to similar ICP studies, the present formulation appears to give lower impedance results across a larger frequency bandwidth. In order to make a valid calculation of charge storage capacity, CVs must be performed at a lower scan rate. Following fabrication of the aforementioned electrode, it was placed into a Sprague-Dawley rat for in-vivo PNS experimentation on the sciatic nerve.

Figure 11:
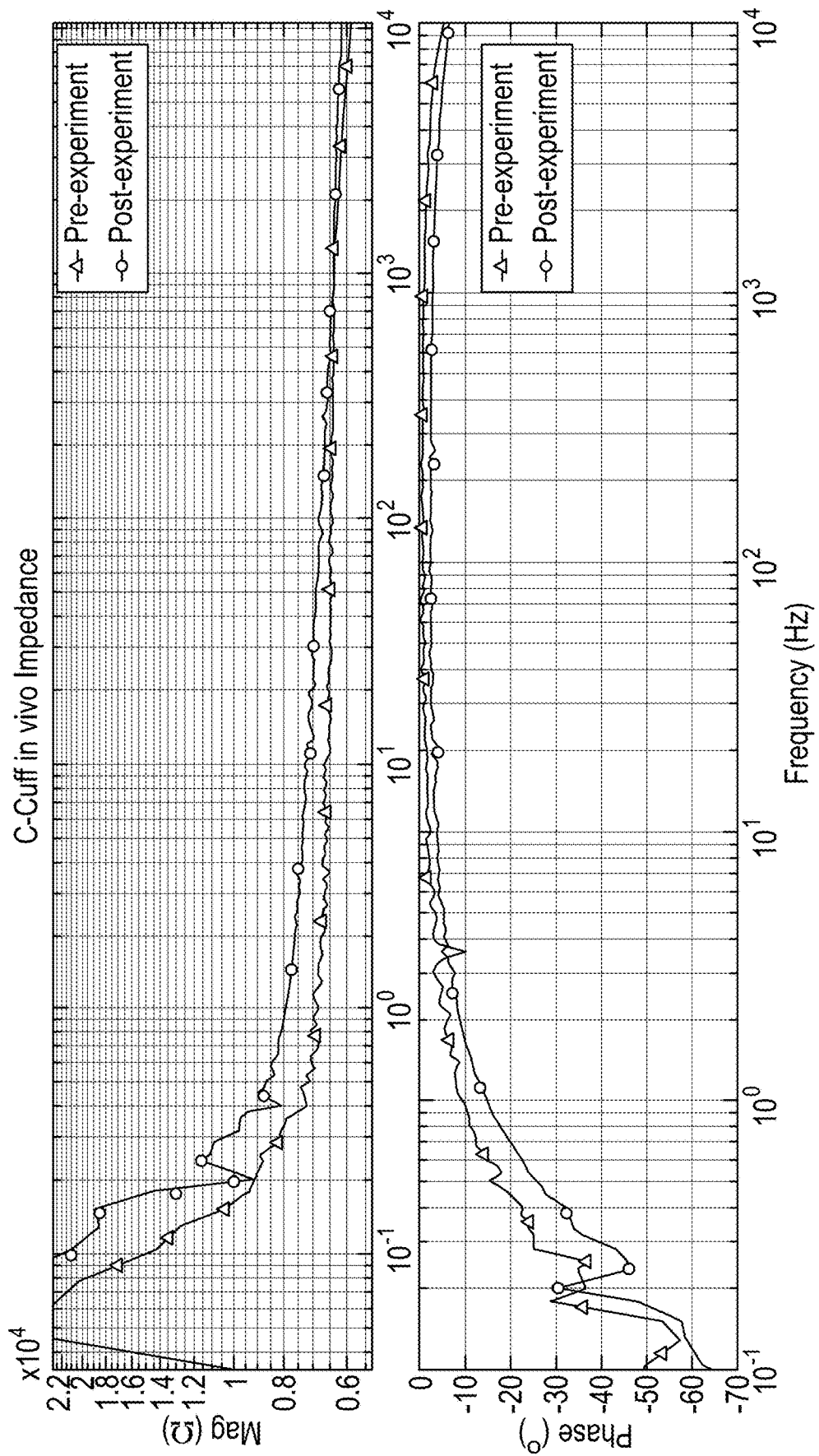
FIG. 11 is a graphical representation of the cuff assembly in vivo impedance and the Pre- and Post-experiment Bode plot showing the impedance magnitude and phase.
Figure 12:
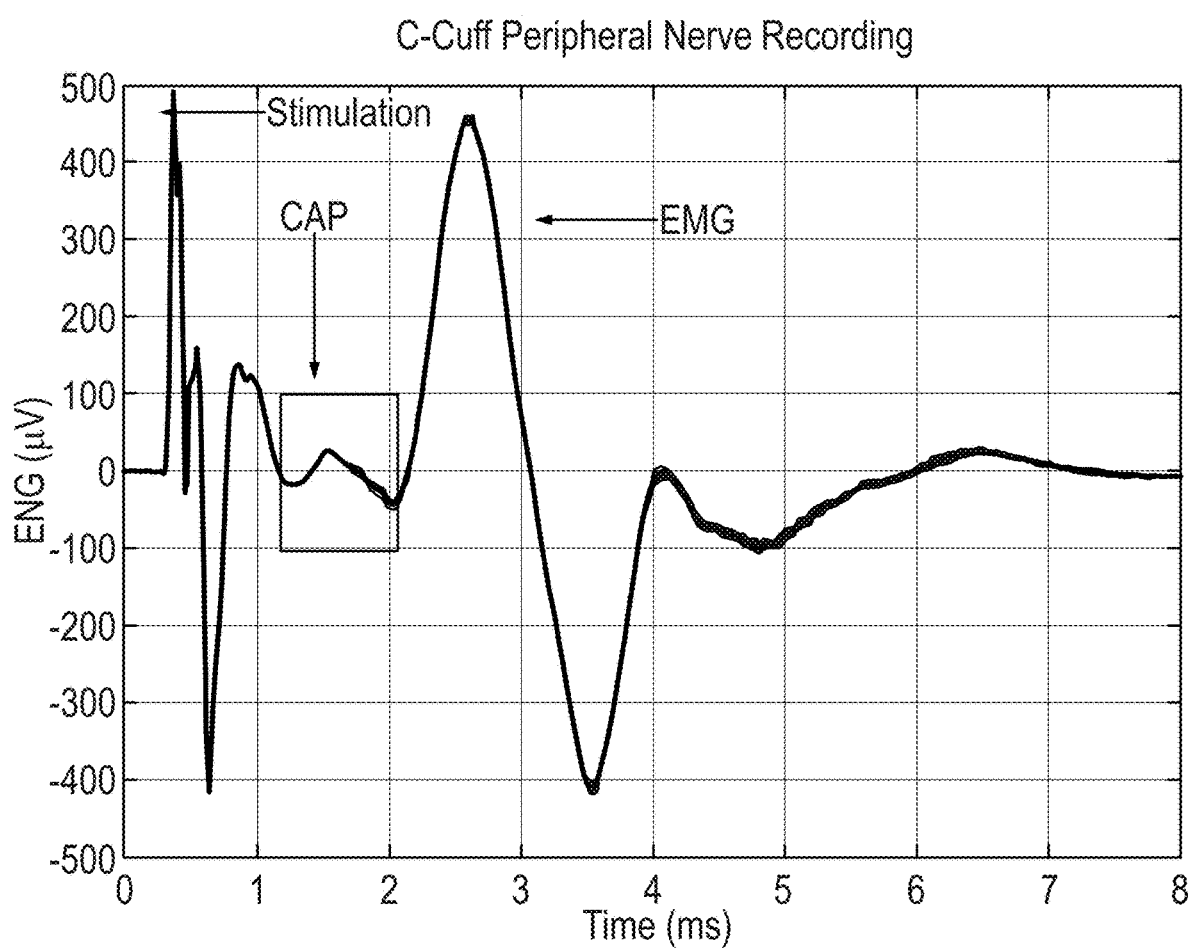
FIG. 12 is a graphical representation of peripheral nerve recordings showing cuff recordings of the pulse stimulus artefact, compound action potential, and compound EMG artefact.
Figure 13:
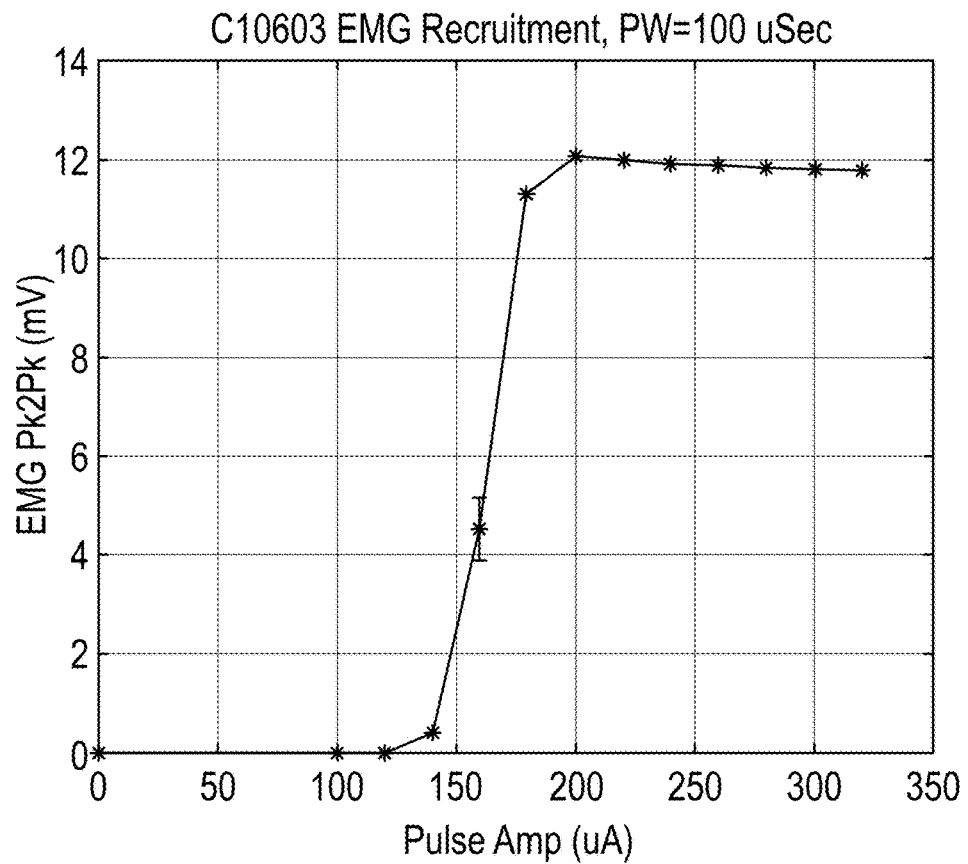
FIG. 13 is a graphical representation of a recruitment curve of stimulus strength as a function of motor nerve activation showing stimulation of peripheral nerve with the cuff assembly using pulse stimulation.

FIG. 11 illustrates the cuff assembly 100 in vivo impedance and the Pre- and Post-experiment Bode plot demonstrates the impedance magnitude and phase are within favorable ranges. FIG. 12 illustrates a graphical representation of ENG (electromyography) as a function of time, and provides information regarding cuff recordings of the compound action potential. Moreover, FIG. 12, illustrates a recording of the cuff assembly 100 in vivo peripheral nerve compound action potential, with electromyography (EMG) being identified. FIG. 13 illustrates a recruitment curve showing successful stimulation of peripheral nerve with the cuff assembly 100 discussed herein. In FIG. 13, a recruitment curve shows successful cuff stimulation based on EMG recordings.

Example II

Formation of a PEDOT:PSS/CB interface coating over an electrode as described herein was achieved by electrodeposition in accordance with the following method.

First a 20 mL 20% (v/v) ethanol/double-deionized H$_2$O (EtOH/$_{dd}$H$_2$O) solution was prepared. To the EtOH/$_{dd}$H$_2$O solution were added 3,4-ethylenedioxy-thiophene (EDOT) and poly(4-styrenesulfonic acid) (PSS) in a ratio of 0.4 (v/v). The concentrations of EDOT and PSS within this solution was 3.33 mg/mL and 6.94 mg/mL, respectively. The PSS was added to the EtOH/$_{dd}$H$_2$O solution before the EDOT monomer to prevent agglomeration. Immediately following addition of the EDOT and PSS, CB was added to provide a desired concentration of CB in the solution, such as about 1.0, about 2.0, about 0.10, about 0.05 or about 0.01 mg/mL. To mix, nitrogen gas was bubbled through the solution during sonication to minimize the presence of oxygen. Sonication was continued for about 30 minutes. If the solution is not to be immediately used, it is sealed in a container and stored in a refrigerator at about 4° C. until used.

An electrode to be coated is placed in the above solution with only the surface or surfaces to be coated left uncovered, along with an Ag/AgCl reference electrode and a carbon rod counter electrode. In one mode of coating the electrode surface(s), the electrochemical cell was run potentiostatically at a DC voltage of about +1 V for 20 minutes. In a second mode of coating the electrode surface(s), the cell was run under galvanostatic conditions at +200 μA for about 5 minutes. Following the depositing period, electrodes were removed from the solution.

Addition of CB to the PEDOT:PSS ICP matrix greatly reduced the impedance of the conductive polymer at frequencies above 100 Hz relative to a PEDOT:PSS ICP without CB. CB concentrations above 1 mg/mL significantly reduced impedance relative to those below 1 mg/mL. In low frequencies, PEDOT samples appear to be less capacitive; however, at higher frequencies the CB additive provides a greater and more abrupt attenuation in both impedance and phase elements. Increased CB concentration led to a greater loss in impedance and positive gain in phase. At low frequencies (less than 0.1 Hz), the CB-lacking samples attained a more substantial decrease in phase until about 1 to 10 Hz. This decrease is greatest in samples that contain 1 and 2 mg/mL CB; samples that are less than this appear to have similar phases as the PEDOT:PSS without CB. Samples that had 2 mg/mL CB resulted in a significant decrease in impedance, with the $R_{inf}$ approaching 100 Ohms rather quickly.

Cole-Cole analysis provided a quick insight into the capacitive nature of the coated electrodes. PEDOT:PSS and PEDOT:PSS/CB significantly reduces the capacitive elements of the electrode, which can be corroborated with the phase results shown in a Bode plot. Samples that had a CB concentration of 2 mg/mL appeared to be the least capacitive. As the concentration decreased, capacitive elements increased. The samples containing 0.10, 0.05, and 0.01 mg/mL CB tend to approach similar complex response (w=infinity) that is seen in the PEDOT:PSS-only samples. PEDOT:PSS and bright or sanded uncoated surfaces are similar in their capacitive elements, as indicated by the nearly linear Cole-Cole response in the two samples; in both cases, the R0 is not viewable within the real-axis limits of the graph. This is not the case for samples containing more than 1 mg/mL CB, as they have an R0 that appears to reside below 200 Ohms. In all cases, increased CB concentration led to a lowering of the high corner frequency.

Example III

In this example, the capability of the LFAC waveform to excite peripheral nerve fibers was studied. Moreover, the below-discussed example provides experimental proof of the efficacy of the LFAC waveform to activate mammalian cervical vagus nerve and induce Hering-Breuer (HB) reflex.

The study further assessed LFAC at frequencies of 5 Hz, 10 Hz, and 20 Hz, and was also directed to determining the threshold of activation as function of the applied LFAC frequency. Data associated with the results of this study are shown in FIGS. 21-24.

The left cervical vagus nerves of five adult male domestic swine, each weight approximately 50 kilograms (kg), were isolated bilaterally following sedation and continued isoflurane anesthesia. Vital signs were continuously monitored during the experiment, and breathing change was measured through a pressure transducer cuff placed around the animal chest. Two bipolar cuff electrodes, similar to the electrodes 612, 614 discussed above, were placed on the isolated nerve, and a rostral electrode was used for LFAC stimulation. The cardiac effect was eliminated via crushing the nerve most caudally, which is similar to the caudal vagotomy, where the stimulation affects the afferent pathways only.

The LFAC waveform was generated as a continuous sinusoidal waveform using an arbitrary function generator (Analog Discovery 2, Digilent® Inc., Pullman WA), and controlled by a tuning application written in LabVIEW®. The LFAC waveform was delivered to the rostral electrode via a custom built analog optical isolator followed by an isolated voltage controlled current source (CS580, SRS: Stanford Research Systems) with a constant gain of 1 mA per volt. The LFAC stimuli were applied using three frequencies: 5 Hz, 10 Hz, and 20 Hz. In one experiment, the LFAC frequency was increased to 100 and 500 Hz. With each frequency, the LFAC stimuli were applied at different amplitudes and each stimulation amplitude lasted for about 20 seconds and followed by a zero-amplitude period to allow for breathing recovery. Because the activation of HB reflex might cause complete stoppage of animal breathing, the periods of LFAC application were kept at minimum.

During LFAC application, the voltage drop versus the reference electrode was measured continuously via a calibrated monitored output of the current source. This allowed for monitoring and maintaining the linearity of the input current and the output voltage across the electrode as an indication of the maximum current to be applied without exceeding the cell potentials that could otherwise cause the hydrolysis of water (e.g., water window). Additionally, the change in inter breath intervals were measured simultaneously to determine the activation of HB reflex and threshold of activation.

The acquired breathing data was processed digitally using a custom MATLAB script (Version: R2018b, The MathWorks). The analysis was performed with respect to the applied LFAC frequency and amplitude. Further, the instantaneous breathing rates during the baseline (initial period before LFAC stimulation) and during LFAC stimulation were calculated by measuring the time between each breath peak. Because the baseline breathing rate was different for each animal, the instantaneous breathing rates were normalized to the average instantaneous breathing rate during baseline of each run. The threshold of activation was determined as the first LFAC amplitude that caused an increase in the inter intervals between breathing peaks.

During LFAC stimulation, the frequency and current amplitude to peak ($mA_p$) were quantified. The LFAC waveform was applied through a bipolar electrode. The current flowed from contact to contact and the potential spanning the electrodes relates to the full electrochemical cell potential. At any given phase of the sinusoidal LFAC waveform, the relevant cell potential is the potential across the cell, the relevant current the current between the contacts, and not the peak-to-peak value of the sinusoid.

Figure 21:
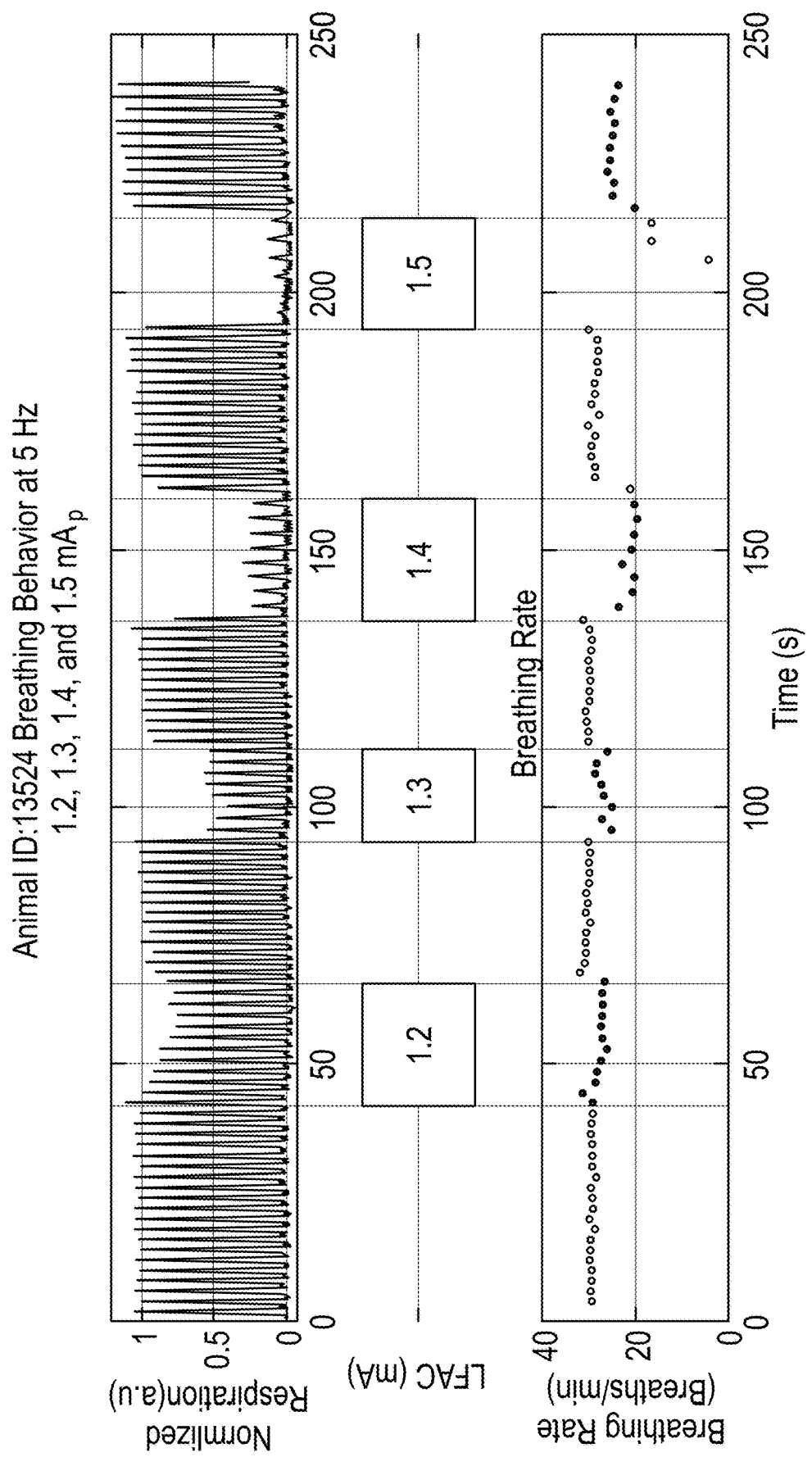
FIG. 21 illustrates the effect a 5 Hz LFAC stimulation at amplitudes of 1.2 mA$_p$, 1.3 mA$_p$, 1.4 mA$_p$, and 1.5 mA$_p$ frequencies can have on breathing behavior when applied to the vagus nerve to elicit a Hering Breuer reflex response in an anaesthetised pig model.

FIG. 21 illustrates the effect of a 5 Hz LFAC stimulation on the breathing behavior at different amplitudes, namely 1.2 $mA_p$, 1.3 $mA_p$, 1.4 $mA_p$, and 1.5 $mA_p$, with the different amplitudes shown in different shaded regions. The upper panel in FIG. 21 shows the breathing peaks used in calculating the instantaneous breathing rate, while the lower panel illustrates the instantaneous breathing rate change as the LFAC amplitude changes in breath per minute. The breathing rate analysis showed a clear activation of the vagus nerve fibers that was able to evoke HB reflex. The results, as illustrated in FIG. 21, show a representative continuous recording of the breathing change during the application of 5 Hz LFAC waveform at different LFAC amplitudes. The lower trace shows the instantaneous calculated breathing rate per minutes based of the time intervals between each adjacent breathing peaks. As the 5 Hz LFAC amplitude increases, the breathing rate decreases further until reaching a point of non-breathing at an amplitude of 1.5 $mA_p$. The recovery time between each LFAC increment was observed to resume the normal breathing, as shown in the calculated breathing rate. As expected, the HB reflex resulted in a larger time interval between the breathing peaks, and further increments of LFAC amplitude resulted in a complete stoppage of breathing. Similar results were also obtained using 10 and 20 Hz LFAC frequencies with activation thresholds that were lower than 5 Hz.

Figure 22:
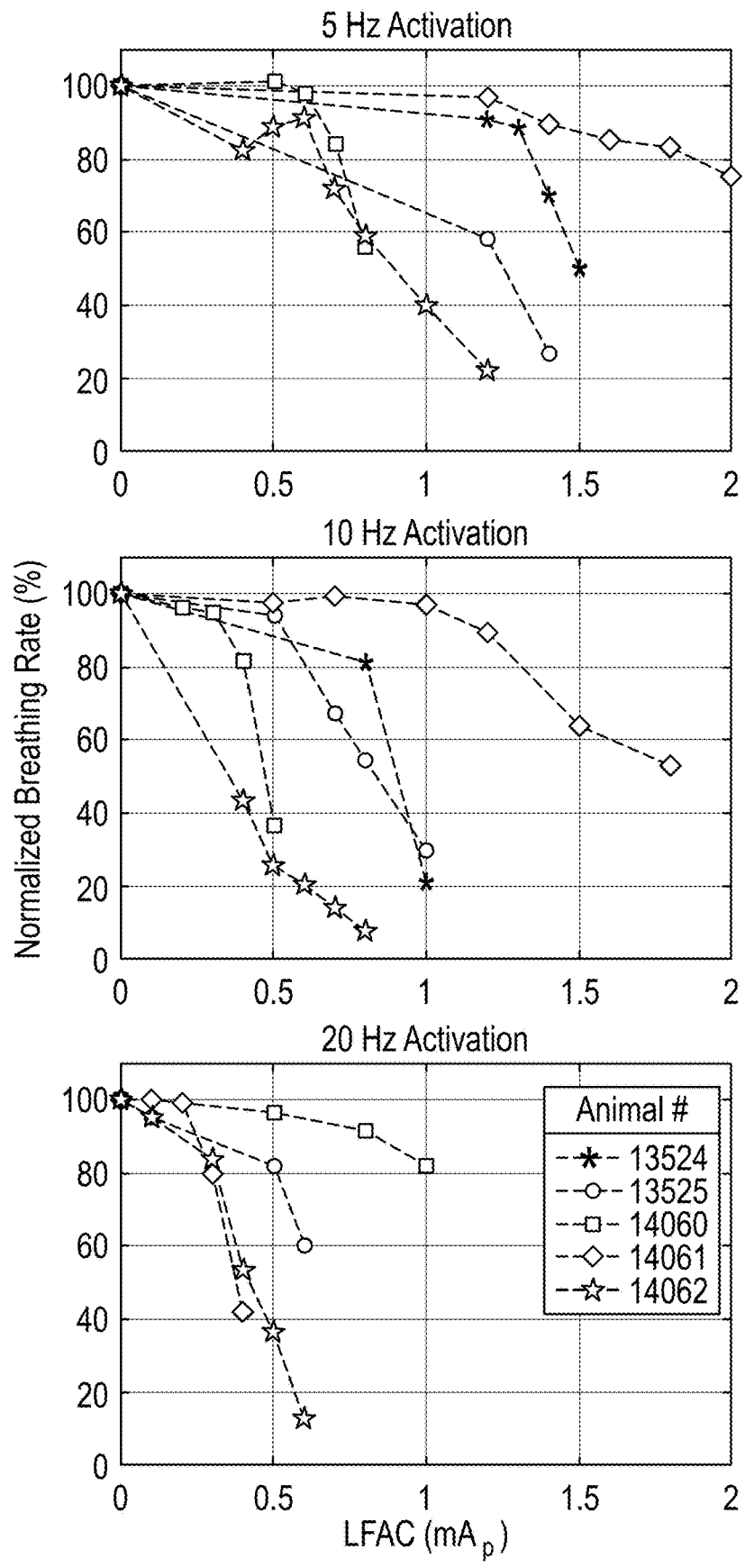
FIG. 22 illustrates experimental data regarding normalized breathing rate percentages plotted as function of the applied LFAC amplitudes, namely 5 Hz, 10 Hz, and 20 Hz in the anesthetized pig model.

FIG. 22 depicts, from this study, normalized breathing rate percentages with respect to the averaged breathing rate during baseline. Each result is plotted as function of the applied LFAC amplitudes with 5 Hz (top panel in FIG. 22), 10 Hz (middle panel in FIG. 22), and 20 Hz (bottom panel in FIG. 22). As shown in FIG. 22, the normalized breathing rate percentages tend to decrease at lower intensities and higher waveform frequencies. Moreover, the breathing rate curves are seen to shift to the left with increasing frequencies, indicating that the necessary stimulus threshold levels are lower at higher frequencies. The maximum reduction in breathing rate of each animal required higher intensity, however, with higher frequencies, lower intensity is required to reach the same maximum reduction.

Figure 23:
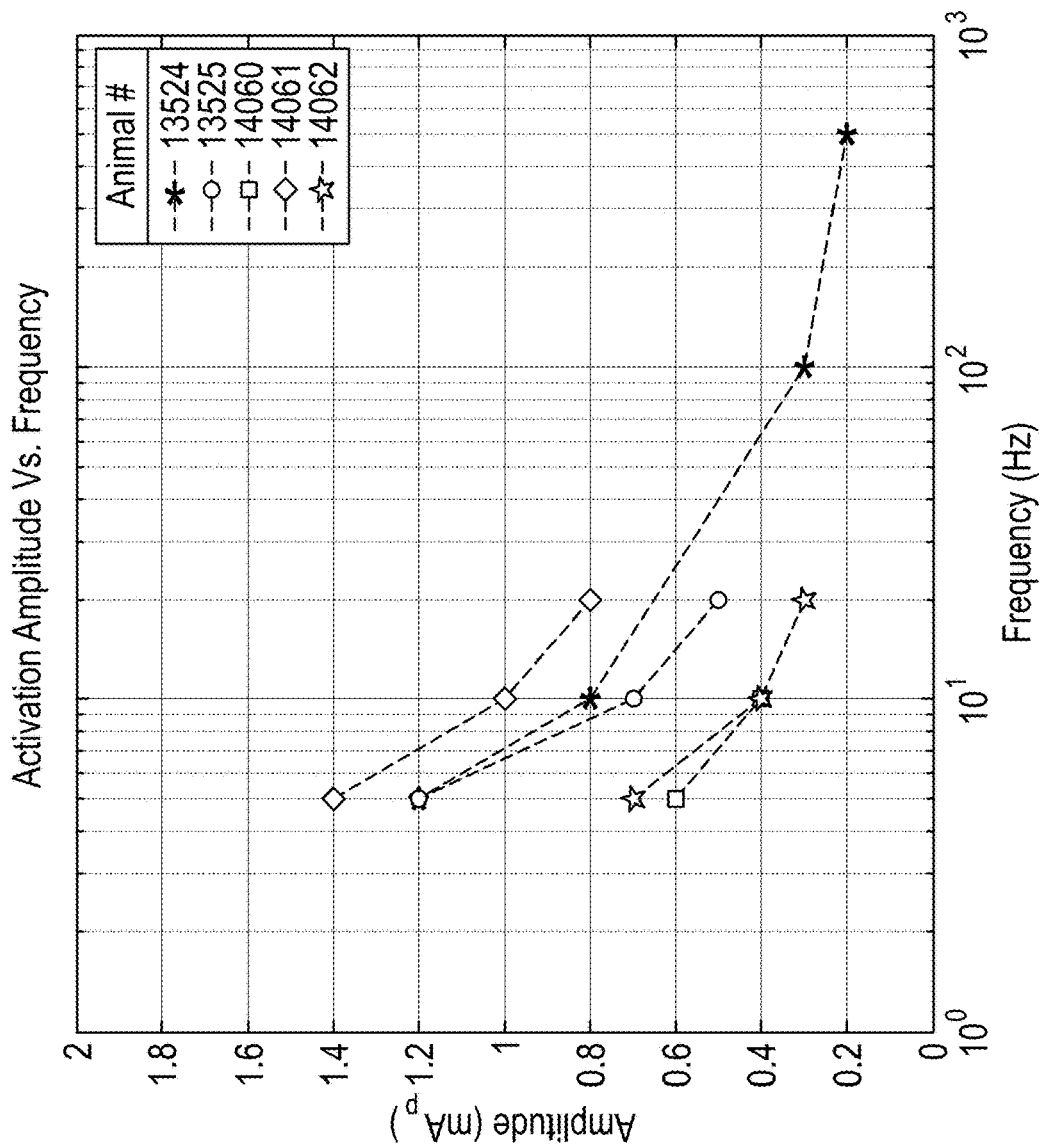
FIG. 23 illustrates activation threshold curves as function of the applied LFAC frequency from experimentation that sought to induce Hering-Breuer reflex in a plurality of swine.

FIG. 23 illustrates the resulted activation threshold curves as function of the applied LFAC frequency to induce HB reflex. Each threshold was determined by the minimum applied LFAC amplitude that evoked steady HB reflex. In one experiment, 100 and 500 Hz where applied to test the change at higher frequencies. FIG. 23 displays that all animals showed the same activation threshold decreasing trend, which pronounces the inverse relationship between LFAC activation threshold and waveform frequency. These experimental threshold curves were constructed based on the minimum LFAC amplitudes that were capable to induce a steady HB reflex. In one experiment, 100 Hz LFAC and 500 Hz LFAC stimulation were applied to further assess the threshold-frequency dependency and the results revealed even lower activation thresholds.

Additionally, applying the LFAC waveform at frequencies of 5 Hz, 10 Hz, and 20 Hz revealed that the activation threshold is frequency-dependent. Moreover, with respect to activation, the higher the LFAC frequency, the lower the stimulation current needed to reach the threshold, as shown in FIGS. 21 and 22. Further, the activation thresholds were within the defined water window of the activation electrode, which resulted in no apparent damage to the nerve or the electrodes themselves. It should be noted that this work was conducted in a large nerve trunk having a 3 to 4 millimeter (mm) diameter. Other experiments that involved rat vagus demonstrated LFAC block in a relatively small 0.5 mm diameter nerve for an efferent pathway biomarker, bradycardia. This was repeated in the large swine nerve against an afferent pathway biomarker, HB reflex. Further, both LFAC-based nerve conduction block and nerve activation were obtained using the same electrode and the same preparation method. Again, LFAC block thresholds are lower than LFAC activation thresholds, and are not observed to have a frequency dependence.

In exploring the mechanism behind the frequency dependency of LFAC for nerve activation, results from in-silico modeling indicate that the cable properties of nerve fibers, such as length and time constants, along with the activation function (which involves the geometry of the electrodes), can combine to play a role in this dependency. The influence of such parameters can directly influence the axon's transmembrane potential, which is determined by potential distributions in both time and space. In the case of myelinated fibers, spacing of electrode contacts may be tuned to target specific sites around the node of Ranvier, which have different fiber geometry dependency, and therefore influence the ionic channels dynamic for excitation. The mechanism behind the observed frequency dependency can be useful to enable the tuning of LFAC-based stimulation while limiting the off-target effects.

The feature of LFAC waveform frequency dependency combined with the observation of the independence of LFAC block thresholds to frequency can lead to the concept of the above-discussed block-activation (LFAC$_b$/LFAC$_a$) window. The block-activation window closes with increasing LFAC frequency such that at frequencies above 10 Hz, activation is the dominant effect. Such results further suggest that the underlying mechanism for LFAC block and LFAC activation are different. Further, LFAC activation may be asynchronous to the sinusoidal waveform, which would be a property that further distinguishes itself from activation via standard pulse stimulation. Additionally, LFAC is a stimulation modality built on a waveform that can be presented and tuned between activation and block by the frequency and amplitude of the sinusoidal waveform.

Figure 24:
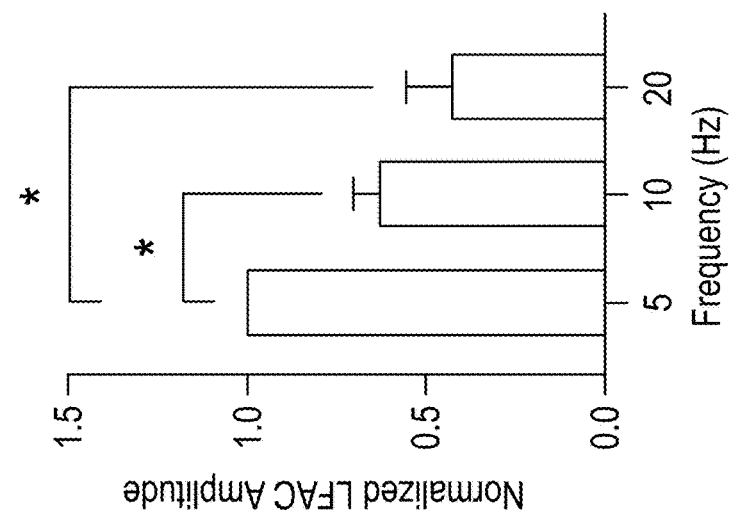
FIG. 24 illustrates test results demonstrating the effect of frequency on the activation threshold for LFAC for the Hering-Breuer reflex, and summarizing the data presented in FIGS. 21-23.

In this study, the use of LFAC to activate peripheral nerve fibers was assessed via direct quantification of the breathing rate as a biomarker indicating the activation of HB reflex. These findings demonstrate the feasibility of the LFAC waveform to induce peripheral nerve activation that results in an end organ functional change. As illustrated in FIG. 24, applying LFAC waveform at 5 Hz, 10 Hz, and 20 Hz also revealed that the activation threshold is a frequency dependent; the higher the frequency is, the lower threshold is required for activation. Moreover, the activation thresholds were within the defined water window of the activation electrode, which resulted in no apparent damage to the nerve or the electrodes themselves.

Given that the LFAC waveform can block nerve conduction at 1 Hz, these observations suggest the there is a window between block and activation using LFAC, and that window is frequency and amplitude dependent. Further results indicate the possibility for selective block, and that such a feature may be applied to activate nerve fibers preferentially.

Example IV

In this study, LFAC was delivered to cuff electrode similar to the cuff assembly 604 shown in FIGS. 14 and 15 that was positioned about the tibial branch of the sciatic nerve in a rat hind limb. LFAC blocking (LFAC$_b$) was captured by having a proximal pulse stimulation to evoke a compound action potential (CAP) to travel down the sciatic and towards the tibial branch where a distal LFAC cuff was located to induce a neural conduction block. The sinusoidal LFAC blocking waveform was applied at 1 Hz, 2 Hz, 3 Hz, and 4 Hz, and block was defined as the decrease in the evoked twitch peak force.

Figure 25:
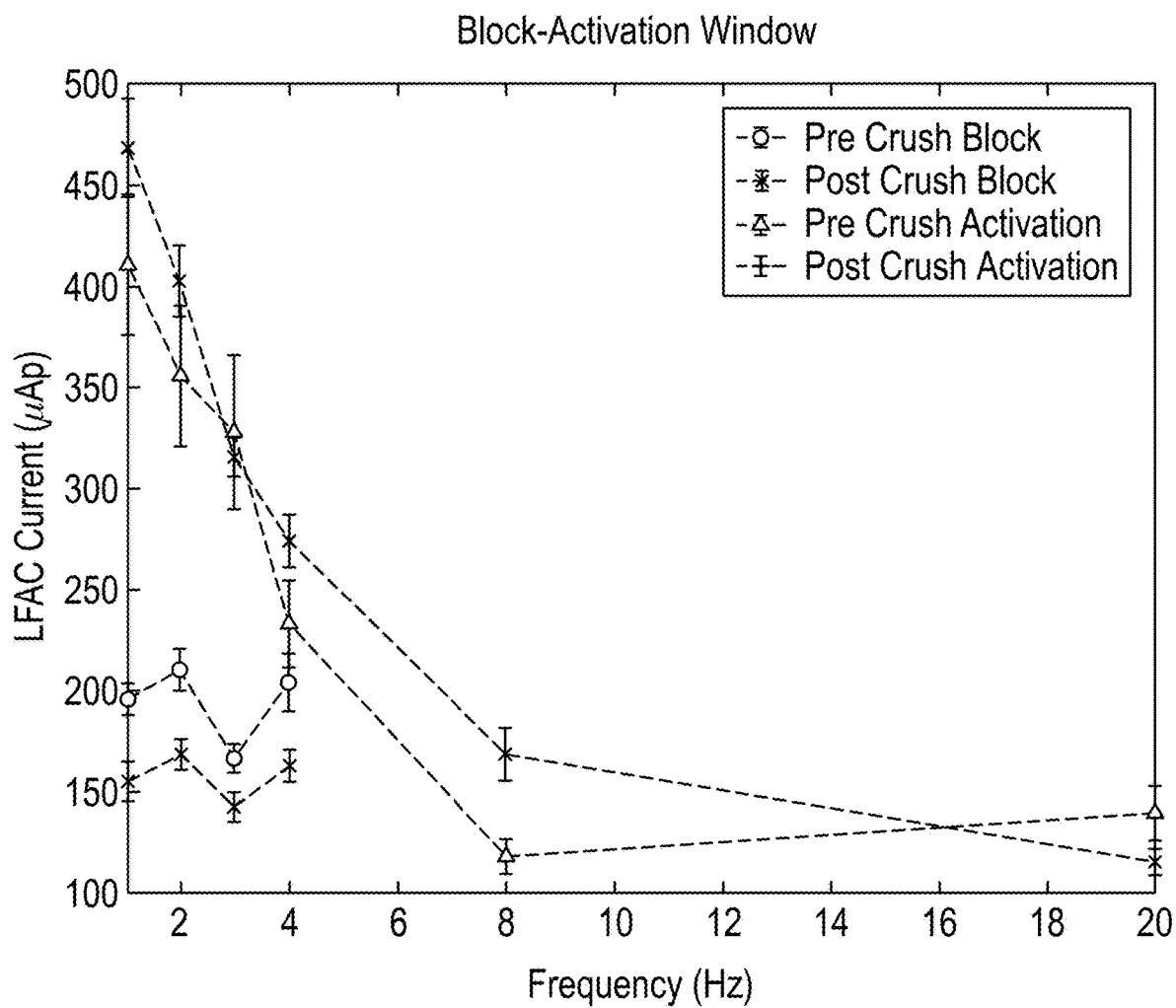
FIG. 25 illustrates block-activation threshold windows as a function of the applied LFAC frequency from data obtained from a study of a sciatic nerve in a rat hind limb.

For activation, the sinusoidal LFAC waveform was presented to the distal cuff at 1 Hz, 2 Hz, 3 Hz, 4 Hz, 8 Hz, and 20 Hz, and activation was defined as the onset of phasic twitches and their induced force. Response to the LFAC waveform, for block and activation, was measured using intramuscular (IM) EMG electrodes and force output from the triceps surae (TS) via a load cell. The sciatic nerve was crushed proximally following either a block or activation protocol, and stimulation testing was repeated to see how the reflex might affect the muscle response to LFAC. FIG. 25 shows the corresponding block-activation threshold window as a function of the applied LFAC frequency, with a standard deviation of 1/10th to better show the window between the blocking and activation thresholds.

Such a study has indicated that the reflexes had no significant effect on the LFAC waveforms ability to modulate the neural activity. Such results indicate the ability to initiate block of neural activity between 1 Hz and 4 Hz without causing the onset activation, with full block being achievable on the lower end, and more specifically, in the range of 1 about Hz to about 2 Hz. Furthermore, the LFAC activation threshold is frequency dependent, and the induced force output suggests orderly recruitment of muscle fibers and sustained contractions. Such modalities provide an indication of the ability to attain, as a low-power, no onset activation (for block), and a normal recruitment order of nerve fibers.

Example V

As discussed above, direct nerve stimulation using an electrical sinusoidal LFAC waveform can result in the blocking of conducting action potentials. However, with increasing LFAC frequency and/or amplitude, nerve block transitions into activation. A study was conducted that explored the nature of the transition between LFACb and LFACa, and to determine if the range of block or activation can be extended through manipulation of electrode design or stimulus waveform.

A bidomain model consisting of a finite element method model of a bipolar circumferential electrode, the nerve and volume conductor, and a NEURON based active nerve fiber model was implemented and used to run in-silico block and activation experiments. LFAC frequencies explored were between 0.1 Hz and 50 Hz. Amplitudes were increased until the threshold of nerve fiber block or activation was reached. The results of these simulations indicate that that LFACb is frequency independent, while LFACa thresholds decrease with increasing frequency, resulting in a block-activation window. Again, LFACa appeared to be orderly, with smaller nerve fibers having lower thresholds than larger nerve fibers. Thus, again, LFAC can have applications where orderly recruitment is important, such as functional electrical stimulation.

[0178] More specially, in this study simulations were performed within a bidomain modelling framework consisting of a finite element model (FEM) volume conductor model and an active nerve fiber model. The modelling framework was applied to predict and capture the block and activation behavior of myelinated nerve fibers to sinusoidal LFAC stimulation currents. The FEM model predicted the electrical distribution of potential and current density within the nerve bundle resulting from current sourced through a bipolar cuff electrode. The volume conductor model was performed in COMSOL Multiphysics (V5.5, COMSOL Inc., Burlington MA), and consisted of a 480 µm diameter monofascicular nerve bundle, a 500 µm internal diameter bipolar cuff electrode, and a 50 centimeter (cm) by 1 cm conductive tissue environment. The ends of the volume conductor were defined with infinite domain boundaries to increase the effective space to 2.5 m×1 m. The potentials from the volume conductor model were extracted along the locus of an axial and superficial nerve fiber and projected onto an active nerve fiber model using the NEURON simulation environment. The nerve fiber consisted of a version of the 2014 updated MRG model of a peripheral nervous system (PNS) myelinated axon, which had been extended to 503 nodes of Ranvier (NoR) in order to accommodate the geometric size of the FEM space. Python was used to translate, customize and allow for dynamic fiber diameter determination based on input.

In the block model, an action potential was initiated at one end of the nerve fiber using intracellular current injection. LFAC current is applied via bipolar electrodes placed at the midpoint of the nerve fiber. The action potential was tracked as it conducted down the nerve fiber to determine if it was slowed or blocked by the LFAC current. Block threshold, for at least terms of this study, was defined as the just necessary current to terminate nerve conduction. In the Activation Model, LFAC current was passed at increasing amplitudes until an action potential was produced. Threshold was defined as the just necessary current to generate a conducting action potential. Once the threshold data was collected, the tests was iterated against a different diameter nerve fiber. The diameters of MRG nerve fibers tested were 5.7 µm, 11.5 µm, and 16 µm, representing the extrema of fiber diameters as well as an intermediate case. The geometry of the bipolar cuff electrode used was that of a 5 mm long cuff with two symmetrically placed 0.5 mm contact widths spaced 1 mm edge-to-edge, 1.5 mm contact edge to end of cuff distance. The frequencies tested were 0.1 Hz, 0.5 Hz, 1 Hz, 5 Hz, 10 Hz, 15 Hz, 25 Hz, 35 Hz, and 50 Hz. The range of the extracellular stimulus was 1-800 mV, translating to a current range of approximately 0.09 to 73 µA based off the simulated effective impedance ascertained through the comparison of COMSOL result and input magnitudes.

Figure 26A:
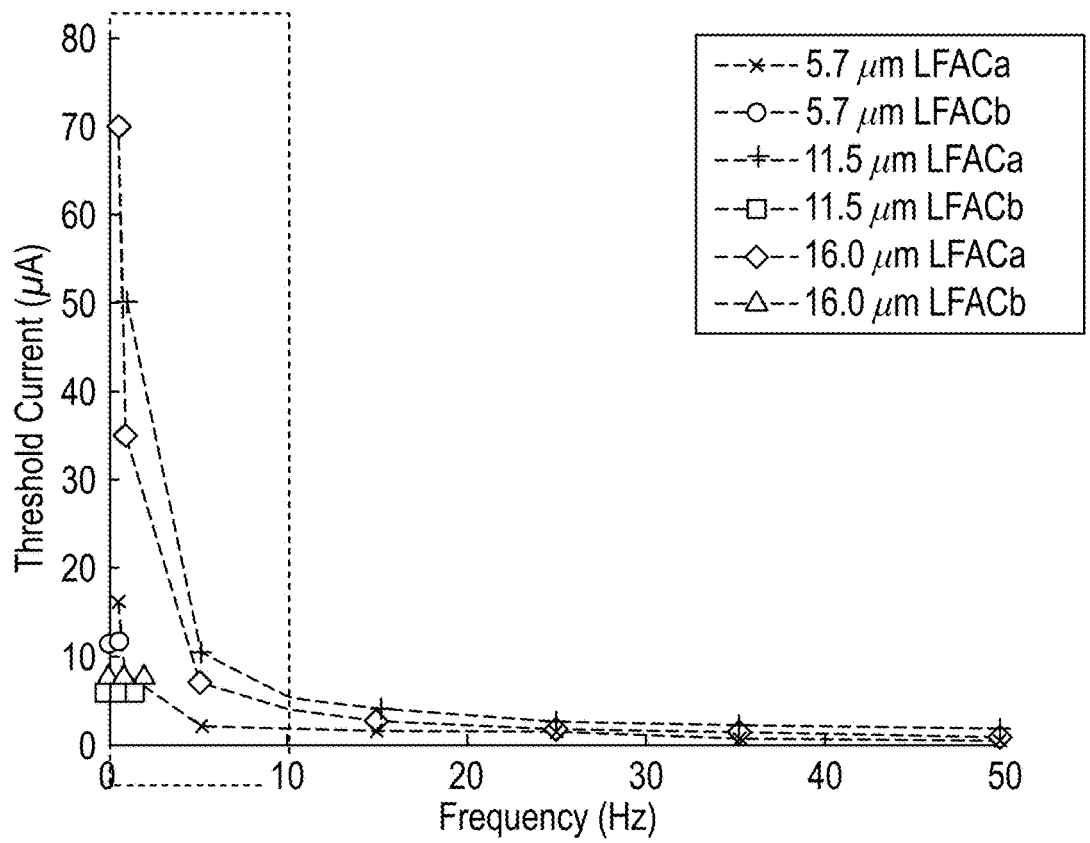
FIGS. 26A-C illustrate, from testing using an in-silico model, exemplary thresholds for LFAC block and activation as a function of LFAC frequency.
Figure 26B:
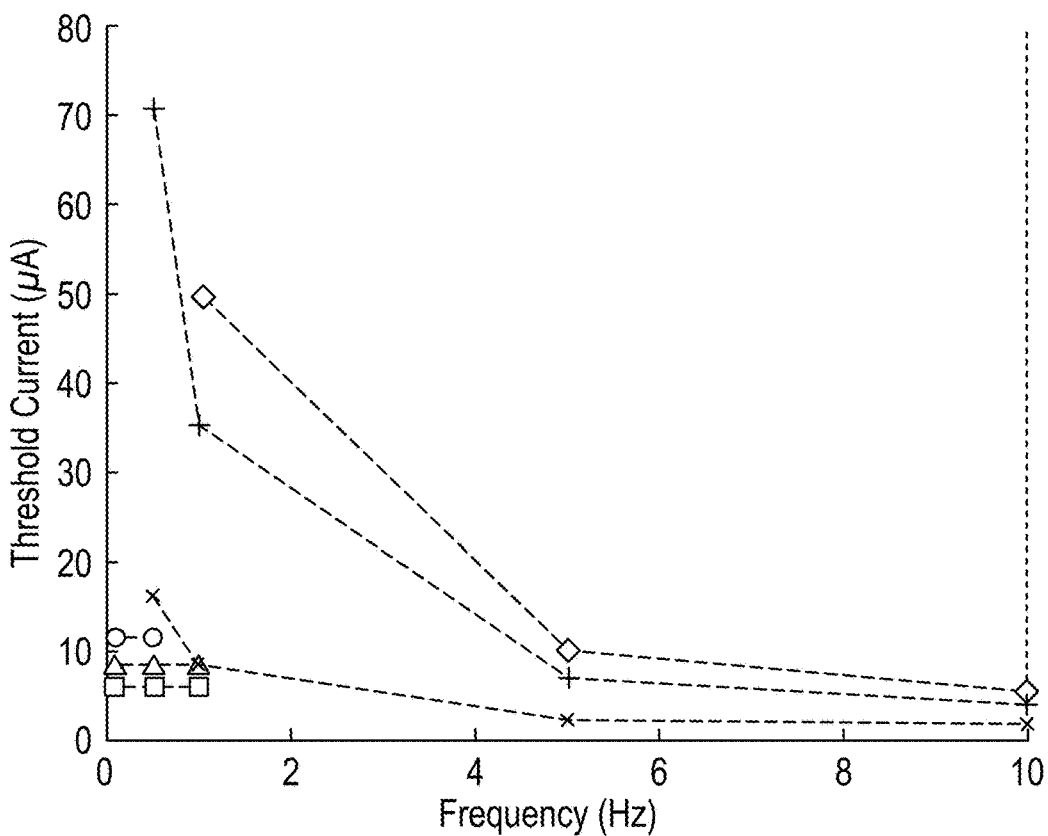
Figure 26C:
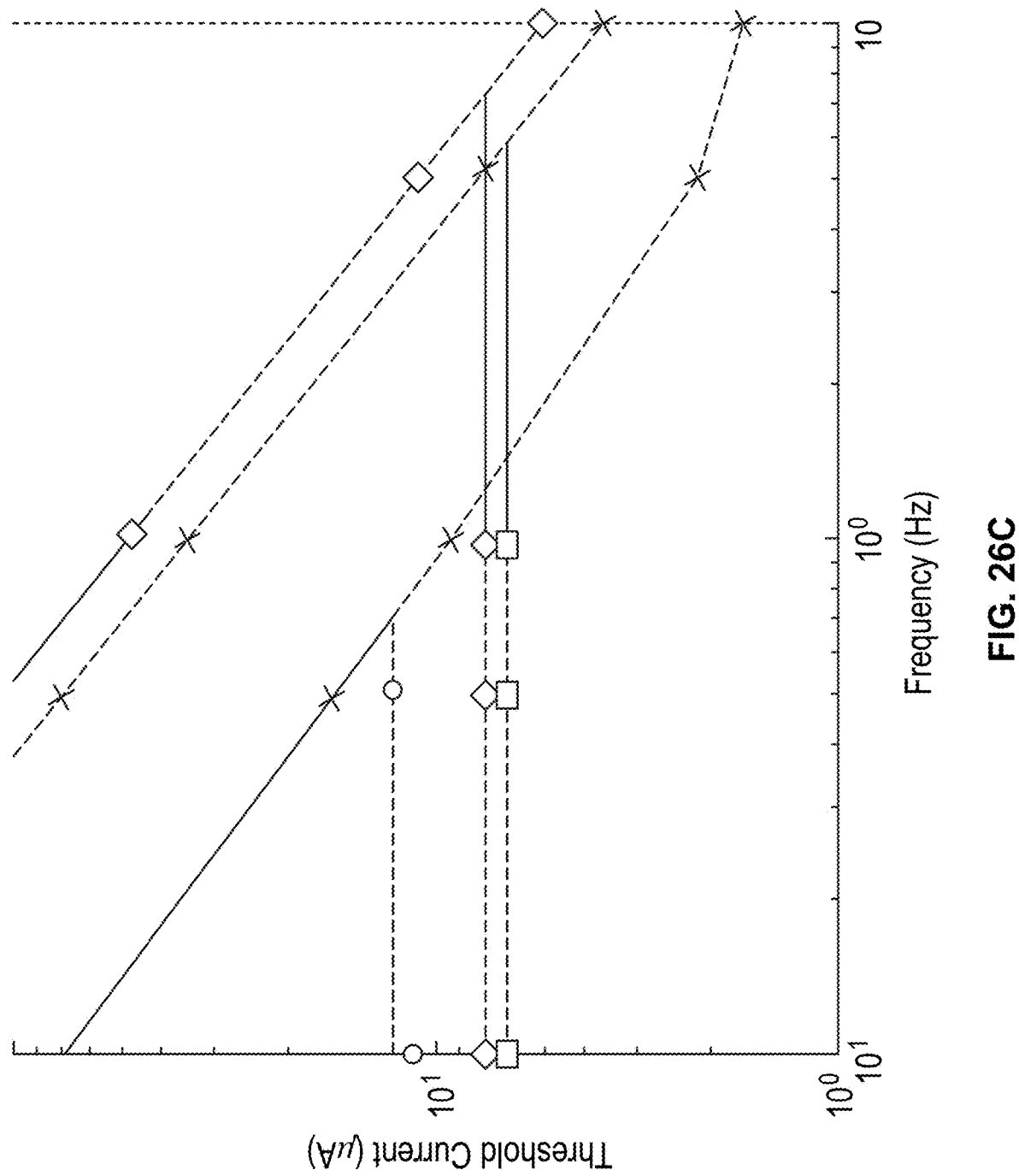

FIGS. 26A-C depict the thresholds of LFAC block and activation, as obtained from this data, as a function of LFAC frequency. Further, FIGS. 26A-C plot the same dataset to enable visualization at different domain ranges, with FIG. 26A showing the entire result dataset. As LFAC block was only found at low frequencies, FIGS. 26B (linear) and 13C (loglog) expand upon the frequency ranges less than 10 Hz. From this study, the threshold of $LFAC_b$ was again found to be frequency invariant. Further, of the three fiber diameters tested, the middle diameter (11.5 µm) was found to have the lowest block threshold. With respect to $LFAC_a$, again the threshold for LFACa decreased with increasing LFAC frequency. The shape of the threshold curves was reminiscent of those found in Weiss' Law for pulse stimulation suggesting a mechanism related to the cable properties of the nerve fiber. The smallest caliber nerve fibers (5.7 µm) had the lowest thresholds of activation, and the thresholds for larger fibers were ordered size-wise by nerve fiber caliber.

Consistent with the discussions above, this study further demonstrated that $LFAC_b$ thresholds are independent of frequency. As seen in FIGS. 26A-C, $LFAC_b$ is constant across the frequency range before activation occurred. Although not tunable with frequency, the electrode geometry and how it distributes the potential within the nerve bundle can play a role in the block-activation window. These geometric factors would include the contact width, the pitch between the contacts and, to some extent, the contact-to-edge distance. When changing the contact width, the number of NoR that falls under the contact will change. With small fibers, internodal distances are small as compared to larger fibers. Thus, more NoR relative to its length-constant can be influenced by the stimulus for small caliber fibers to preferentially influence the small fibers.

Increasing contact width and/or pitch could change the balance for blocking of larger caliber fibers. Contact pitch, the length between the electrode contacts, can also influence the amplitude of the potential for a given current injected. Shortening the pitch distance can increase the potential. Further, shortening the pitch while maintaining the distance to the end of the cuff can further change the balance of the current going directly between the contacts to that going outside the cuff towards the former case. These two factors can influence the balance between block and activation, and can change the relationships in the block-activation window. The contact-to-edge distance and the portion of the current which exits the cuff can also play a role in the creation of virtual electrodes outside of the cuff structure. These virtual electrodes can play a role in both activation and block. Thus, electrode geometry could play a significant role in shaping whether the LFAC results in block or activation.

As with the above-discussions, the study also demonstrated that $LFAC_a$ thresholds are frequency dependent. FIGS. 26A-C illustrate that $LFAC_a$ has a dependency on LFAC frequency. Further, larger LFAC amplitudes may be needed at lower frequencies to reach activation threshold, which can quickly drop off as frequency increases. Further, with the LFAC waveform, lower frequencies can favor time constants related to inactivation, while high frequencies favor those for activation. The activation thresholds relate to the sensitivity, spatial distribution and density of channels acted upon by the LFAC waveform.

There is a window in which fibers can be blocked before they are activated. Due to the factors mentioned above, a window can exist in which nerve conduction can be blocked without causing activation. This window can be at its widest at low frequency. Such a finding offers the ability to block neural activity without onset activation that is present in connection with other ES treatments, including kHFAC, and at a fraction of the current amplitude required.

$LFAC_a$ also appears to act preferentially on small caliber fibers. Moreover, in addition to $LFAC_b$ having the ability to block without onset activation, $LFAC_a$ seems to be size-wise. The $LFAC_b$ results show that the middle fiber diameter had the lowest threshold, suggesting that there could be a tuning function to $LFAC_b$ based on electrode geometry.

From the foregoing studies, LFAC can be utilized to activate nerves, with the activation threshold for LFAC decreasing with increasing frequency, thereby indicating that, unlike LFAC for block, LFAC for activation is frequency dependent. Additionally, such activation has been discovered to activate nerve fibers in order of size, with small nerve fibers having lower thresholds than large larger fibers. Such size-wise recruitment of activity via us of LFAC is opposite of pulse stimulation, wherein large, fatigable fibers are activated prior to smaller, fatigue resistant fibers. Further, LFAC activation can provide the ability to directly activate small fibers without activating larger ones, which represents a paradigm shift for neuromodulatory methods. It is believed LFAC is able to activate by fiber size because the stimulation waveform is a pure tone (1 frequency), and is more selective than pulse stimulation, which presents all frequencies simultaneously. As such, LFAC is able to target fibers based on their membrane time constants and space constants.

As will be appreciated from the descriptions herein, a wide variety of aspects and embodiments are contemplated by the present disclosure, examples of which include, without limitation, the aspects and embodiments listed below:

A cuff assembly for positioning an electrode along a nerve that includes: (i) a cuff having a through hole that extends along an axis of the cuff; (ii) a radial opening extending along a length of the cuff; (iii) a window defined in, and extends radially through a portion of, the cuff, the window configured to provide a location for an electrode to be coupled to the cuff; and (iv) a sliding closure selectively coupleable to the cuff to substantially close the radial opening; wherein, the cuff is sized to position a nerve in the through hole and slide the sliding closure into the radial opening to substantially lock the nerve in the cuff assembly.

A cuff assembly in accordance with any other embodiment disclosed herein that further comprises an electrode material positioned at least partially within the window and configured to communicate with electrical signals of a nerve positioned within the through hole.

A cuff assembly in accordance with any other embodiment disclosed herein that further comprises an electrical lead in contact with the electrode material to transfer electrical signals to and from the electrode material.

A cuff assembly in accordance with any other embodiment disclosed herein wherein the electrode material comprises an adhesive and a carbon filler material entrained in the adhesive.

A cuff assembly in accordance with any other embodiment disclosed herein wherein the carbon filler material comprises a carbon graphite material.

A cuff assembly in accordance with any other embodiment disclosed herein wherein the electrode material is coated with an insulated material along a radially exterior surface of the electrode material.

A cuff assembly in accordance with any other embodiment disclosed herein wherein the electrode material is coated with an electrochemical coating along a radially interior surface of the electrode material.

A cuff assembly in accordance with any other embodiment disclosed herein wherein the electrochemical coating comprises an intrinsically conducting polymer having finely divided conductive particles entrained therein.

A cuff assembly in accordance with any other embodiment disclosed herein wherein the finely divided conductive particles comprise a member selected from the group consisting of carbon black, nano-carbon black, carbon nanotubes, carbon nanoribbons, graphene, and combinations thereof.

A cuff assembly in accordance with any other embodiment disclosed herein that further comprises a grounding well defined in the sliding closure at a substantially middle position of the sliding closure.

A cuff assembly in accordance with any other embodiment disclosed herein that further comprises a stop defined at one end of the sliding closure, wherein the stop contacts the cuff upon the sliding closure being slidingly displaced along the radial opening to a position at which the sliding closure is fully coupled to the cuff to prevent further movement of the sliding closure relative to the cuff.

A cuff assembly in accordance with any other embodiment disclosed herein wherein the radial opening has a radial opening angle of about sixty degrees.

A cuff assembly in accordance with any other embodiment disclosed herein wherein the electrode material extends about 270-275 degrees about the through hole.

A cuff assembly in accordance with any other embodiment disclosed herein wherein the cuff has a C-shaped profile sized to extend approximately 80 percent of a circumference of the through hole.

A cuff assembly in accordance with any other embodiment disclosed herein wherein the cuff has a wall thickness of no more than about 500 µm.

A cuff assembly in accordance with any other embodiment disclosed herein wherein the window is inset within a wall of the cuff.

A cuff assembly in accordance with any other embodiment disclosed herein wherein the sliding closure has an overlap on either side of the radial opening along the length of the cuff when positioned therein.

A method of forming a cuff assembly that includes: (i) providing a cuff having a through hole defined through an axis of the cuff, a radial opening extending along a length of the cuff, and a window that extends through a portion of the cuff to the through hole and is configured to provide a location for an electrode to be coupled to the cuff; (ii) providing a closure that is selectively coupleable to the cuff to substantially close the radial opening; (iii) forming an electrode material within the window, the electrode material comprising an adhesive and a carbon filler material; and (iv) electrochemically coating a first surface of the electrode material facing toward the through hole with an ICP having finely divided conductive particles entrained therein; wherein, the cuff is sized to position a nerve in the through hole so the nerve is positioned at least partially along the electrode material.

A method in accordance with any other embodiment disclosed herein that further comprises, before the forming, placing the cuff around a mold having a diameter similar to the through hole and masking the window with silicone from the inner surface to the inset edge.

A method in accordance with any other embodiment disclosed herein that further comprises, before the forming, adding wires through the window before or during the filling the window step.

A method in accordance with any other embodiment disclosed herein that further comprises, before the coating, insulating a second surface of the electrode material facing away from the through hole and the wires extending from the electrode material.

A method in accordance with any other embodiment disclosed herein wherein the ICP comprises poly(3,4 ethylenedioxythiophene):poly(4-styrenesulfonic acid) (PEDOT:PSS).

A method in accordance with any other embodiment disclosed herein wherein the finely divided conductive particles are selected from the group consisting of carbon black (CB), nano-carbon black, carbon nanotubes, carbon nanoribbons, graphene, and combinations thereof.

A method for forming an interface coating on a nerve-facing bioelectric surface of an electrode for delivering an electrical impulse to a nerve in an animal that includes: (i) providing an aqueous solution or suspension comprising 3,4-ethylenedioxy-thiophene (EDOT), poly(4-styrenesulfonic acid) (PSS) and a carbon nanomaterial; (ii) submerging in the aqueous solution or suspension an electrode configured for delivering an electrical impulse to a nerve in an animal, wherein a nerve-facing bioelectric surface of the electrode is in contact with the aqueous solution or suspension; and (iii) forming an interface coating on the nerve-facing bioelectric surface by electrodeposition; wherein the interface coating comprises electroplated poly(3,4 ethylenedioxythiophene):poly(4-styrenesulfonic acid) with a dispersed carbon nanomaterial filler.

A method in accordance with any other embodiment disclosed herein wherein the carbon nanomaterial comprises carbon black.

A method in accordance with any other embodiment disclosed herein wherein the aqueous solution or suspension comprises from about 1 to about 20 mg/mL EDOT, from about 4 to about 10 mg/mL PSS and from about 0.5 to about 4 mg/mL carbon black.

A method in accordance with any other embodiment disclosed herein wherein the electrodeposition comprises potentiostatic deposition at a DC voltage of from about ±0.5 to about ±1.5 for a time period of from about 15 minutes to about 25 minutes.

A method in accordance with any other embodiment disclosed herein wherein the electrodeposition comprises galvanostatic deposition at from about ±150 to about ±250 µA for a time period of from about 3 minutes to about 7 minutes.

A method in accordance with any other embodiment disclosed herein wherein the interface coating has an average thickness of from about 100 micrometer (µm) to about 1 millimeter (mm).

A method in accordance with any other embodiment disclosed herein wherein the bioelectric surface is a bioelectric surface of an implantable electrode.

A method in accordance with any other embodiment disclosed herein wherein the implantable electrode comprises an implantable cuff.

A method in accordance with any other embodiment disclosed herein wherein the bioelectric surface is configured for external contact with a skin surface for delivery of an electrical signal to a nerve through the skin.

A method in accordance with any other embodiment disclosed herein that further comprises, before the submerging, covering one or more surface of the electrode material on which the interface coating is not to be formed.

A method in accordance with any other embodiment disclosed herein wherein the nerve-facing bioelectric surface of the electrode upon which the interface coating is formed is a porous surface.

A method in accordance with any other embodiment disclosed herein wherein the porous surface is composed of an adhesive and a carbon filler material.

A method in accordance with any other embodiment disclosed herein wherein the carbon filler material comprises a carbon graphite material.

A method in accordance with any other embodiment disclosed herein wherein the adhesive comprises a cyanoacrylate adhesive.

An electrode having an interface coating made in accordance with any method embodiment disclosed herein.

An electrode for delivering an electrical impulse to a nerve in an animal that includes: (i) a bioelectric surface configured to face a nerve when the electrode is positioned for use; and (ii) an interface coating on the bioelectric surface; wherein the interface coating comprises electroplated poly(3,4 ethylenedioxythiophene):poly(4-styrenesulfonic acid) with a dispersed carbon nanomaterial filler.

An electrode in accordance with any other embodiment disclosed herein wherein the carbon nanomaterial comprises carbon black.

An electrode in accordance with any other embodiment disclosed herein wherein the interface coating has an average thickness of from about 100 micrometer (µm) to about 1 millimeter (mm).

An electrode in accordance with any other embodiment disclosed herein wherein the bioelectric surface is a bioelectric surface of an implantable electrode.

An electrode in accordance with any other embodiment disclosed herein wherein the implantable electrode comprises an implantable cuff.

An electrode in accordance with any other embodiment disclosed herein wherein the bioelectric surface is configured for external contact with a skin surface for delivery of an electrical signal to a nerve through the skin.

An electrode in accordance with any other embodiment disclosed herein wherein the nerve-facing bioelectric surface of the electrode upon which the interface coating is formed is a porous surface.

An electrode in accordance with any other embodiment disclosed herein wherein the porous surface is composed of an adhesive and a carbon filler material.

An electrode in accordance with any other embodiment disclosed herein wherein the carbon filler material comprises a carbon graphite material.

An electrode in accordance with any other embodiment disclosed herein wherein the adhesive comprises a cyanoacrylate adhesive.

A conductive material comprising poly(3,4 ethylenedioxythiophene):poly(4-styrenesulfonic acid) (PEDOT:PSS) with a dispersed carbon nanomaterial filler entrained therein, wherein the carbon nanomaterial filler is randomly dispersed within the PEDOT:PSS.

A conductive material comprising first and second layers, wherein the first layer comprises a porous surface in contact with the second layer, and wherein the second layer comprises poly(3,4 ethylenedioxythiophene):poly(4-styrenesulfonic acid) with a dispersed carbon nanomaterial filler.

A conductive material in accordance with any other embodiment disclosed herein wherein the carbon nanomaterial comprises carbon black.

A conductive material in accordance with any other embodiment disclosed herein wherein the porous surface is composed of an adhesive and a carbon filler material.

A conductive material in accordance with any other embodiment disclosed herein wherein the carbon filler material comprises a carbon graphite material.

A conductive material in accordance with any other embodiment disclosed herein wherein the adhesive comprises a cyanoacrylate adhesive.

A conductive material in accordance with any other embodiment disclosed herein wherein the second layer has an average thickness of from about 100 micrometer (µm) to about 1 millimeter (mm).

A method that includes: (i) delivering a LFAC waveform to a cuff assembly, the cuff assembly being configured for implantation in or around a nerve and having a plurality of electrodes; (ii) increasing a frequency of the LFAC waveform to transition from a first frequency utilized for nerve block to a second frequency utilized for nerve activation, the first frequency being less than 4 Hz and is less than the second frequency; (iii) transmitting, from one or more of the plurality of electrodes and to the nerve, an electrical signal corresponding to the delivered LFAC waveform; and (iv) monitoring a response a receipt of the transmitted electrical signal.

A method in accordance with any other embodiment disclosed herein wherein the second frequency is less than 20 Hz.

A method in accordance with any other embodiment disclosed herein that further includes increasing an amplitude of the LFAC waveform from a first amplitude to a second amplitude, the second amplitude being utilized with the activation of the nerve.

A method in accordance with any other embodiment disclosed herein that further includes, in response to the increase to the second amplitude, decreasing the LFAC waveform from the second frequency to a third frequency, the third frequency being larger than the first frequency.

A method in accordance with any other embodiment disclosed herein that further includes providing the LFAC waveform at a current that is less than 1000 micro amps.

A method in accordance with any other embodiment disclosed herein that further includes adjusting the frequency of the LFAC waveform to control ordered size-wise activation of nerve fibers.

A method for treating a nerve of a patient that includes: (i) delivering an electrical stimulation to a cuff assembly that is secured to, or around, the nerve, the electrical stimulation being a low frequency alternating current (LFAC) waveform having a frequency of less than 100 hertz (Hz); and (ii) adjusting at least one of the frequency and an amplitude and of the LFAC waveform to elicit either a block or an activation the nerve.

A method in accordance with any other embodiment disclosed herein wherein said adjusting comprises increasing the frequency of the LFAC waveform to transition from the delivered electrical stimulation facilitating the block of the nerve to facilitating the activation of the nerve.

A method in accordance with any other embodiment disclosed herein wherein said increasing the frequency of the LFAC waveform includes increasing the frequency from a first frequency that is below 4 Hz to a second frequency that is within a range of 4 Hz to 20 Hz.

A method in accordance with any other embodiment disclosed herein that further includes increasing the amplitude of the LFAC waveform.

A method in accordance with any other embodiment disclosed herein wherein said adjusting comprises decreasing the frequency of the LFAC waveform to transition from the delivered electrical stimulation facilitating the activation of the nerve to facilitating the block of the nerve.

A method in accordance with any other embodiment disclosed herein wherein decreasing the frequency comprises decreasing the frequency from a first frequency that is above 4 Hz.

A method in accordance with any other embodiment disclosed herein wherein said adjusting further comprises decreasing the amplitude of the LFAC waveform.

A method in accordance with any other embodiment disclosed herein wherein said adjusting further includes increasing at least one of the frequency and the amplitude to attain at least one of a unitary activation and a burst activation of the nerve.

A method in accordance with any other embodiment disclosed herein that further includes monitoring at least one of a neural interface and an electrochemical interface between the cuff assembly and a nerve and/or tissue around the nerve.

A method in accordance with any other embodiment disclosed herein wherein said adjusting comprises increasing the frequency of the LFAC waveform to facilitate activation of the nerve such that fiber recruitment is ordered size-wise from smaller fibers to larger fibers.

A system that includes: (i) a control system having a voltage controlled voltage source, a pattern generator, and a linear optolsolator, the pattern generator configured to generate a LFAC waveform for at least nerve activation, the LFAC waveform having a frequency between 4 HZ and 20 Hz; and (ii) a cuff assembly configured for implantation in a patient, the cuff assembly having a plurality of electrodes, one or more of the plurality of electrodes electrically coupled to the control system and adapted to deliver an electrical signal corresponding to the LFAC waveform.

A system in accordance with any other embodiment disclosed herein wherein the pattern generator is adapted to lower one or both of the frequency and an amplitude of the LFAC waveform to transition the LFAC waveform from having characteristics used with nerve activation to having characteristics used with nerve block.

A system in accordance with any other embodiment disclosed herein wherein the control system is adapted to monitor at least one of a neural interface and an electrochemical interface between the cuff assembly and a nerve and/or tissue around the nerve.

A system in accordance with any other embodiment disclosed herein wherein at least the frequency of the LFAC waveform is adjustable by the control system to control activation of the nerve such that fiber recruitment is ordered size-wise from smaller fibers to larger fibers.

While the various aspects of the invention have been described in connection with what are presently considered to be the most practical and preferred embodiments, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. A cuff assembly for positioning an electrode along a nerve, comprising:
 a cuff having a through hole that extends along an axis of the cuff;
 a radial opening extending along a length of the cuff;
 a window defined in, and extends radially through a portion of a cuff wall of the cuff, the window configured to provide a location for an electrode to be coupled to the cuff;
 a sliding closure selectively coupleable to the cuff to substantially close the radial opening;

an electrode material positioned at least partially within the window and configured to communicate with electrical signals of a nerve positioned within the through hole;

wherein, the cuff is sized to position a nerve in the through hole and slide the sliding closure into the radial opening to substantially lock the nerve in the cuff assembly, wherein the electrode material is coated with an electrochemical coating along a radially interior surface of the electrode material, and wherein the electrochemical coating comprises an intrinsically conducting polymer having finely divided conductive particles entrained therein.

2. The cuff assembly of claim 1 wherein the finely divided conductive particles comprise a member selected from the group consisting of carbon black, nano-carbon black, carbon nanotubes, carbon nanoribbons, graphene, and combinations thereof.

3. The cuff assembly of claim 1, wherein the through hole is defined by the cuff wall along the axis.

4. The cuff assembly of claim 1, wherein the window has an inset positioned about a radially inner portion of the window, the inset configured to provide an area for an adhesion of the electrode material to the cuff wall.

5. The cuff assembly of claim 4, wherein the radially inner portion of the window defining an opening that provides an unobstructed exposure to the through hole.

6. The cuff assembly of claim 1, further comprising a window cover that extends across a portion of the window, the window cover configured to retain a wire of the electrode.

7. The cuff assembly of claim 1, further comprising a window cover that extends across a portion of the window, the window cover configured to retain the electrode material in the window.

8. The cuff assembly of claim 1, wherein the window extends radially to opposing sides of the cuff wall.

9. The cuff assembly of claim 1, wherein the radial opening extends through the cuff wall, and wherein the sliding closure is configured to slide into, and fit within, the radial opening along the cuff wall.

10. The cuff assembly of claim 1, wherein the sliding closure includes a lower segment configured to slide within the radial opening along the cuff wall, the lower segment including an overlap configured to radially extend within the through hole to opposing sides of the radial opening.

11. The cuff assembly of claim 10, wherein one end of the sliding closure includes a stop configured to contact the cuff wall at a location that corresponds to the sliding closure being slid within the radial opening to a fully closed position.

12. A cuff assembly for positioning an electrode along a nerve, comprising:
a cuff having a through hole that extends along an axis of the cuff;
a radial opening extending along a length of the cuff;
a window defined in, and extends radially through a portion of, the cuff, the window configured to provide a location for an electrode to be coupled to the cuff;
a sliding closure selectively coupleable to the cuff to substantially close the radial opening; and
a grounding well, that provides a location for a ground electrode, defined in the sliding closure at a substantially middle position of the sliding closure,
wherein, the cuff is sized to position a nerve in the through hole and slide the sliding closure into the radial opening to substantially lock the nerve in the cuff assembly.

13. The cuff assembly of claim 12, wherein the grounding well is a grounding well point at an isopotential line.

14. The cuff assembly of claim 12, wherein the grounding well is positioned at a ground plane located at a divide of the cuff at which a potential is substantially zero.

15. The cuff assembly of claim 12, wherein the radial opening extends through a cuff wall of the cuff that defines the through hole, and wherein the sliding closure is configured to slide into, and fit within, the radial opening along the cuff wall.

16. A cuff assembly for positioning an electrode along a nerve, comprising:
a cuff having a through hole that extends along an axis of the cuff;
a radial opening extending along a length of the cuff;
a window defined in, and extends radially through a portion of, the cuff, the window configured to provide a location for an electrode to be coupled to the cuff;
a sliding closure selectively coupleable to the cuff to substantially close the radial opening; and
a stop defined at one end of the sliding closure, wherein the stop contacts the cuff upon the sliding closure being slidingly displaced along the radial opening to a position at which the sliding closure is fully coupled to the cuff to prevent further movement of the sliding closure relative to the cuff,
wherein, the cuff is sized to position a nerve in the through hole and slide the sliding closure into the radial opening to substantially lock the nerve in the cuff assembly.

17. The cuff assembly of claim 16, wherein the through hole is defined by a cuff wall along the axis, and wherein the window extends through the cuff wall to provide an unobstructed exposure to the through hole.

18. The cuff assembly of claim 17, wherein the radial opening extends through the cuff wall, and wherein the sliding closure is configured to slid into, and fit within, the radial opening along the cuff wall.

19. The cuff assembly of claim 16, wherein the sliding closure includes a lower segment configured to slide within the radial opening, the lower segment having an overlap that is configured to radially extend within the through hole to opposing sides of the radial opening.

20. The cuff assembly of claim 16, wherein the window has an inset positioned about a radially inner portion of the window, the inset configured to provide an area for an adhesion of an electrode material to the cuff, the radially inner portion defining an opening that provides an unobstructed exposure to the through hole.

* * * * *